United States Patent
Barnett et al.

(10) Patent No.: US 9,461,973 B2
(45) Date of Patent: Oct. 4, 2016

(54) SYSTEMS AND METHODS FOR DECRYPTION AS A SERVICE

(71) Applicant: Bluefin Payment Systems, LLC, Atlanta, GA (US)

(72) Inventors: Timothy William Barnett, Roswell, GA (US); Alexander I. Kasatkin, Alpharetta, GA (US); Christopher Hozumi Miyata, Tulsa, OK (US); Daniel Ruehle, Smyrna, GA (US)

(73) Assignee: BLUEFIN PAYMENT SYSTEMS, LLC, Atlanta, GA (US)

( * ) Notice: Subject to any disclaimer, the term of this patent is extended or adjusted under 35 U.S.C. 154(b) by 1 day.

(21) Appl. No.: 14/663,238

(22) Filed: Mar. 19, 2015

(65) Prior Publication Data

US 2015/0271150 A1 Sep. 24, 2015

Related U.S. Application Data

(63) Continuation-in-part of application No. 14/591,223, filed on Jan. 7, 2015, now Pat. No. 9,355,374, and a continuation-in-part of application No. 14/591,171, filed on Jan. 7, 2015, and a continuation-in-part of (Continued)

(51) Int. Cl.
*G06F 21/44* (2013.01)
*H04L 29/06* (2006.01)
*G06F 21/73* (2013.01)

(52) U.S. Cl.
CPC ........... *H04L 63/0435* (2013.01); *G06F 21/44* (2013.01); *G06F 21/73* (2013.01); *H04L 63/061* (2013.01); *H04L 63/20* (2013.01)

(58) Field of Classification Search
CPC ... H04L 63/04; G06F 12/1408; G06F 21/60; G06F 12/14
See application file for complete search history.

(56) References Cited

U.S. PATENT DOCUMENTS

| | | | |
|---|---|---|---|
| 6,286,099 B1 | 9/2001 | Kramer | |
| 7,386,471 B1 | 6/2008 | Nack | |
| 7,731,435 B2 | 6/2010 | Piersol et al. | |
| 7,941,673 B1 | 5/2011 | Trimberger | |
| 8,429,041 B2 | 4/2013 | Bonalle et al. | |
| 8,555,083 B1 * | 10/2013 | Nanda | H04L 9/0869 380/277 |

(Continued)

FOREIGN PATENT DOCUMENTS

| | | |
|---|---|---|
| CN | 102387501 A | 3/2012 |
| KR | 20090039301 A | 4/2009 |

OTHER PUBLICATIONS

International Search Report and Written Opinion mailed Sep. 4, 2015 for related PCT application No. PCT/US2015/21595.

(Continued)

*Primary Examiner* — Izunna Okeke
(74) *Attorney, Agent, or Firm* — Morris, Manning & Martin, LLP; John R. Harris, Esq.; Bryan D. Stewart, Esq.

(57) ABSTRACT

Systems and methods for decryption of payloads are disclosed herein. In various embodiments, systems and methods herein are configured for decrypting thousands of transactions per second. Further, in particular embodiments, the systems and methods herein are scalable, such that many thousands of transactions can be processed per second upon replicating particular architectural components.

41 Claims, 21 Drawing Sheets

EXEMPLARY DECRYPTION VERIFICATION PROCESS

Related U.S. Application Data application No. 14/591,218, filed on Jan. 7, 2015, and a continuation-in-part of application No. PCT/US2015/010405, filed on Jan. 7, 2015.

(60) Provisional application No. 61/955,739, filed on Mar. 19, 2014.

(56) References Cited

U.S. PATENT DOCUMENTS

| | | |
|---|---|---|
| 2002/0082896 A1 | 6/2002 | Inagi |
| 2003/0035569 A1 | 2/2003 | Chau |
| 2003/0051150 A1 | 3/2003 | Jung |
| 2005/0166082 A1 | 7/2005 | Williams et al. |
| 2007/0005974 A1 | 1/2007 | Kudou |
| 2008/0049644 A1 | 2/2008 | Halbert |
| 2008/0320317 A1 | 12/2008 | Funahashi et al. |
| 2010/0306635 A1 | 12/2010 | Tang et al. |
| 2010/0325710 A1 | 12/2010 | Etchegoyen |
| 2010/0325734 A1 | 12/2010 | Etchegoyen |
| 2010/0332396 A1 | 12/2010 | Etchegoyen |
| 2010/0332400 A1 | 12/2010 | Etchegoyen |
| 2011/0093503 A1 | 4/2011 | Etchegoyen |
| 2011/0093703 A1 | 4/2011 | Etchegoyen |
| 2011/0196754 A1 | 8/2011 | Proud et al. |
| 2011/0307710 A1 | 12/2011 | McGuire et al. |
| 2012/0030209 A1 | 2/2012 | Bause et al. |
| 2012/0054050 A1 | 3/2012 | Ziegler et al. |
| 2012/0084206 A1 | 4/2012 | Mehew et al. |
| 2012/0324242 A1 | 12/2012 | Kirsch |
| 2013/0036098 A1 | 2/2013 | Mutalik et al. |
| 2013/0254117 A1 | 9/2013 | Von Mueller et al. |
| 2013/0297579 A1 | 11/2013 | Andrew et al. |
| 2013/0311434 A1 | 11/2013 | Jones |
| 2014/0173686 A1 | 6/2014 | Kgil et al. |
| 2014/0344921 A1 | 11/2014 | Hamlin et al. |
| 2015/0220635 A1 | 8/2015 | Deen et al. |
| 2015/0220636 A1 | 8/2015 | Deen et al. |
| 2015/0221336 A1 | 8/2015 | Deen et al. |
| 2015/0381582 A1* | 12/2015 | O'Hare .................. G06F 21/606 713/189 |

OTHER PUBLICATIONS

Common Approval Scheme, Point of Interaction Protection Profile, Nov. 26, 2010 Version: 2.0, 161 pages.

Security Standards Council, Payment Card Industry (PCI) PIN Transaction Security (PTS) Point of Interaction (POI), Modular Security Requirements, Version 4.0 Jun. 2013, 59 pages.

International Search Report and Written Opinion mailed Apr. 13, 2015 for related PCT application No. PCT/US15/10405.

* cited by examiner

EXEMPLARY ENVIRONMENT

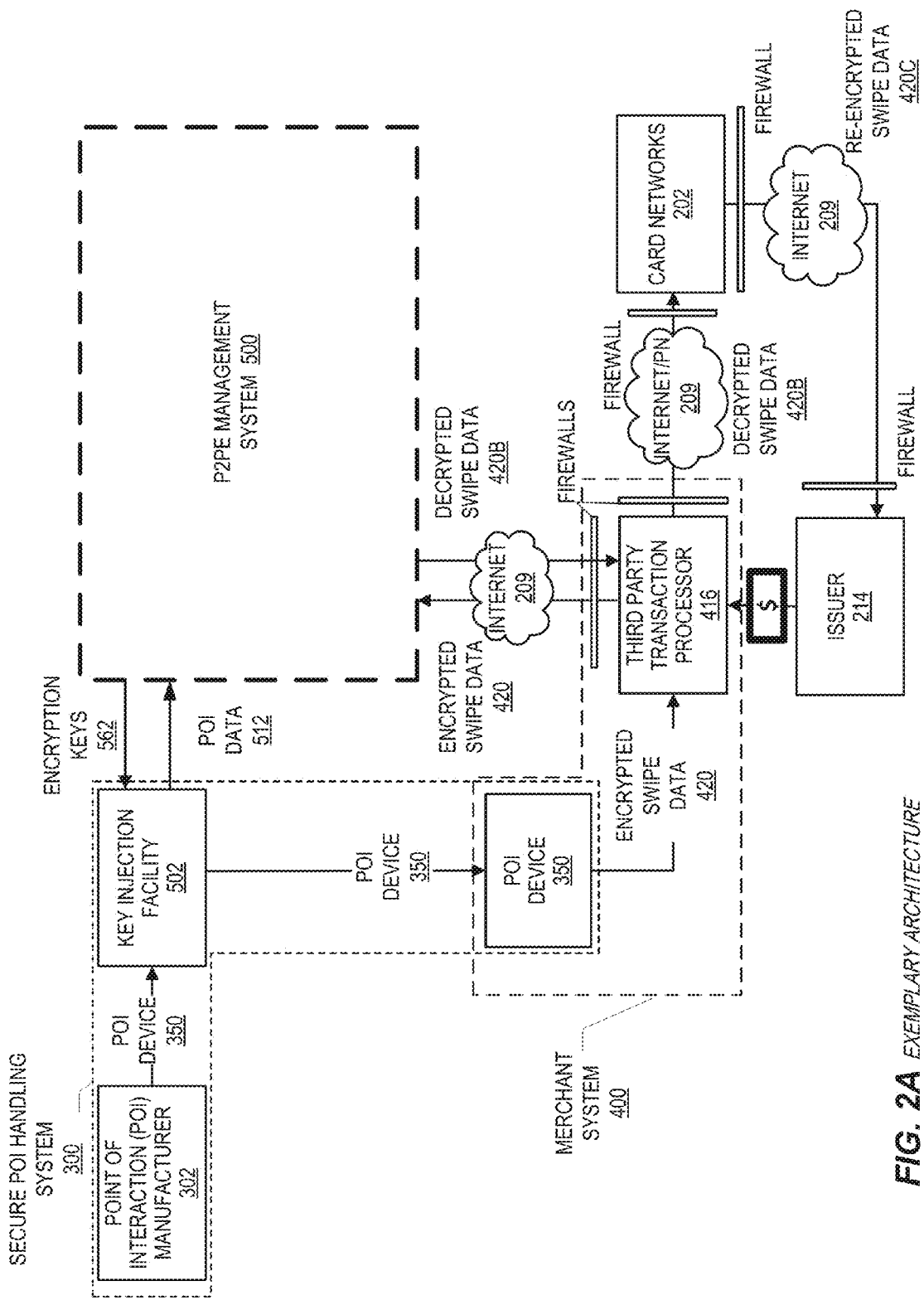
FIG. 2A EXEMPLARY ARCHITECTURE

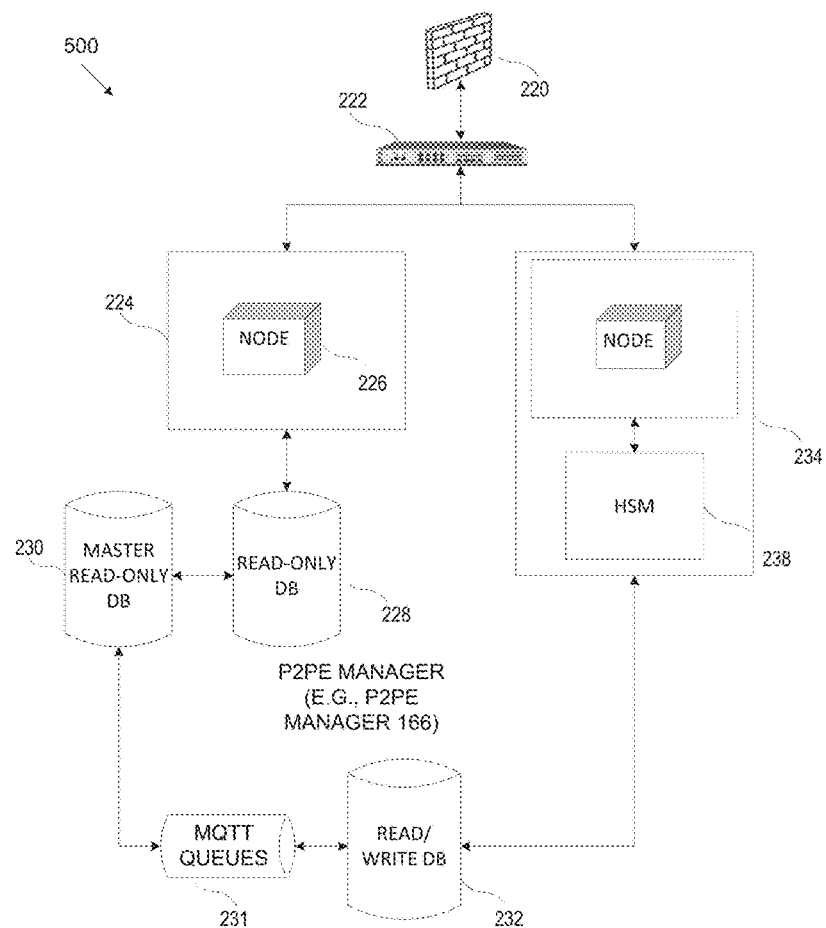
FIG. 2B *EXEMPLARY P2PE MANAGER SYSTEM ARCHITECTURE*

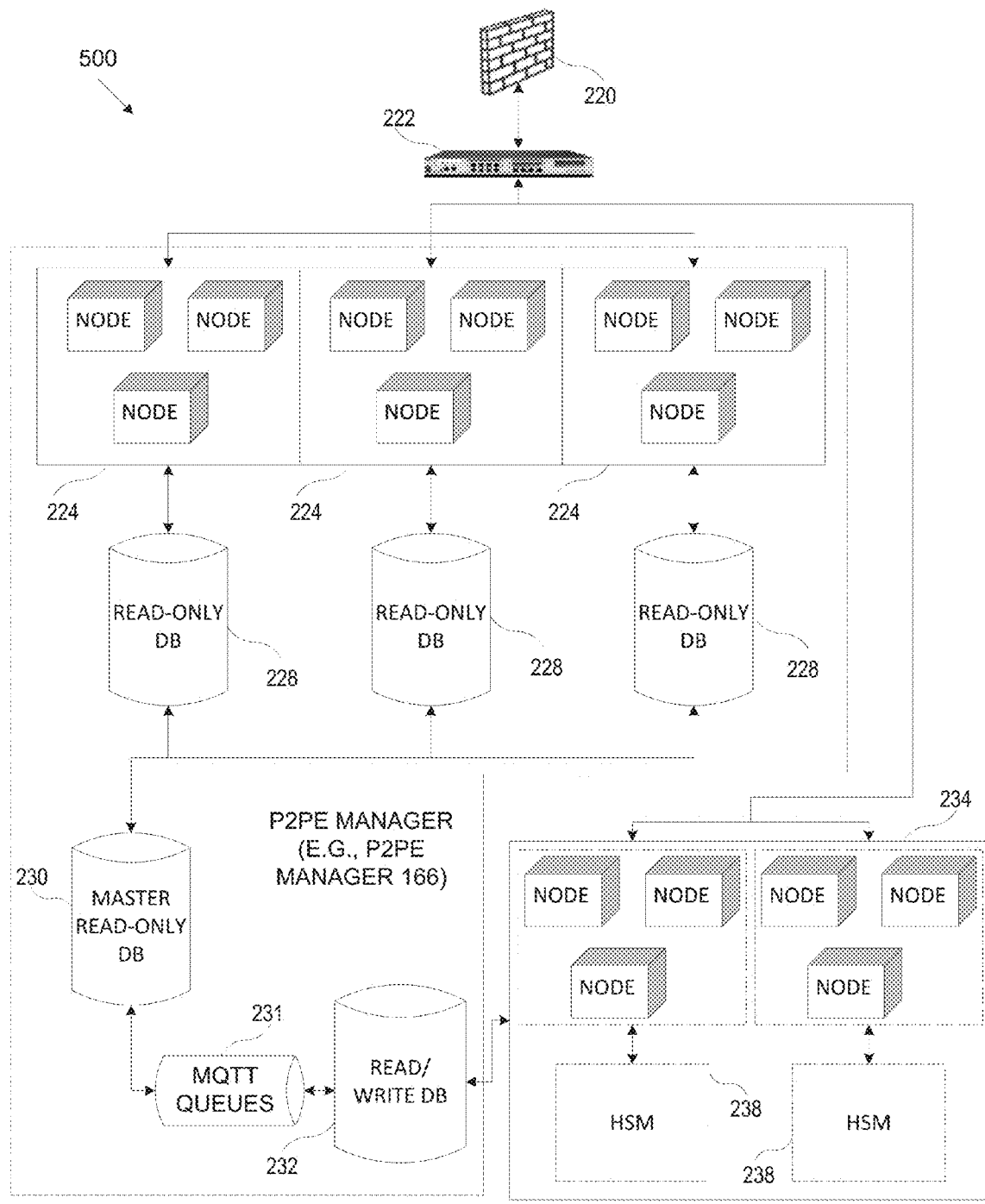
FIG. 2C ALTERNATIVE EXEMPLARY P2PE MANAGER SYSTEM ARCHITECTURE

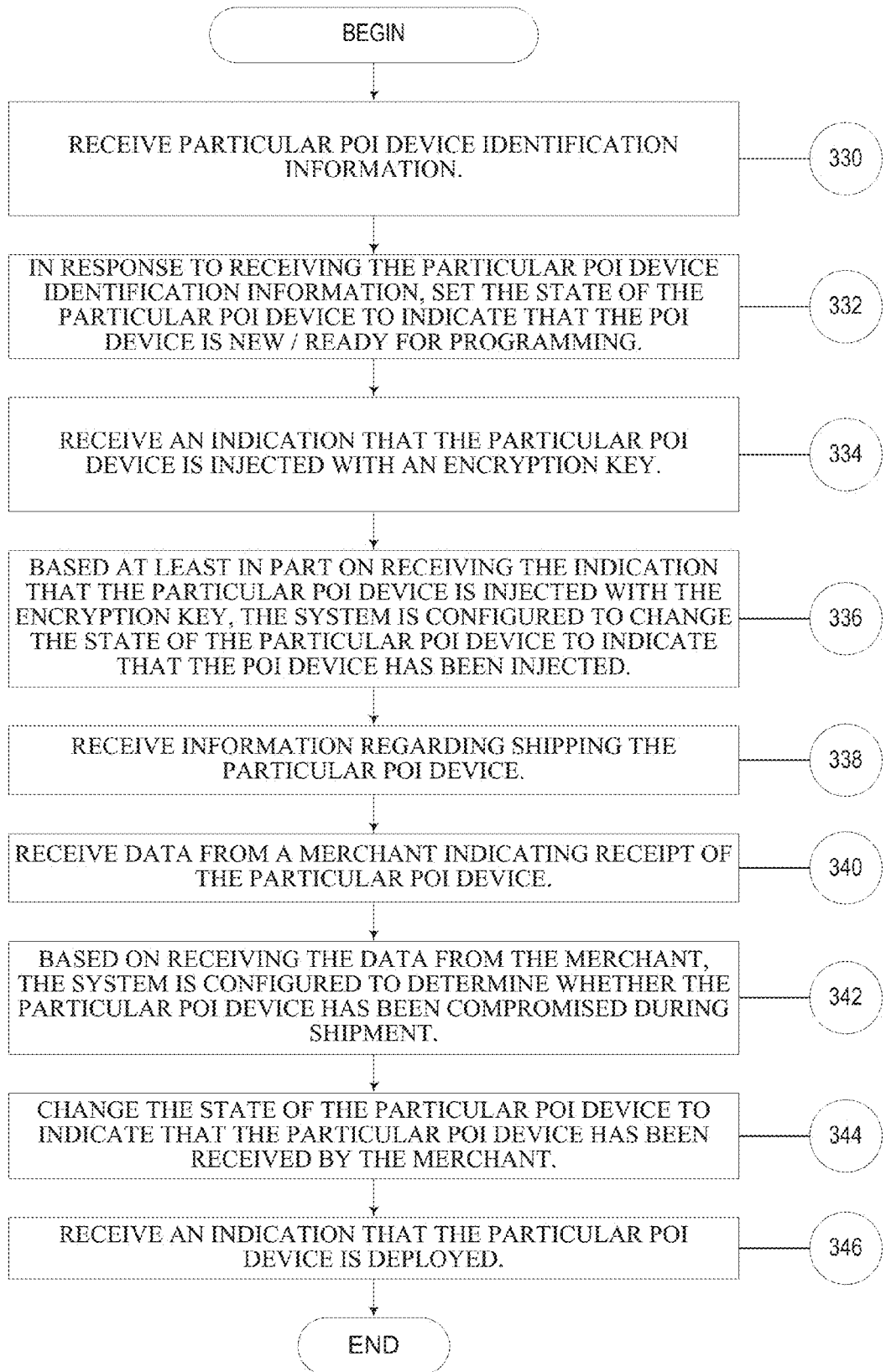
FIG. 3 EXEMPLARY POI HANDLING PROCESS

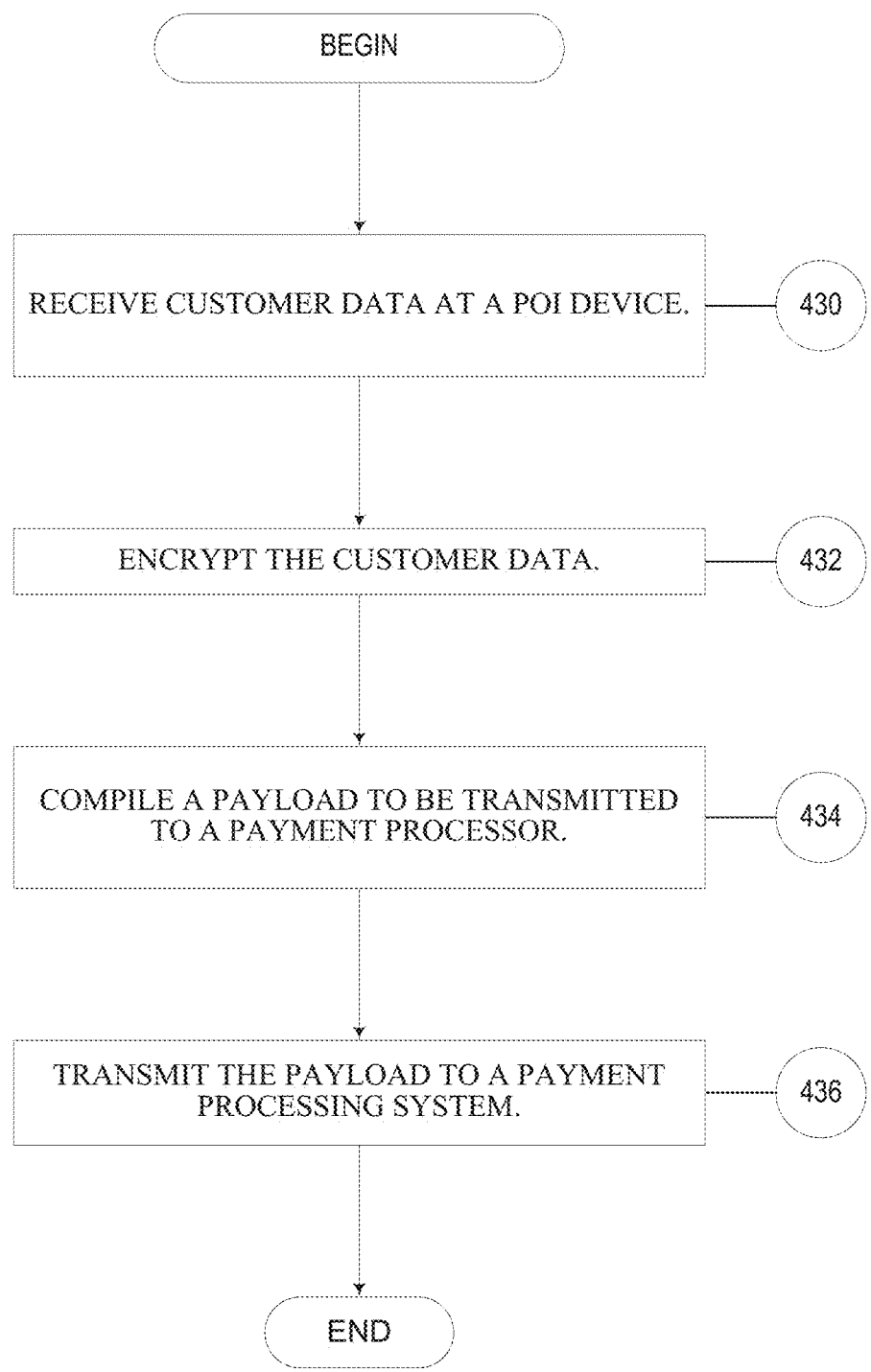
FIG. 4A  MERCHANT DATA PROCESS

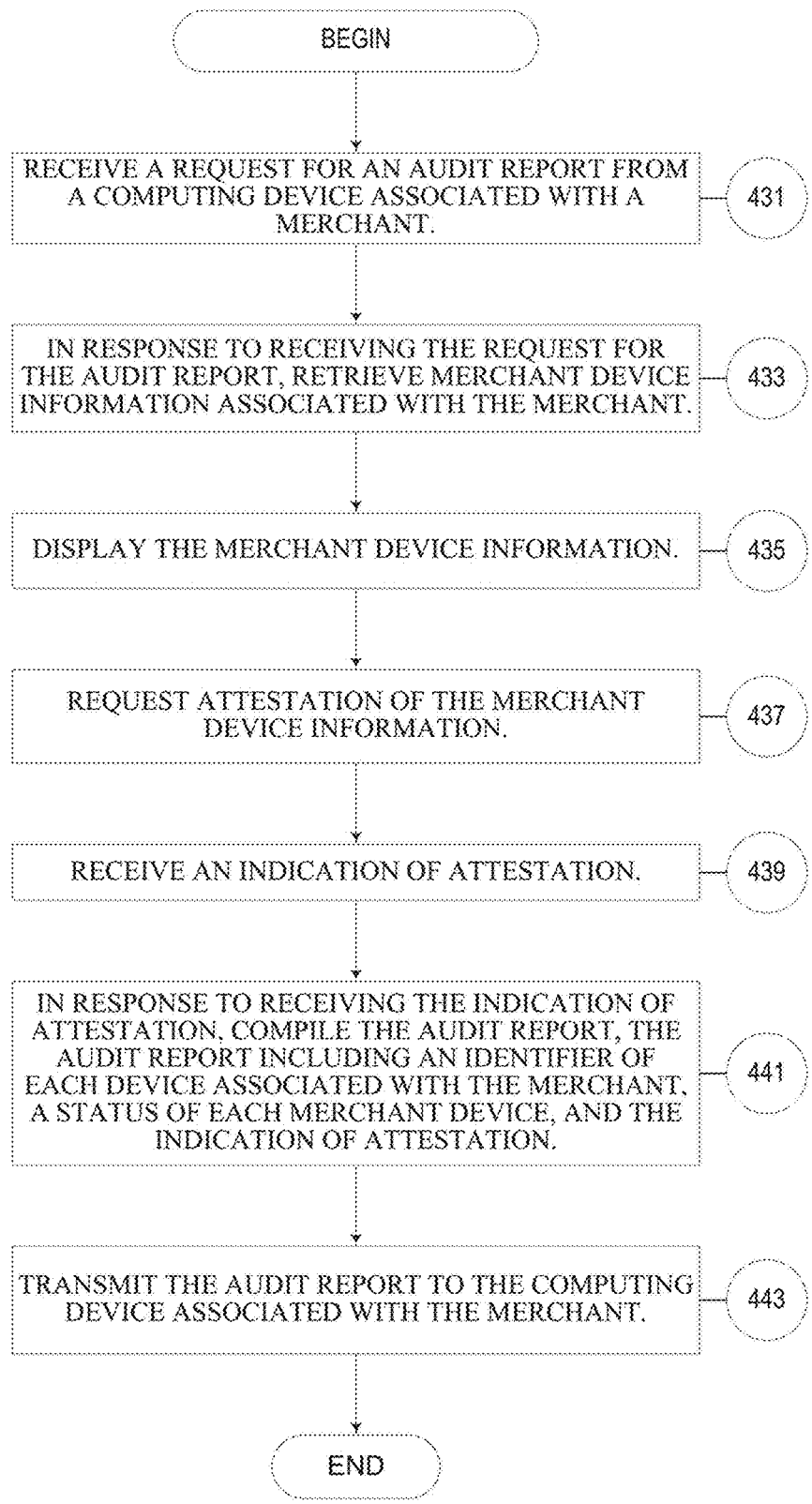
FIG. 4B  P2PE REPORT PROCESS

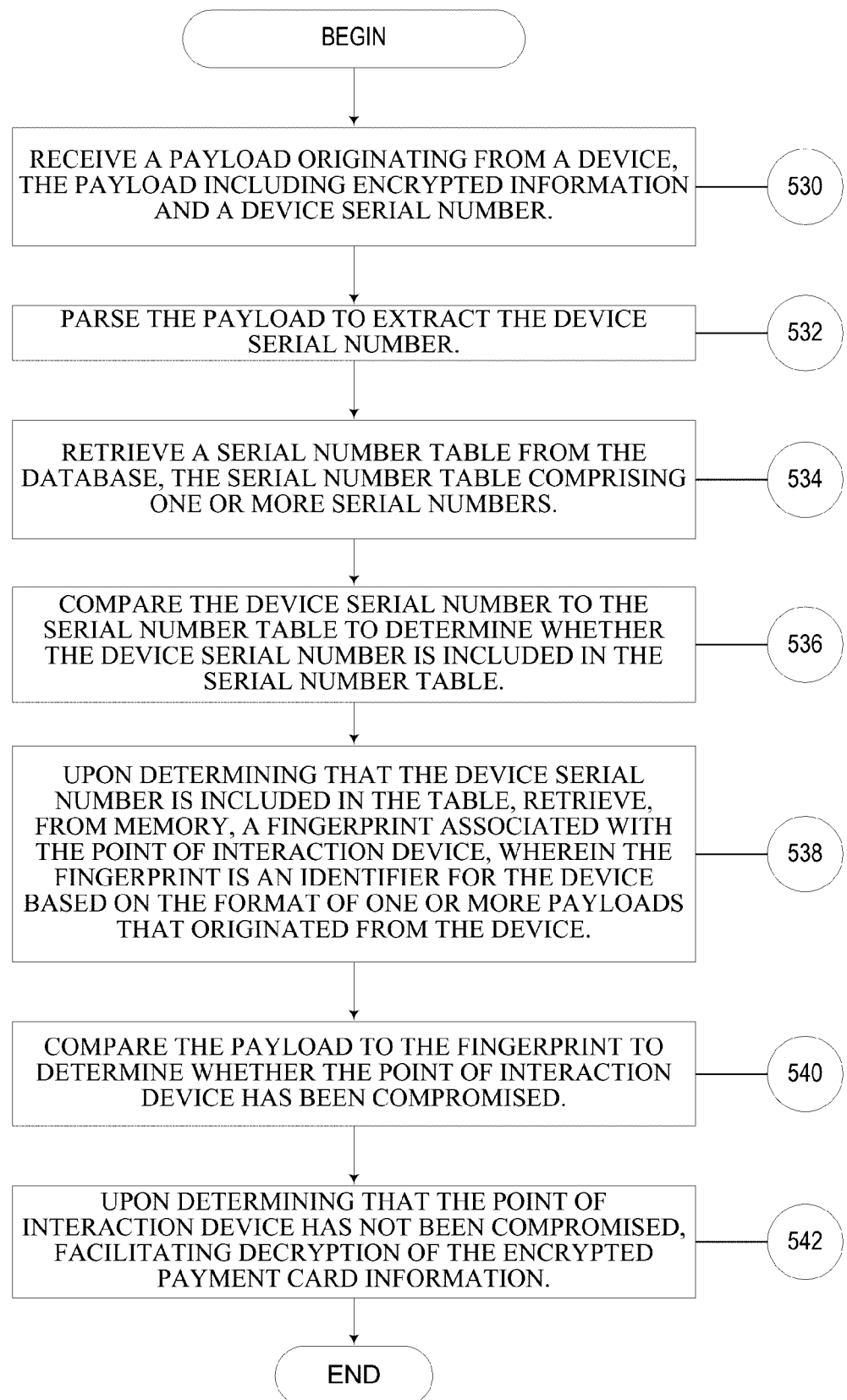
FIG. 5A EXEMPLARY DECRYPTION PROCESS

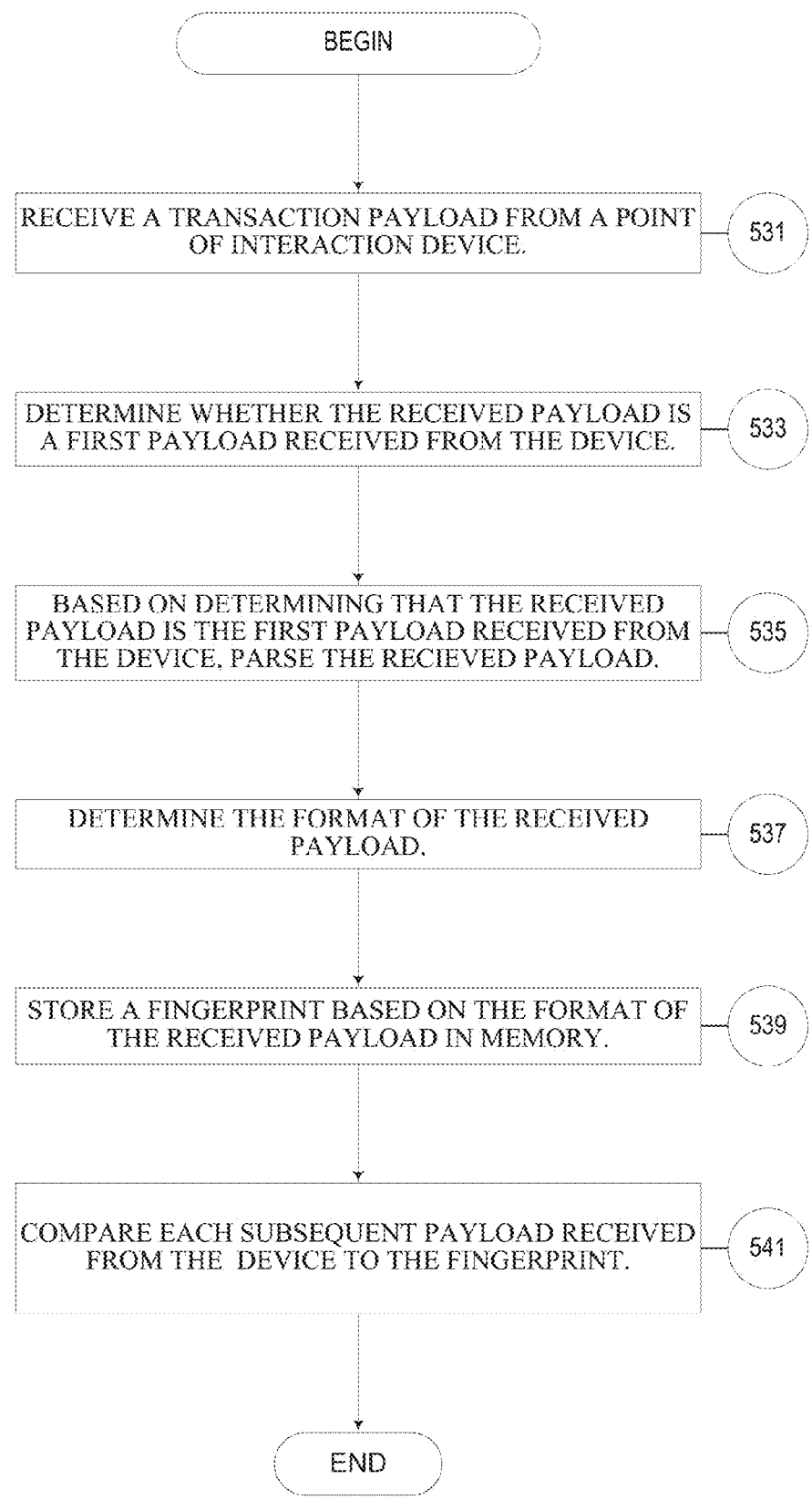
FIG. 5B  EXEMPLARY FINGERPRINT PROCESS

UML OF EXEMPLARY OUTPUT EVALUATION

UML OF EXEMPLARY CAPTURE DEVICE SEQUENCE

UML OF EXEMPLARY DEVICE SEQUENCE

UML OF EXEMPLARY FAILED COUNT SEQUENCE

UML OF EXEMPLARY HSM KEY INDEX SEQUENCE

UML OF EXEMPLARY UPDATE KEY INDEX SEQUENCE

UML OF EXEMPLARY VALIDATION SEQUENCE

UML OF EXEMPLARY P2PE EXCEPTION SEQUENCE

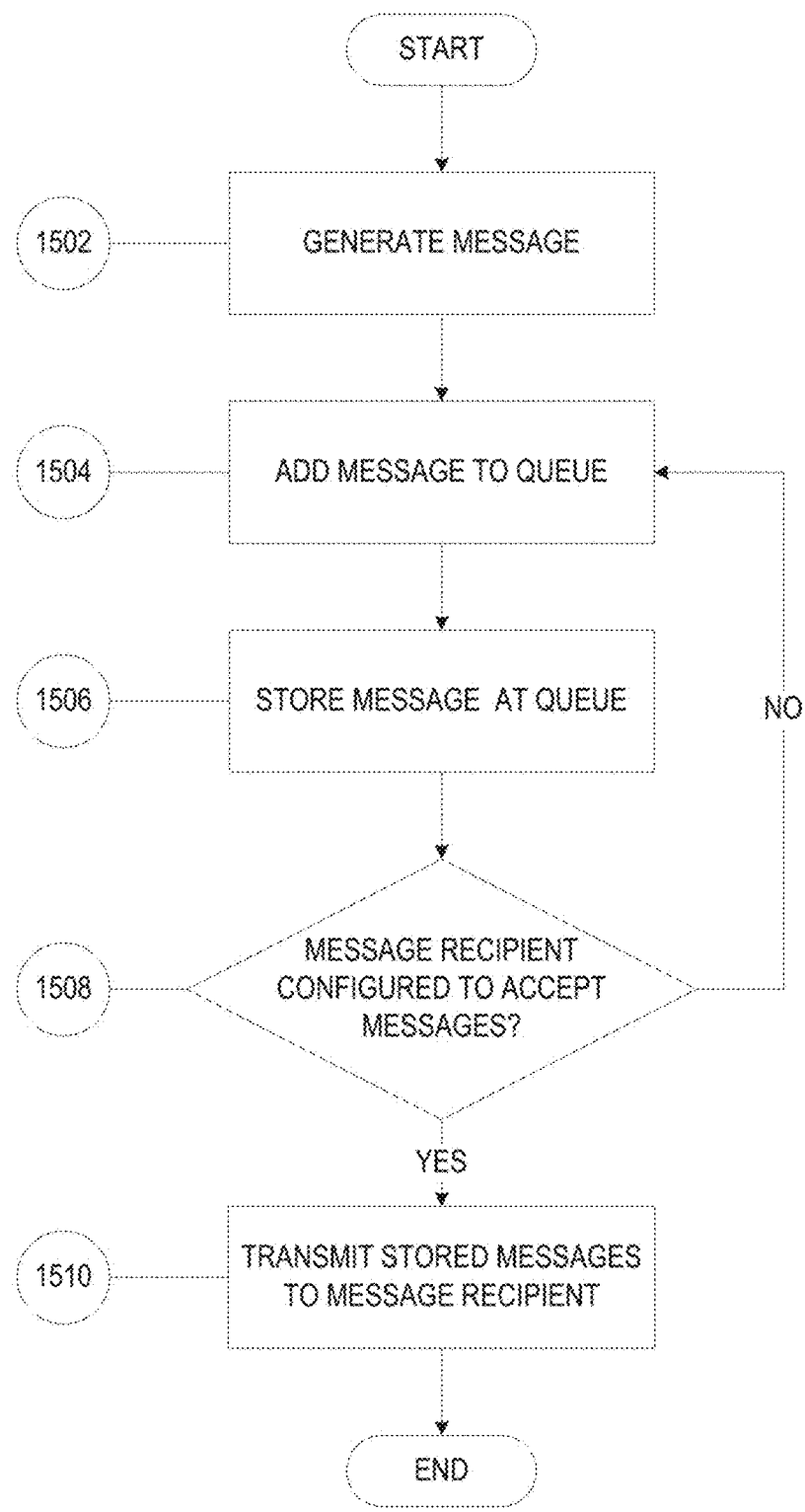
FIG. 15 *EXEMPLARY QUEUING PROCESS*

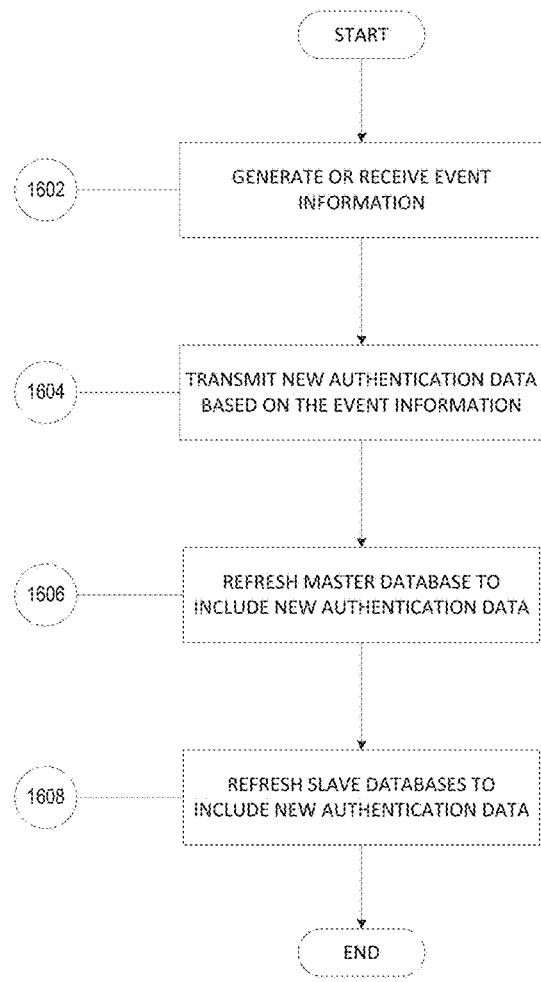
FIG. 16 EXEMPLARY UPDATE PROCESS

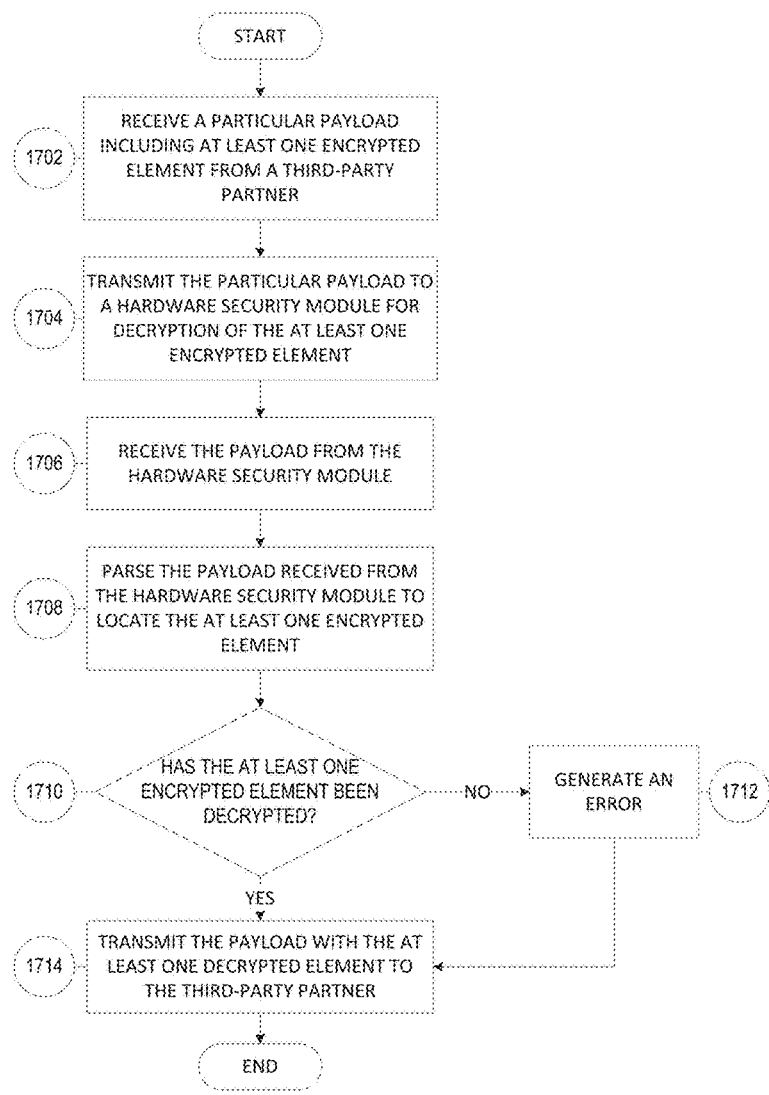
FIG. 17 *EXEMPLARY DECRYPTION VERIFICATION PROCESS*

SYSTEMS AND METHODS FOR DECRYPTION AS A SERVICE

CROSS-REFERENCE TO RELATED APPLICATIONS

This application claims the benefit under 35 U.S.C. §119 of and incorporates by reference herein in its entirety U.S. Provisional Patent Application No. 61/955,739, filed Mar. 19, 2014, entitled, "Systems and Methods of Point of Interaction Management" and is a continuation-in-part of, and incorporates by reference in their entireties, the following U.S. and international (PCT) applications:

U.S. patent application Ser. No. 14/591,223, filed Jan. 7, 2015, entitled "Systems and Methods for Creating Fingerprints of Encryption Devices;"

U.S. patent application Ser. No. 14/591,171, filed Jan. 7, 2015, entitled "Systems and Methods for Facilitating Decryption of Payloads Received from Encryption Devices;"

U.S. patent application Ser. No. 14/591,218, filed Jan. 7, 2015, entitled "Systems and Methods for Creating and Tracking States of Encryption Devices;" and International Patent Application No. PCT/US2015/010405, filed Jan. 7, 2015 entitled "Systems and Methods for Creating Fingerprints of Encryption Devices."

TECHNICAL FIELD

The present disclosure relates generally point to point encryption (P2PE) and management of point to point encryption systems.

BACKGROUND

Protecting cardholder data during an electronic payment transaction is vital for all entities involved in the processing of that transaction. It was recently made public that in the fourth quarter of 2013 and throughout 2014, significant data breaches occurred at major national retailers. In each instance, cardholder account numbers, and associated cardholder personal data, were illegally obtained by malicious fraudsters, exposing millions of sensitive payment records to potential fraudulent use, including identity theft. As a result, each retailer experienced damages in terms of lost sales, fines, and potential lawsuits for alleged negligence with regard to payment security standards. Another serious consequence of such breaches is brand erosion.

Data breaches are not a new occurrence in the payments industry, but the increasing number of breaches that occur each year, their severity in terms of numbers of records obtained, and the speed and stealth with which such breaches occur is new.

It is not a matter of if a business will experience a breach, it's a matter of when. While it is impossible to eliminate the possibility of a data breach occurring, it is now possible to protect cardholder data integrity in the event of a breach through PCI-validated point-to-point encryption (P2PE). PCI-validated P2PE renders any potential cardholder data useless and void of value in the event of a data theft because the cardholder data cannot be decrypted.

BRIEF SUMMARY OF THE DISCLOSURE

In various embodiments, the systems and methods herein include a point to point encryption management system configured to receive information from a plurality of point of interaction devices, the point to point encryption management system including a) a database for storing device information and b) at least one processor operatively coupled to the database, the at least one processor configured for: 1) receiving a payload originating from a point of interaction device, the payload including encrypted payment information and a device identifier; 2) parsing the payload to extract the device identifier, 3) retrieving an identifier table from the database, the identifier table including one or more device identifiers received by the point to point encryption management system; 4) comparing the device identifier to the identifier table to determine whether the device identifier is included in the identifier table; and 5) upon determining that the device identifier is included in the identifier table, facilitating decryption of the encrypted payment information.

According to particular embodiments, the systems and methods herein include a point to point encryption management system configured to receive information from a plurality of point of interaction devices, the point to point encryption management system including a) a database for storing device information and b) at least one processor operatively coupled to the database, the at least one processor configured for: 1) receiving a payload originating from a point of interaction device, the payload including encrypted data and a device serial number; 2) parsing the payload to extract the device serial number; 3) retrieving a serial number table from the database, the serial number table including one or more serial numbers received by the point to point encryption management system; 4) comparing the device serial number to the serial number table to determine whether the device serial number is included in the serial number table; 5) upon determining that the device serial number is included in the table, retrieving, from memory, a fingerprint associated with a record of the point of interaction device, wherein the fingerprint is an identifier created by the point to point encryption management system for the point of interaction device based on the format of one or more payloads that originated from the point of interaction device; 6) comparing the payload to the fingerprint to determine whether the point of interaction device has been compromised; and 7) upon determining that the point of interaction device has not been compromised, facilitating decryption of the encrypted payment card information.

In one or more embodiments, the systems and methods herein include a computer-implemented method for decrypting encrypted data, the computer-implemented method including: A) providing at least one encryption device including at least one processor configured to transmit encrypted data and a device serial number; and B) providing an encryption management system configured to receive information from the encryption device and at least one computer terminal located at a key injection facility, the encryption management system including a) a database for storing device information and b) at least one processor operatively coupled to the database, the at least one processor configured for: 1) receiving an initial device serial number from the at least one terminal located at the key injection facility; 2) writing the initial device serial number to a table in memory and storing the table in a database; 3) receiving a payload at least partially originating from the encryption device, the payload including encrypted data and the device serial number; 4) parsing the payload to extract the device serial number; 5) retrieving the table from the database; 6) comparing the device serial number to the initial device serial number to determine whether the device serial number is included in the table; and 7) upon determining that the device serial number and the initial device serial number are the same serial number, facilitating decryption of the encrypted data.

According to some embodiments, the systems and methods herein include a computer system for point to point encryption of payment transactions, the computer system including: A) at least one point of interaction device including a) one or more magnetic read heads for reading consumer payment cards and b) at least one processor configured to transmit consumer payment card information and a device serial number associated with the at least one point of interaction device; B) a hardware security module configured for decryption of payment card information; and C) a point to point encryption management system configured to receive information from the point of interaction device and at least one computer terminal located at a key injection facility, the point to point encryption management system including a) a database for storing device information and b) at least one processor operatively coupled to the database, the at least one processor configured for: 1) receiving an initial device serial number from the at least one computer terminal located at the key injection facility; 2) writing the initial device serial number to a table in memory and storing the table in the database; 3) receiving a first payload originating from the point of interaction device, the first payload including first encrypted payment card information and the device serial number, 4) parsing the payload to extract the device serial number; 5) retrieving the table from the database; 6) comparing the device serial number to the initial device serial number to determine whether the device serial number is included in the table; 7) upon determining that the device serial number and the initial device serial number are the same serial number: i) facilitating decryption of the payment card information; and ii) creating a fingerprint for the point of interaction device based on the format of the first payload and storing the payload identifier in memory; 8) receiving a second payload originating from the point of interaction device including encrypted second payment card information and the device serial number, 9) parsing the received second payload to extract the device serial number, 10) retrieving the table from the database; 11) comparing the device serial number to the initial device serial number to determine whether the device serial number is included in the table; 12) upon determining that the device serial number and the initial device serial number are the same serial number, retrieving the fingerprint; 13) comparing the second payload to the fingerprint to determine whether the point of interaction device has been compromised; and 14) upon determining that the point of interaction device has not been compromised, transmitting the second payment information to the hardware security module for decryption.

In at least one embodiment, the systems and methods herein include a computer system decrypting payment transactions, the computer system including: A) at least one point of interaction device including one or more processors configured to transmit consumer payment card information and a device serial number associated with the at least one point of interaction device; and B) a point to point encryption management system configured to receive information from the point of interaction device and at least one computer terminal located at a key injection facility, the point to point encryption management system including a) a database for storing device information and b) at least one processor operatively coupled to the database, the at least one processor configured for: 1) receiving an initial device serial number from the at least one computer terminal located at the key injection facility; 2) writing the initial device serial number to a table in memory and storing the table in the database; 3) receiving a payload at least partially originating from the point of interaction device, the payload including encrypted payment card information and the device serial number; 4) parsing the payload to extract the device serial number; 5) retrieving the table from the database; 6) comparing the device serial number to the initial device serial number to determine whether the device serial number is included in the table; and 7) upon determining that the device serial number and the initial device serial number are the same serial number, facilitating decryption of the payment card information.

In further embodiments, the systems and methods herein include a computer-implemented method for decrypting payment transactions, the method including: 1) providing at least one point of interaction device including one or more processors configured to transmit consumer payment information and a device serial number associated with the at least one point of interaction device; 2) providing a point to point encryption management system configured to receive information from the point of interaction device, the point to point encryption management system including a) a database for storing device information and b) at least one processor operatively coupled to the database; 3) receiving, by the least one processor, an initial device serial number at least one computer third party computing device; 4) writing, by the least one processor, the initial device serial number to a table in memory and storing the table in the database; 5) receiving, by the at least one processor, a payload at least partially originating from the point of interaction device, the payload including encrypted payment information and the device serial number; 6) parsing, by the at least one processor, the payload to extract the device serial number, 7) comparing, by the at least one processor, the device serial number to the initial device serial number to determine whether the device serial number and the initial serial number are the same serial number; and 8) upon determining that the device serial number and the initial device serial number are the same serial number, facilitating decryption of the payment information.

According to various embodiments, the systems and methods herein include a computer system for creating a fingerprint for a device, the computer system including the device operatively connected to a device management system, the device management system including at least one processor operatively coupled to at least one database, the at least one processor configured for: 1) receiving a first payload from the device, the first payload including data in a particular format and a device indicator, the device indicator including a unique identifier used for identifying the device; 2) creating the fingerprint for the device, the fingerprint including a section format for each of one or more distinct sections of the particular format in a particular order; 3) storing a record of the fingerprint for the device and the unique identifier at the at least one database; and 4) comparing a format of each subsequent payload received from the device to the fingerprint for the device to determine whether the device has been compromised.

In particular embodiments, the systems and methods herein include a computer system for creating a fingerprint for a device, the computer system including the device operatively connected to a device management system, the device management system including at least one processor operatively coupled to at least one database, the at least one processor configured for: 1) receiving payloads from a particular device, each payload including encrypted and unencrypted data in a format; 2) comparing the format of each payload from the particular device to the fingerprint associated with the particular device; and 3) upon determining that the format of a particular payload of the payloads received from the particular device does not match the fingerprint associated with the particular device, declining to decrypt the encrypted data of the particular payload and transmitting a notification of declining to decrypt the encrypted data to a user computing system associated with a user.

According to one or more embodiments, the systems and methods herein include a computer-implemented method for creating a fingerprint for a device, the method including: A) providing a device capable of encrypting data; B) providing a computer system operatively coupled to the device, the computer system including: 1) a decrypting means for decrypting data received from the device; 2) a fingerprint creation means for creating a fingerprint associated with the device; 3) at least one database; and 4) at least one processor operatively coupled to the decrypting means, the fingerprint creation means, and the at least one database; C) receiving, by the at least one processor, a first payload from the device, the first payload including data in a particular format, a device indicator, and encrypted data, the device indicator including a unique identifier used for identifying the device; D) creating, by the fingerprint creation means, a fingerprint for the device, the fingerprint including a section format for each of one or more distinct sections of the particular format in a particular order; E) storing a record of the fingerprint for the device and the unique identifier at the at least one database and changing a state of the device to active by the at least one processor; F) comparing, by the at least one processor, a second particular format of a subsequent payload received from the device to the fingerprint for the device to determine whether the device has been compromised; and G) upon determining that the device has not been compromised, decrypting, by the decrypting means, encrypted data of the subsequent payload.

In at least one particular embodiment, the systems and methods herein include computer system for managing encryption device status changes including a P2PE management system including at least one processor and operatively connected to an encryption device, the at least one processor configured for changing a state of the encryption device based upon transactional information received from the encryption device, wherein changing the state of the encryption device based upon transaction information includes: 1) receiving a transaction payload from an encryption device, the transaction payload including transaction information and non-transaction information; 2) determining whether the transaction information is unencrypted; and 3) in response to determining that the transaction information is unencrypted, disabling the encryption device by changing a state of the encryption device to a tampered state.

In further embodiments, the systems and methods herein include a computer-implemented method for managing encryption device status changes, the method including the steps of: A) providing a P2PE management system including at least one processor and operatively connected to an encryption device; and B) changing, by the at least one processor, a state of the encryption device based upon transactional information received from the encryption device, wherein changing the state of the encryption device based upon transaction information includes: 1) receiving a transaction payload from an encryption device, the transaction payload including transaction information and non-transaction information; 2) determining whether the transaction information is unencrypted; and 3) in response to determining that the transaction information is unencrypted, disabling the encryption device by changing a state of the encryption device to a tampered state.

In still further embodiments, the systems and methods herein include a computer system for managing encryption device status changes including a P2PE management system including at least one processor and operatively connected to an encryption device, the at least one processor configured for: A) changing the state of the encryption device based on input from an operator; B) changing a state of the encryption device based upon transactional information received from the encryption device, wherein changing the state of the encryption device based upon transaction information includes: 1) receiving a first transaction payload from an encryption device, the first transaction payload including first transaction information and first non-transaction information; 2) upon receiving the first transaction payload from the encryption device, changing the state of the encryption device from the deployed state to an active state and facilitating decryption of the first transaction information; 3) receiving a second transaction payload from the encryption device, the second transaction payload including second transaction information and second non-transaction information; 4) determining whether the second transaction information is unencrypted; and 5) in response to determining that the second transaction information is unencrypted, disabling the encryption device by changing the state of the encryption device from the active state to a tampered state.

According to particular embodiments, the systems and methods herein include a system for decryption of payloads, the system comprising: a frontend server operatively connected to a read-only database, the frontend server configured for: a) receiving a plurality of payloads from one or more third parties, wherein each of the payloads includes at least one encrypted element; b) retrieving authentication data from the read-only database; c) comparing the authentication data with each of the plurality of payloads to determine whether one or more of the payloads of the plurality of payloads has been compromised; d) upon determining that one or more of the payloads of the plurality of payloads has not been compromised, transmitting the one or more payloads of the plurality of payloads to a hardware security module for decryption of the at least one encrypted element; the read-only database operatively connected to the frontend server and configured for storing read-only authentication data for use in determining whether payloads have been compromised; and the hardware security module operatively connected to the frontend server, the hardware security module configured for decrypting the one or more payloads of the plurality of encrypted payloads based on an encryption key and transmitting the decrypted one or more payloads to the one or more third parties.

In one or more embodiments, the systems and methods herein include a computer-implemented method for decryption of payloads, the method comprising: providing a frontend server operatively connected to a read-only database, the frontend server configured for: a) receiving a plurality of payloads from one or more third parties, wherein each of the payloads includes at least one encrypted element; b) retrieving authentication data from the read-only database; c) comparing the authentication data with each of the plurality of payloads to determine whether one or more of the payloads of the plurality of payloads has been compromised; d) upon determining that one or more of the payloads of the plurality of payloads has not been compromised, transmitting the one or more payloads of the plurality of payloads to a hardware security module for decryption of the at least one encrypted element; providing the read-only database operatively connected to the frontend server and configured for storing read-only authentication data for use in determining whether payloads have been compromised; and providing the hardware security module operatively connected to the frontend server, the hardware security module configured for decrypting the one or more payloads of the plurality of encrypted payloads based on an encryption key and transmitting the decrypted one or more payloads to the one or more third parties.

According to some embodiments, the systems and methods herein include a scalable system for fast decryption of payloads, the system comprising: at least one hardware security module operatively connected to one or more frontend servers and configured for decrypting encrypted elements of payloads; the one or more frontend servers configured to receive and authenticate payloads based at least in part upon retrieving authentication data from a particular read-only database of one or more read-only databases; the one or more read-only databases operatively connected to the one or more frontend servers, wherein the one or more read-only databases comprise the authentication data for authenticating payloads; a read-only master database operatively connected to the one or more read-only databases, the read-only master database configured to refresh the authentication data stored at the one or more read-only databases; and a backend read/write database for logging decryptions and authentications, the backend read/write database operatively connected to the at least one hardware security module and the read-only master database.

In at least one embodiment, the systems and methods herein include a system for fast decryption of one or more payloads, the system comprising a message queuing protocol operatively connected to a read-only database and a read/write database, the message queuing protocol configured for: receiving event notifications from a read-only database, wherein the event notifications each comprise one or more notifications regarding the authentication of one or more received payloads; queuing the event notifications received from the read-only database; and transmitting the event notifications to the read/write database upon determining that the read/write database is configured to accept event notifications.

In further embodiments, the systems and methods herein include a computer-implemented method for fast decryption of one or more payloads, the method comprising providing a message queuing protocol operatively connected to a read-only database and a read/write database, the message queuing protocol configured for: receiving event notifications from a read-only database, wherein the event notifications each comprise one or more notifications regarding the authentication of one or more received payloads; queuing the event notifications received from the read-only database; and transmitting the event notifications to the read/write database upon determining that the read/write database is configured to accept event notifications.

According to various embodiments, the systems and methods herein include a system for fast decryption of one or more payloads, the system comprising: a frontend server for receiving encrypted payloads; a plurality of read-only databases operatively connected to the frontend server; a master read-only database operatively connected to each of the plurality of read-only databases; and a read/write database operatively connected to the master database, the read/write database for transmitting event messages to the master read-only database, wherein the system is configured for: receiving event information at the read/write database; upon receiving the event information at the read/write database, automatically transmitting authentication data to the master read-only database, wherein the authentication data has been updated by the event information; refreshing the read-only master database to include the authentication data; and refreshing each of the plurality of read-only databases with authentication data matching the refreshed read-only master database, wherein the authentication data is for determining whether a payload has been transmitted by a tampered device.

In particular embodiments, the systems and methods herein include a computer-implemented method for fast decryption of one or more payloads, the method comprising the steps of: providing a frontend server for receiving encrypted payloads; providing a plurality of read-only databases operatively connected to the frontend server; providing a master read-only database operatively connected to each of the plurality of read-only databases; providing a read/write database operatively connected to the master database, the read/write database for transmitting event messages to the master read-only database; receiving event information at the read/write database; upon receiving the event information at the read/write database, automatically transmitting authentication data to the master read-only database, wherein the authentication data has been updated by the event information; refreshing the read-only master database to include the authentication data; and refreshing each of the plurality of read-only databases with authentication data matching the refreshed read-only master database, wherein the authentication data is for determining whether a payload has been transmitted by a tampered device.

According to one or more embodiments, the systems and methods herein include a system for decryption of one or more payloads, the system comprising: a hardware security module for decrypting encrypted elements of received payloads, the hardware security module operatively connected to at least one decryption server; the at least one decryption server, wherein the at least one decryption server is configured to: receive a particular payload, the particular payload comprising at least one encrypted element; transmit the particular payload to the hardware security module for decryption of the at least one encrypted element; upon receiving the particular payload from the hardware security module, parse the particular payload to determine whether the at least one encrypted element has been decrypted by the hardware security module; upon determining that the at least one encrypted element has not been decrypted by the hardware security module, transmit an error message to a read/write database operatively coupled to the frontend server.

In at least one particular embodiment, the systems and methods herein include a computer-implemented method for decryption of one or more payloads, the method comprising: providing a hardware security module for decrypting encrypted elements of received payloads, the hardware security module operatively connected to at least one decryption server; providing the at least one decryption server; receiving a particular payload, the particular payload comprising at least one encrypted element; transmitting the particular payload to the hardware security module for decryption of the at least one encrypted element; upon receiving the particular payload from the hardware security module, parsing the particular payload to determine whether the at least one encrypted element has been decrypted by the hardware security module; and upon determining that the at least one encrypted element has not been decrypted by the hardware security module, transmitting an error message to a read/write database operatively coupled to the frontend server.

BRIEF DESCRIPTION OF THE DRAWINGS

The accompanying drawings illustrate one or more embodiments and/or aspects of the disclosure and, together with the written description, serve to explain the principles of the disclosure. A number of the diagrams below are unified modeling language (UML) 2.5 Sequence Diagrams. UML sequence diagrams focus on the message interchange between the numbers of lifelines (aka individual participants). One of ordinary skill in the art will understand that UML diagrams are read from left to right and from the top to the bottom. See www.uml-diagrams.org/sequence-diagrams-combined-fragment.html for more information on UML diagrams.

FIG. 2A shows a block diagram of an exemplary architecture of the P2PE management system and payments environment of FIG. 1 according to one embodiment of the present systems and methods.

FIG. 2B shows a block diagram of an exemplary architecture of the P2PE management system of FIG. 2A according to one embodiment of the present systems and methods.

FIG. 2C shows a block diagram of an alternate exemplary architecture of the P2PE management system of FIG. 2A according to one embodiment of the present systems and methods.

FIG. 3 is a flow chart illustrating an exemplary point of interaction management process according to one embodiment of the present systems and methods.

FIG. 4A is a flow chart illustrating an exemplary merchant data process according to one embodiments of the present systems and methods.

FIG. 4B is a flow charts illustrating an exemplary P2PE report processes according to one embodiment of the present systems and methods.

FIG. 5A is a flow chart illustrating an exemplary decryption process according to one embodiment of the present systems and methods.

FIG. 5B is a flow chart illustrating an exemplary fingerprint process according to one embodiment of the present systems and methods.

FIG. 15 is a flow chart illustrating an exemplary queuing process according to one embodiment of the present systems and methods.

FIG. 16 is a flow chart illustrating an exemplary update process according to one embodiment of the present systems and methods.

FIG. 17 is a flow chart illustrating an exemplary decryption verification process according to one embodiment of the present systems and methods.

DETAILED DESCRIPTION

Figure 1:
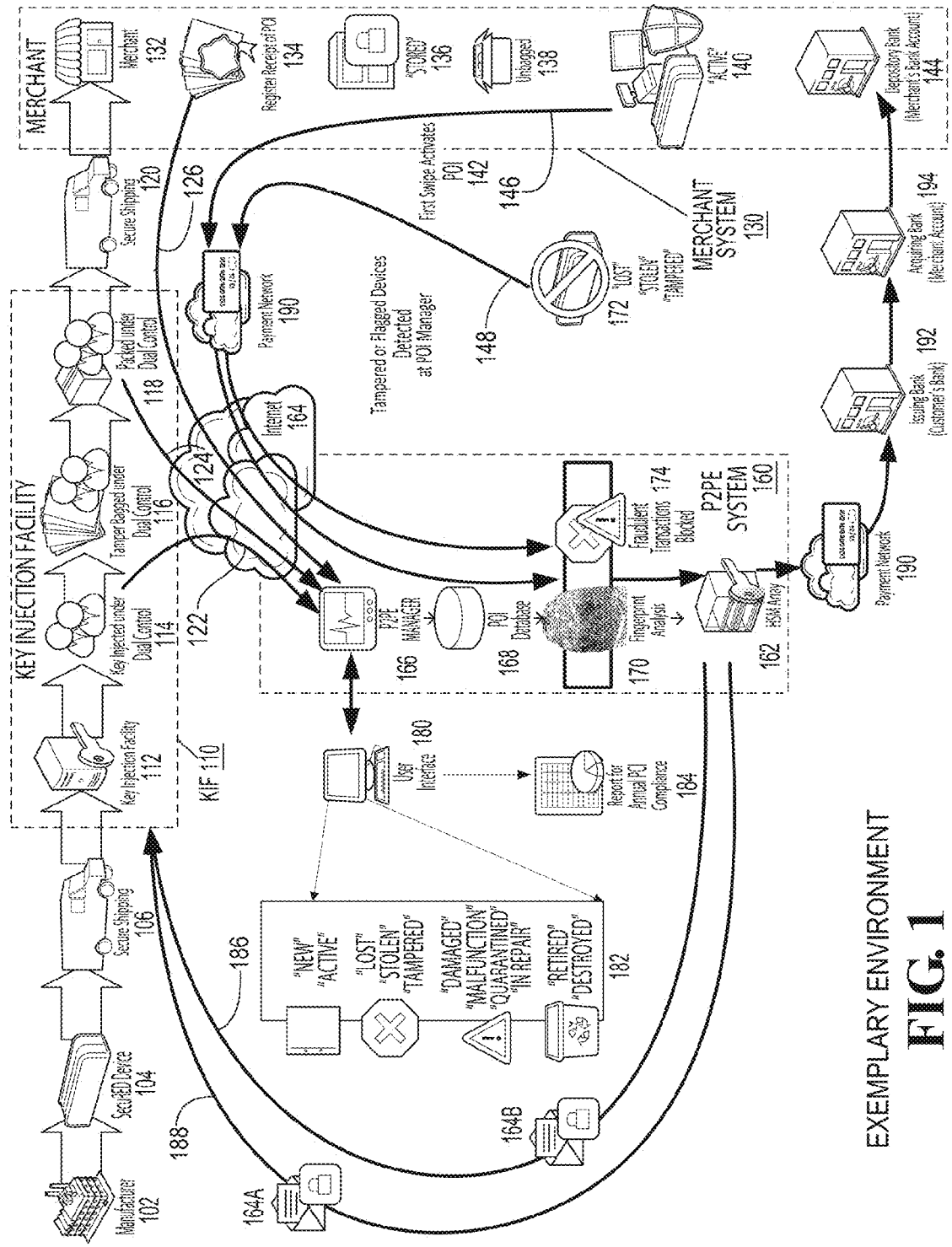
FIG. 1 is an exemplary point to point encryption (P2PE) management system and payments environment according to one embodiment of the present systems and methods.

For the purpose of promoting an understanding of the principles of the present disclosure, reference will now be made to the embodiments illustrated in the figures and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates.

Prior to a detailed description of the disclosure, the following definitions are provided as an aid to understanding the subject matter and terminology of aspects of the present systems and methods, are exemplary, and not necessarily limiting of the aspects of the systems and methods, which are expressed in the claims. Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

DEFINITIONS/GLOSSARY

Account Data: may refer to cardholder data and/or sensitive authentication data, such as, but not limited to a PAN, a routing number, a cardholder name, an expiration date, a service code, magnetic stripe data (or chip data), a card security code (e.g., CAV2, CVC2, CVV2, CID, etc.), one or more personal identification (PIN) numbers, and/or PIN blocks.

Bank: any suitable banking entity that may issue one or more cards (e.g., credit cards, debit cards, etc.) to a consumer, may receive deposits (e.g., from a merchant), manage accounts for customers, etc.

Fingerprint or Device Fingerprint: in various embodiments, a set of information used to identify a particular device, wherein the set of information may be based on the particular device's one or more attributes. In at least one embodiment, the set of information is for a POI Device and includes a serial number associated with the POI Device.

Hardware Security Module (HSM): a device that, in various embodiments, safeguards, houses, and manages digital encryption and decryption keys.

Key Injection Facility (KIF): a secure service facility that injects encryption keys (e.g., symmetric or asymmetric keys) into a device, typically a POI Device. The injected encryption key is used, in particular embodiments, to encrypt data (e.g., consumer data, such as PAN data) received by the POI Device.

Merchant: an entity that provides or sells goods and/or services to consumers and, in various embodiments, purchases, orders, and/or employs one or more POI Devices and utilizes the P2PE Manager.

P2PE Manager: in various embodiments, an application, software, hardware, and/or virtual machines for managing various state changes of a POI Device, for reporting state changes of a POI Device (or POI Devices), for determining decryption key index names, for authenticating third party partners and devices, and/or for providing reports for Merchants for compliance or other purposes.

P2PE Payload, Transaction Payload, or Payload: a bundle of information transmitted from a POI Device. A payload may include any variety of suitable information. As a non-limiting example, in particular embodiments, a payload includes consumer information, such as a card's PAN as well as a POI Device serial number. In various embodiments, a payload is sent to the P2PE Manager. In at least one embodiment, a payload is transmitted to a Payment Processor/Payment Network before decryption.

Payment Card Industry (PCI): generally, the debit, credit, prepaid, e-purse, e-wallet, ATM, and point of sale card industry and associated businesses.

Payment Processor/Payment Network: one or more entities (typically a third party) that processes payments (e.g., credit card transactions) for a Merchant.

PCI Security Council: a council originally formed by American Express, Discover Financial Services, JCB, MasterCard Worldwide, and Visa International for managing the PCI Data Security Standard. By meeting various PCI Security Council requirements, businesses can be deemed "PCI Compliant" or "PCI Validated."

PCI Validation/Validated (PCI Compliant): an entity may be deemed PCI Validated by meeting various criteria set forth by the PCI Security Council. PCI Validated companies and/or solutions may be listed by the PCI Security Council (e.g., on the PCI Security Council website or in other suitable locations).

Point of Interaction (POI) Device (Point of Entry Device): in various embodiments, a component of a point of sale system that enables a consumer to make a purchase at a Merchant, such as with a payment card. POI Devices may or may not be consumer-facing and may require a PIN number and/or other authentication. Non-limiting examples of POI Devices include magnetic card readers (e.g., for reading a payment card, such as a credit card) and near field communication (NFC) devices (e.g., for receiving a consumer's payment information from an electronic device, such as a mobile device). POI Devices may or may not be PCI Council approved devices.

Point to Point Encryption (P2PE): a combination of secure devices, applications, and processes that encrypt data from the point of interaction (for example, at the point of swipe) until the data reaches the solution provider's secure decryption environment.

Primary Account Number (PAN): an account number typically found on the front side of a payment card (e.g., a credit card number).

State(s): a recordable state and/or status of a particular device such as a POI Device. Various states and/or statuses may include "new," "active," "lost," "stolen," "tampered," "damaged," "malfunction," "quarantined." "in repair," "retired," and "destroyed."

State Changes: a recordable change in the state of a device, such as a POI Device. In a particular example, a POI Device state may be changed from "active" to "lost" based on various factors.

Overview

The present systems and methods relate generally to management of encryption processes, management of encryption devices, validation handling of encryption devices (including point-to-point encryption devices), and managing, assigning, and reporting state changes of encryption devices. According to particular embodiments, the present systems and methods track handling of decryption devices and their respective payloads (e.g., outputs of swipe data, etc.). It should be understood from the disclosure herein that the management of the encryption processes described herein may be, in some embodiments, PCI validated and compliant.

According to particular embodiments, the systems and methods herein are directed to secure encryption device handling. Particularly, the systems and methods herein are directed to: 1) receiving an indication of a state of a particular device; 2) receiving a payload from the particular device, including a device serial number and encrypted payload; 3) creating a record (e.g., a fingerprint) of the format of the payload and storing the record in memory; 4) receiving a second payload from the particular device, the second payload including the device serial number and a second encrypted payload; 5) retrieving the record of the format of the payload associated with the particular device from memory; 6) comparing the record of format of the payload to the format of the second payload; and 7) upon determining that that the format of the second payload does not match the record of the record of format of the payload, changing the state of the particular device to a tampered state.

In one or more aspects, the systems and methods herein are directed to facilitating decryption of encryption device payloads based on a device serial number included in the payload. In these aspects (and others), the system is configured to retrieve various information regarding the particular device from a database based on the device serial number. Such data may include, for example, a record of the format of a first payload of the particular device (as discussed above), a key index number indicating a base key used as the basis for encrypting a payload of the particular device, a state of the particular device, etc.

According to various aspects, the systems and methods herein are further directed to create a "fingerprint" of a particular device. Particularly, the system may be configured to create a fingerprint of the particular device to be used as a comparison to payloads received from the particular device to determine whether the particular device is compromised (e.g., the device has been stolen, hacked, etc.). The system may be configured to create the fingerprint of the particular device in any suitable way such as, for example, by parsing a first payload received from the particular device, determining the format of each segment of the first payload, recording the format of each segment of the first payload in an order of the payload.

In some aspects, the systems and methods herein are directed to creating reports regarding states and locations of encryption devices tracked by the system. In these aspects, the system is configured to receive a report request from a merchant, compile the report based on state information associated with encryption devices associated with the merchant, request that the merchant attest to the information included in the report, and provide the report to the merchant.

As will be understood by one of ordinary skill in the art, the systems and methods herein may be used by any suitable entity. Further, the systems and methods described herein may be utilized for any suitable encryption/decryption process, including, but not limited to, point-to-point encryption, encryption/decryption of medical data, encryption/decryption of social security numbers, etc. The following exemplary functionality of the systems and methods herein is included for the purpose of furthering understanding of the included systems and methods and is intended to be exemplary and non-limiting.

Exemplary P2PE Manager and Payments Functionality

Turing now to the figures, FIG. 1 depicts a high-level exemplary P2PE manager and payments environment and process. In general, FIG. 1 shows an exemplary path of an exemplary point of interaction (POI) device from a manufacturer (e.g., manufacturer 102) to a merchant (e.g., merchant 132) and the various processes and state changes associated with the exemplary POI device. FIG. 1 further depicts data received by the P2PE system 160, exemplary high level of data processing that occurs at the P2PE system, and an exemplary payment cycle.

FIG. 1 shows an exemplary P2PE manager and process wherein swipe (as will be understood by one of ordinary skill in the art, data may also be keyed into a user interface) data is sent from a merchant swipe terminal (e.g., a POI device) to a payment network, then to the P2PE system.

FIG. 1 depicts a manufacturer 102 of point of interaction (POI) devices (e.g., POI device 104). According to particular embodiments, manufacturer 102 produces POI device 104 in response to receiving a purchase order from a merchant or from a P2PE system (e.g., P2PE system 160). In various embodiments, manufacturer 102 produces POI device 104 (and any other POI devices) in any suitable way, as will be understood by one of ordinary skill in the art. In particular embodiments, manufacturer 102 produces POI devices designed to output a device serial number and information in a particular format, as will be further discussed herein.

POI device 104 may be any device suitable of receiving information from a consumer. In various embodiments, POI device 104 receives payment information, as discussed throughout this document, although it should be understood by one of ordinary skill in the art that POI device 104 should not be considered limited to only payment information.

POI device 104 may include any suitable components for receiving payment information (e.g., credit card magnetic strip information, payment information received from a mobile device, such as a smartphone, tablet, PDA, etc., chip information (e.g., from cards with embedded chips), payment information received from a check-out station, other sensitive information, such as medical records received from an electronic medical records system, etc.). In various embodiments, POI device 104 reads and/or receives payment information via a magnetic card reader for reading a card's magnetic strip (e.g., a credit card). In one or more embodiments, POI device 104 includes a pin-pad, biometric scanner (e.g., finger print or retina scanner), and/or chip reader for receiving secondary consumer identity-verification information. In at least one embodiment, POI device 104 is configured for receiving payment information via one or more radios, such as a near-field communications radio, a suitable wireless network connection radio, such as a Bluetooth, Bluetooth Low Energy (BLE), and/or Wi-Fi radio (e.g., POI device may receive payment information from an application (mobile wallet) included on mobile device via a "tap").

As will be further discussed herein, POI device 104 transmits information received from a consumer (e.g., payment information, biometric information, PIN information, etc.) to another system/device for processing. In various embodiments, POI device 104 is configured to encrypt received information upon receipt of said information. According to particular embodiments, POI device 104 transmits information received from the consumer with device information, such as a serial number associated with POI device 104 for identification of the POI device. In some embodiments, POI device 104 is configured to transmit the information received from the consumer and device information in a particular format, which may be used by a P2PE system (e.g., P2PE system 160) to form a "fingerprint" (e.g., an identifier based on the format and/or device information of POI device 104) for identifying transactions sent from POI device 104.

As will be understood by one of ordinary skill in the art, POI device 104 may be any POI device approved by the PCI Security Standards Council ("PCI SSC") or other suitable device for receiving information to be encrypted. Examples of PCI SSC-approved devices can be found on PCI SSC's website at https://www.pcisecuritystandards.orgapproved_companies_providers/approved_pin_transaction_security.php. In one or more embodiments, POI device 104 is a stand-alone swipe terminal, such as ID TECH's SecuRED™ SRED device. In some embodiments, POI device 104 is an all in one type mobile business solution, such as 4P Mobile Data Processing's FDA600-POS device. In at least one embodiment, the POI device 104 is a countertop terminal, such as Atos Worldline's Yomani device.

Still referring to FIG. 1, manufacturer 102 ships POI device 104 via secure shipping 106 to a key injection facility (KIF) 110. As will be understood by one of ordinary skill in the art, secure shipping 106 may represent any suitable type of secure shipping known in the art, including, but not limited to, via FedEx, UPS, etc. and/or by shipping via air, ground, rail, etc.

Once received by KIF 110, in one or more embodiments, information regarding POI device 104 is entered into P2PE manager 166. In various embodiments, the information regarding POI device 104 includes a device serial number (e.g., to be matched later to swipe transactions). In at least one embodiment, the information regarding POI device 104 includes a firmware version number. In further embodiments, the information regarding POI device 104 includes a date of manufacture, the name of the manufacturer (e.g., manufacturer 102), etc.

Information regarding POI device 104 may be entered into the P2PE manager 166 in any suitable way, such as, for example, by user interface 180 or via an API interface. In various embodiments, a KIF employee scans in a serial number associated with POI device 104 via a suitable scanning mechanism (e.g., a hand-held barcode scanner or the like). In some embodiments, a KIF employee keys in a serial number associated with POI device 104 via a keyboard (or other suitable key-entry device, such as a touch screen). As will be understood by one of ordinary skill in the art, POI device 104 may be processed via any suitable security protocol and information about POI device 104 may be entered into any suitable system, such as a separate KIF inventory management system.

As shown in FIG. 1, P2PE manager 166 may be operatively connected to user interface 180. User interface 180 may represent any number of user interfaces configured to interact with P2PE manager 166 and user interface 180 may be connected to P2PE manager 166 in any suitable way, such as via the Internet, LAN, WAN, Wi-Fi, etc. For example, user interface 180 may represent a user interface at KIF 110 used to input information regarding POI device 104 (as discussed above). Continuing with this example, user interface 180 may also represent a user interface at merchant 132 used to entered information regarding POI device 104 (e.g., when POI device 104 is received, to update the state of POI device 104, etc.). User interface 180, in this example, may represent a user interface at a third-party "Partner" (e.g., a hospital using an electronic medical records system or other entity wishing to encrypt and decrypt data). User interface 180 may be used to manually change the state of POI device 104 (e.g., from "Stored" to "Deployed") or view the state of POI device 104, as shown at 182. In some embodiments, user interface 180, via P2PE manager 166, may be configured to produce one or more reports 184 (as will be further discussed herein).

According to particular embodiments, once POI device 104 information is entered into P2PE manager 166, it is assigned a "state." The state of POI device 104 as indicated in P2PE manager 166 may be used to help ensure secure handling and chain of custody of POI device 104. For example, when first entered into the P2PE manager 166, POI device 104 is assigned a state of "New" in the P2PE manager 166. Once a key has been injected into POI device 104, the state may be changed to "Injected." Once received by a merchant (e.g., merchant 132), but not deployed/in use, POI device 104 may have a state of "Stored." Alternately, POI device 104 may be assigned a state of "DOA" (dead on arrival) if the device is damaged or non-functional. For example, P2PE manager 166 may be configured to discard, prohibit and/or block data (e.g., card swipe data), from a POI device that is listed in a "Tampered," "Dirty," or "Flagged" state to protect the system and/or the card swipe data.

Continuing with FIG. 1, POI device 104 is stored at KIF 110 in a secured inventory room. The inventory room may be secured in any suitable way, such as, but not limited to, dual access, by lock and key, or by any suitable security protocol.

According to particular embodiments, upon order from a merchant, POI device 104 is injected with one or more base derivation keys ("BDKs") and is securely bagged, tagged, and packed for secure shipment to the merchant (e.g., merchant 132). According to at least one embodiment, a hardware security module ("HSM") array produces encryption/decryption keys for encrypting data received by the POI device 104. As will be understood by one of ordinary skill in the art, an HSM array may be located at a KIF or at a remote location. In the embodiment shown in FIG. 1, KIF 110 and HSM array 162 are remote.

HSM array 162, shown in FIG. 1 as part of P2PE system 160, in various embodiments, creates a base derivation key (BDK), which is split into two parts, BDK 164A and BDK 164B for security purposes. BDK 164A and 164B are sent to KIF 110 (via two separate secure pathways 186 and 188) where they are received by two key part holders. BDK 164A and 164B may be sent to KIF 110 in any suitable manner, such as, for example, by courier, by mail, by fax, by email (encrypted or otherwise), etc. In particular embodiments, the two key part holders verify receipt of BDK 164A and BDK 164B via signature upon delivery, delivery receipt, etc.

In particular embodiments, the process continues with key assembly at step 114. The key assembly process is briefly described immediately below. However, it will be understood by one of ordinary skill in the art that this key assembly process is intended to be exemplary and any suitable key assembly process may be used. The first key part holder (e.g., the person with BDK 164A) enters the secured inventory room storing POI device 104 and enters BDK 164A into a tamper resistant security module ("TRSM"). The first key part holder leaves the secured inventory room. The second key part holder (e.g., the person with BDK 164B) enters the secured inventory room (e.g., after the first key part holder has exited the secured inventory room) and enters BDK 164B into the TRSM. According to particular embodiments, a third party separately validates the entries of the first key part holder and the second key part holder (e.g., via a key serial number (KSN) and check digit). Upon authentication of the key parts, the TRSM produces a cryptogram representing the (assembled) BDK 164 and transfers the cryptogram to a smart card. POI device 104 (and each POI device) is injected with a unique Initial Key derived from the BDK (e.g., from the smart card). As discussed herein, once POI device 104 is injected with the encryption key, its state in the P2PE manager 166 may be changed to "Injected" via transmission 122.

Still referring to FIG. 1, at step 116, POI device 104 is placed in a tamper evident bag and the bag is sealed with a tamper evident, serialized sticker. POI device 104 (in the tamper evident bag and sealed with the serialized sticker) is then, at step 118, sealed in a box (e.g., any suitable shipping container) for shipment to merchant 132 and given a tracking number. According to particular embodiments, the serial number on the serialized sticker and the tracking number for the shipment of POI device 104 is entered into P2PE manager 166 via transmission 124 and associated with the record for POI device 104 in P2PE manager 166 for later verification by merchant 132 upon receipt of POI device 104. In various embodiments, once a tracking number is entered into P2PE manager 166, the state associated with POI device 104 may be changed.

At step 120, POI device 104 is securely shipped to merchant 132. POI device 104 may be securely shipped to merchant 132 in any suitable way, including by FedEx, UPS, USPS, etc. by air, ground, rail, etc.

Merchant 132 receives POI device 104 and registers receipt of POI device 104 with P2PE manager 166 as shown at step 134 via transmission 126. In various embodiments, upon receipt of POI device 104, merchant 132 confirms that the tamper evident bag (see above) and the serialized sticker used to pack POI device 104 have not been tampered with. In particular embodiments, merchant 132 enters the serial number of POI device 104 (as printed on the outside of the shipping box or in some other location) and the serial number of the serialized sticker into P2PE manager 166. In one or more embodiments, the state associated with POI device 104 is changed to "Stored" in P2PE manager 166. Merchant 132 stores POI device 104 (in the tamper evident bag) until deployment.

At step 138, merchant 132 removes POI device 104 from the tamper evident bag for deployment. In various embodiments, merchant 132 changes the state of POI device 104 to "Deployed" in P2PE manager 166. It will be understood that, in various embodiments, P2PE manager 166 substantially automatically changes the state of POI Device 104 to "Deployed" based on receiving information (e.g., that the POI device 104 has been removed from the tamper evident bag).

At step 140, POI device 104 is deployed (e.g., connected a cash register, etc.) to accept payment card information. As further discussed herein. POI device 104 may be configured to accept any payment (or other) information, but for the purposes of simplicity and brevity, payment card information in the form of magnetic card swipe data will be discussed in regards to FIG. 1.

Upon receiving magnetic card swipe data (e.g., a first or initial card swipe), in various embodiments, POI device 104 substantially automatically encrypts the magnetic card swipe data based on the encryption key injected into POI device 104 at step 114 above. In various embodiments, POI device 104 is configured to encrypt the swipe data immediately after receiving the swipe data. In particular embodiments, POI device 104 may receive swipe data in any suitable way, including, via magnetic read heads (if a credit/debit card with a magstripe is swiped), via a chip and pin reader, via near-field communications, etc.

In FIG. 1, according to particular embodiments, upon receiving and encrypting swipe data, POI device 104 is configured to transmit the swipe data and other information (collectively, a "payload") to payment network 190. According to particular embodiments, POI device 104's payload includes, in addition to the swipe data, a serial number associated with POI device 104 (e.g., the serial number assigned to POI device 104 by manufacturer 102 and recorded in P2PE manager 166 at KIF 110). In some embodiments, POI device 104's payload includes other information including PIN information, biometric information (e.g., POI device includes or is connected to one or more biometric readers, such as a finger print scanner), chip information, etc. It will be understood by one of ordinary skill in the art that a POI device payload path as shown in FIG. 1 is merely exemplary and a POI device payload may be routed through one or more entities and/or via pathways not shown in FIG. 1.

At step 142, in response to receiving its first card swipe, POI device 104 transmits its first payload to payment network 190, which forwards the payload to P2PE manager 166 for verification and decryption of the swipe data via internet 164 and transmission 146. In particular embodiments, upon receipt of the first payload from POI device 104, P2PE manager 166 is configured to parse the first payload of POI device 104 and extract the serial number of POI device 104. In some embodiments, P2PE manager 166 then compares the extracted serial number of POI device 104 to a table of POI device serial numbers to determine whether POI device 104 is included in the table. In other words, in certain embodiments, P2PE manager 166 is configured to determine whether POI device 104 is a recognized device based on its serial number that is sent to P2PE manager 166 with each transaction payload.

Upon determining that POI device 104's serial number is included in P2PE manager 166, P2PE manager 166 may be configured to check the state associated with POI device 104. If, for example, POI device 104 has a state of "Deployed" in P2PE manager 166, upon successfully receiving the first swipe transaction, P2PE manager 166 may change the state of POI device 104 to "Active." An "Active" state in P2PE manager 166 generally denotes a state of securely receiving decrypted swipe transactions.

If, as another example, POI device 104 has a state of "Tampered" or "Stolen" or "Lost" in P2PE manager 166, P2PE manager 166 may be configured to discard the received payload and/or report the receipt of a payload from a POI device that is not listed as "Active" or "Deployed" to merchant 132 or any other suitable party and not process the encrypted swipe data (e.g., included in the payload). It should be understood based on discussions herein that the system can help detect fraudulent transactions based at least in part on the various states of P2PE manager 166. An exemplary list of state changes is shown at 182 in FIG. 1 and will be further discussed herein.

Continuing with the example shown in FIG. 1 wherein P2PE manager 166 has received a first payload from POI device 104, P2PE manager 166 creates a "fingerprint" to be associated (in memory) with POI device 104 at step 170. According to particular embodiments, the fingerprint for POI device 104 is created by parsing the payload sent by POI device 104 and recording the format, order, and number of data items included in the payload (e.g., opposed to the contents of the payload) and/or any firmware versions of software running on POI device 104. Exemplary fingerprint creation processes will be further discussed herein (e.g., at FIG. 4A). In various embodiments, the fingerprint is stored and used in future transactions to verify that data received from POI device 104 is secure (e.g., that POI device 104 has not been tampered with and/or is not malfunctioning).

According the embodiment shown in FIG. 1, after the fingerprint analysis 170, P2PE manager 166 transmits the first payload from POI device 104 to HSM 162 for decrypting (e.g., using BDK 164). Once the payload is decrypted, the swipe data is re-encrypted to an encryption that can be decrypted by other entities in the payment process. Once the payload is re-encrypted, it is transmitted to a payment network 190 where the swipe data (e.g., credit card information) is processed and sent on to an issuing bank 192 (money is debited from the consumer's account associated with the swiped card), acquiring bank 194, and finally to a depository bank 144 where money is deposited to the merchant (e.g., merchant's bank account).

In particular embodiments, the system operates essentially in the same way each time a payload is received from POI device 104 while the state associated with POI device 104 is "Active" (e.g., POI device 104 regularly receives swipe transactions). For example, a customer of merchant 132 swipes their credit card at POI device 104. POI device 104 transmits its payload, including POI device 104 serial number and encrypted swipe data to P2PE manager 166. Continuing with this example, P2PE manager 166 determines the serial number of the received payload (e.g., POI device 104's serial number) and looks up corresponding fingerprint information associated with POI device 104's serial number to verify that POI device 104 has not been tampered with at step 170. Once POI device 104's fingerprint has been verified, in this example, HSM 162 decrypts POI device 104's payload and then re-encrypts the swipe data and sends it on to the payment network 190, issuing bank, 192, acquiring bank 194, and depository bank 144 to complete the payment process.

Continuing with FIG. 1, if POI device 104 is tampered with (e.g., in an attempt to steal consumer data), P2PE manager 166 is configured to block fraudulent transactions by not passing payloads to HSM 162 for decryption as shown in step 174. There are a number of ways that P2PE manager 166 may determine that POI device 104 has been tampered with and refuse to pass the payload on to HSM 162 for decryption. In a particular embodiment, P2PE manager 166 may receive a payload from POI device 104 that does not match the fingerprint associated with POI device 104 (e.g., the format of the payload has changed, the version number of the firmware used by the device has changed, etc.). In various embodiments, P2PE manager 166 may determine that a payload from POI device 104 has been tampered with by receiving a payload from POI device 104 after merchant 132 has recorded that POI device 104's state is "In Repair," "Damaged," "Retired," "Destroyed," or "Stolen" (e.g., P2PE manager should not be receiving a payload from POI device 104 and thus will not decrypt the payload). In many cases, if P2PE manager 166 determines that POI device 104 has been tampered with, then it will transmit a notification to merchant 132 and/or any other appropriate party, change the state of POI device 104 in the POI database 168 to "Tampered" and will no longer decrypt payloads from POI device 104.

System Architecture

FIGS. 2A, 2B, and 2C are block diagrams depicting exemplary system architectures of the exemplary P2PE system of FIG. 1. These architectural components are organized into overarching processes for secure handling of devices and payloads (e.g., for decryption): secure device handling process 300, merchant data process 400, and P2PE Management System 500. These major components are intended to be exemplary only and are used to assist in explaining the systems and methods herein. As will be understood, the following architectural components may be operatively connected in any suitable way and may include suitable processors, databases, firewalls, and the like. Further, the various components discussed herein may be distributed and operatively connected in any suitable way. For example, in various embodiments, the architectural components discussed below may be physically connected and located in the same room and/or may be connected via the Internet or private network and may be located remotely.

Secure POI Handling System

Secure POI handling system 300 is more fully described in this document in connection with FIG. 3. Secure POI handling system 300, according to particular embodiments, includes a point of interaction manufacturer 302 (e.g., manufacturer 102 in FIG. 1) that produces and ships a POI device 350 via secure handling procedures to a key injection facility (KIF) 502. KIF 502 injects the POI device 350 with an encryption key and securely ships POI device 350 to a merchant. POI device 350 is included in merchant data process 400 as further described herein.

POI manufacturer 302 manufactures devices that may be used with the systems and methods discussed herein. POI manufacturer 302 may manufacture any suitable device, including any POI device approved by the PCI Security Standards Council ("PCI SSC") or other suitable device for receiving information to be encrypted. Examples of PCI SSC-approved devices can currently be found on PCI SSC's website at https://www.pcisecuritystandards.org/approved_companies_providers/approved_pin_transaction_security.php. In one or more embodiments, POI device 350 is a stand-alone swipe terminal, such as ID TECH's SecuRED™ SRED device. In some embodiments, POI device 350 is an all in one type mobile business solution, such as 4P Mobile Data Processing's FDA600-POS device. In at least one embodiment, the POI device 350 is a countertop terminal, such as Atos Worldline's Yomani device.

As will be understood from discussions herein, POI manufacturer 302 is merely an exemplary manufacturer. In various embodiments, the system may be configured to decrypt any type of encrypted information (e.g., in a "decryption as a service" environment) from any suitable device. In these embodiments (and others), the manufacturer may produce any suitable encryption device for encrypting social security numbers, driver license numbers, personal data, patient information, etc., and thus, may not necessarily produce POI devices. However, for the purposes of clarity of and brevity, a POI manufacturer and POI devices are shown in the figures.

It will be understood by one of ordinary skill in the art that merchants and key injection personnel do not typically program POI devices (other than encryption key injection at a key injection facility). Thus, in many of the embodiments discussed herein, POI manufacturer 302 loads and/or programs POI device 350. In various embodiments, POI manufacturer 302 configures POI device 350 with particular firmware and/or a particular version of firmware. In further embodiments, POI manufacturer 302 configures POI device 350 with various hardware and software security features (e.g., software for encrypting swipe data substantially immediately after being read by POI device 350, hardware that destroys/erases any keys stored by POI device 350 upon tampering, etc.).

In particular embodiments, POI manufacturer 302 configures POI device 350 to transmit a payload of information, where the payload includes a specific set of information. In these (and other) embodiments, the payload may include any suitable information such as device serial number and/or any other unique device identifier, unique identifier and version number of the firmware installed on the device, date of device manufacture, device brand identifier, device model identifier, etc. In further related embodiments, the POI manufacturer 302 configures POI device 350 to transmit the payload in a particular format (e.g., portions of data in a particular order, numbers in a particular format such as hexadecimal, character, etc.). These configurations may be used by P2PE Management System 500 (or 166) to identify particular POI devices (e.g., POI device 350 and/or POI device 104 (FIG. 1) and to verify the authenticity of the received data via a fingerprint, as will be further discusses in relation to FIGS. 5A and 5B.

Although not shown in FIGS. 2A, 2B, and 2C, POI manufacturer 302 may include computing devices operatively connected to P2PE Management System 500 via any suitable connection.

KIF 502 includes any suitable computers, machines, etc. to receive encryption keys 562, send and receive data 512, securely inject POI device 350 with an encryption key, bag POI device 350 with a serialized tamper-resistant bag, and ship POI device 350 to a merchant. As discussed herein, in various embodiments, upon receipt of POI device 350, a user enters (e.g., keys, scans, etc.) information associated with POI device 350 into P2PE manager 166 (serial number, firmware version number, etc.). In these embodiments, the user may enter the information associated with POI device 350 via a bar code scanner operatively connected to a computing device, via a keyboard operatively connected to a computing device, via a touchscreen interface operatively connected to a computing device, etc.

Computing devices located at the KIF may be any suitable computing devices, including desktop computers, laptop computers, servers, tablets, other mobile devices, etc. In various embodiments, at least some of the computing devices located at the KIF are configured to connect to the P2PE Management System 500 via a suitable user interface. In some embodiments, information is exchanged between computing devices located at the KIF and the P2PE Management System 500 via email, http, or other suitable protocol.

According to particular embodiments, KIF 502 includes a tamper resistant security module ("TRSM") for assembling key parts (as discussed above, in various embodiments, the base derivation key is sent to the KIF in two parts and is reassembled). The TRSM may be any suitable TRSM incorporating physical protections, including, for example, tamper-evident seals, hardened casings, and hardware and software to erase the contents of the TRSM upon detection of tampering. In various embodiments, upon combining and validation of key parts, the TRSM produces a cryptogram representing the base derivation key. In some embodiments, the cryptogram is transferred to a smart card.

The smartcard may be any suitable smartcard. In various embodiments, the smartcard is a smartcard with a chip including one or more processors for key generation, signature, and/or encryption. In particular embodiments, the smartcard is equipped with software for creating suitable algorithms, such as hashing algorithms. In at least one embodiment, the smartcard is operative for communicating with the TRSM and suitable key injection devices (e.g., Key Loading Devices, (KLDs)). The smartcard may include other features, such as tamper-resistant measures, tamper notification measures, anti-tearing measures, etc.

According to particular embodiments, the smart card is not used. In these embodiments (and others), the base derivation key is sent to the KIF in two parts and is reassembled as a KLD, without the use of the smartcard.

In various embodiments, the KIF 502 includes one or more KLDs for injecting POI devices with encryption keys. KLDs may be any suitable key loading/key fill devices and, in various embodiments, are secure cryptographic devices (SCDs).

According to various embodiments, once injected with an encryption key, POI device 350 is packaged in a tamper evident bag and shipped to the merchant for deployment.

Merchant Data System

As shown in the embodiments depicted in FIG. 2A, merchant data system 400 includes POI device 350 deployed to receive payment transactions and POI device 350 operatively connected to a payment transaction processor 416. In FIG. 2A, third party transaction processor 416 as excluded from P2PE Management System 500 (e.g., third party transaction processor 416 is provided by a party other than the payment system, such as by the merchant or by a suitable partner). An exemplary merchant data process and an exemplary merchant P2PE report process are more fully described in this document in connection with FIGS. 4A and 4B, respectively. The merchant may include any suitable computing devices, point of sale devices, servers, databases, processors, etc.

As will be understood by one of ordinary skill in the art, POI device 350 may be operatively connected to any suitable merchant point of sale system. In various embodiments, POI device 350 is operatively connected to a cash register, which may be digital, analog, touchscreen, etc. According to particular embodiments, POI device 350 is operatively connected to a mobile device, such as a mobile phone, tablet, etc. running software to accept payment information. In further embodiments, POI device 350 is operatively connected to a desktop computing device for completing sales.

In the embodiments shown in FIG. 2A, POI device 350 is operatively connected to payment transaction processor 416. It will be understood by one of ordinary skill in the art that POI device 350 may be directly connected to payment transaction processor 416 or may be indirectly connected to payment transaction processor 416 (e.g., POI device 350's payloads are transmitted through other components of a point of sale system to payment transaction processor 416). In various embodiments, third party transaction processor 416 may represent any suitable number of servers, processors, etc. and may be located in any suitable location, including at the merchant or at a location remote from the merchant.

As shown in FIG. 2A, third party transaction processor 416 is operatively connected (via Internet 209 or a private network (PN)) to one or more card networks 202, P2PE Management System 500, and issuer 214. In this embodiment (and others), POI device 350 payloads are transmitted to third party transaction processor 416, then, via Internet 209, to the P2PE management system processes 500 for decryption and re-encryption, then the re-encrypted payment data is transmitted by Internet 209 and/or by PN to card networks 202.

The merchant system may include any number of suitable computing devices (not shown in FIG. 2A). These merchant computing devices may be any suitable computing devices, such as desktop computers, laptop, computers, tablets, etc. and may be operatively connected to the P2PE Management System 500. The merchant computing devices, in various embodiments, enable users at the merchant to input information regarding POI device 350 to be transmitted to P2PE Management System 500 (e.g., state change information, tracking information, etc.). In one or more embodiments, the merchant computing devices may also be configured to produce various auditing reports regarding P2PE compliance.

P2PE Management System

In the embodiment shown in FIGS. 2A, 2B, and 2C, P2PE Management System 500 may include any suitable software and/or hardware components, including servers, mobile computing devices, desktop computers, one or more databases, and any number of suitable processors. According to particular embodiments, P2PE Management System 500 is configured to manage states of various POI devices (e.g., POI device 350). In these embodiments (and others), P2PE Management System 500 may utilize any number of suitable tables and databases to store tables of information regarding the various states of POI devices. In particular embodiments, P2PE Management System 500 includes one or more processors for receiving state changes from computing devices, receiving information regarding state changes of various POI devices, determining whether the state of a particular POI device should be changed based on received information, etc.

According to various embodiments, P2PE Management System 500 includes one or more databases and one or more processors for receiving identification data associated with various POI devices (e.g., POI device 350), such as a device serial number, a device (encryption) key serial number, key sequence number, a device version number, a device firmware number/indicator, etc. In one or more embodiments, P2PE Management System 500 is configured to store the received identification information and, in at least one embodiment, indexing the identification and other information associated with a particular POI device by the device serial number. For example, in a particular embodiment, P2PE Management System 500 receives a payload of information from a third-party payment processor (e.g., the payment payload is sent from a merchant POI device to the third-party payment processor then to the P2PE management system) including a particular device serial number. Continuing with this example, P2PE Management System 500 is configured for parsing the payload to extract the particular device serial number and for searching and locating additional device information based on the particular device serial number.

As a second particular example, P2PE Management System 500 receives a payload of information from a third-party payment processor; however, in this second particular example, the third-party payment processor sends a portion of the payload, which has already been parsed. Continuing with the second particular example, the P2PE management system 510 receives a third-party payment processor identifier, a key sequence number, and any encrypted payment information to be decrypted.

In various embodiments, P2PE Management System 500 includes at least one database and at least one processor for creating and storing identifiers associated with POI devices (and/or any suitable encryption device or system). In some embodiments, P2PE Management System 500 is configured to create a device identifier or "fingerprint" based on the format of one or more payloads received from a particular POI device (e.g., POI device 350). In these embodiments (and others), P2PE Management System 500 is configured to compare the format of future payloads received from the particular POI device to the fingerprint to verify the authenticity of the payload (e.g., that the payload has not been tampered with and/or compromised in some way).

According to one or more embodiments, P2PE Management System 500 includes various processors and databases for creating audit reports for merchants. In these embodiments (and other embodiments), P2PE Management System 500 is configured to receive a request for an audit report from a computing device associated with a merchant and access one or more tables configured to store information associated with various POI devices associated with the merchant. P2PE Management System 500, in these embodiments, is further configured to aggregate, summarize, and facilitate the display (e.g., display on a screen of a computing device at the merchant, send to a printer of a computing device at the merchant, etc.) of the information associated with the various POI devices associated with the merchant.

As will be understood by one of ordinary skill in the art, any of the above mentioned processors may perform more than one function described and any of the above mentioned databases may store more than one type of information. Thus, the discussion above should not necessarily limit the various processors disclosed herein as having only the functionality discussed above.

Now referring to FIG. 2B, an exemplary architecture of the P2PE Management System 500 according to one embodiment of the present system is shown. In various embodiments, the P2PE Management System 500 may authenticate and decrypt payloads received from one or more third party partners. Each of the payloads received from the one or more third party partners may have originated at a device, such as a POI device, or another suitable system that transmits a payload for authentication and decryption (e.g., a healthcare system, a governmental body, etc.).

According to particular embodiments, the one or more third party partners may receive several thousand payloads per second from a large network of devices, such as, for example, in embodiments where the one or more third party partners are one or more payment processors that may service large retailers or many retailers. These payloads may require decryption so that the one or more third party partners can process the information contained within the payloads in real-time (e.g., real-time payment processing). In various embodiments, P2PE Management System 500 may be configured to authenticate and decrypt thousands of transactions per second. In a particular embodiment, as will be further discussed here, the P2PE Management System 500 may be configured to decrypt up to 1600 payloads per second. In further embodiments, the P2PE Management System 500 may be scalable and configured to process many thousands of payloads per second.

The P2PE Management System 500 includes, in the embodiment shown in FIG. 2B, a P2PE manager (e.g., P2PE manager 166) and a Decryption Web Server 234. In various embodiments, the P2PE manager has the functionality described in FIG. 1 and comprises an Authentication Web Server 224, a Read-Only Database 228, a Master Read-Only Database 230, and a Read/Write Database 232. The P2PE Management System 500, in the embodiment shown in FIG. 2B, may be located behind a firewall 220 and operatively connected to a load-balancer 222. In various embodiments, the load-balancer 222 comprises a combination of hardware, software, virtual machine, or other similar device that distributes workloads between several computing devices. The load-balancer 222, in one embodiment, may distribute and route payloads from the third party partners to the Authentication Web Server 224, from the Authentication Web Server 224 to the Decryption Web Server 234, and from the Decryption Web Server 234 to the third party partners (as processed, unencrypted payloads). As will be understood by one of ordinary skill in the art, the P2PE Management System 500 is an exemplary embodiment only and various other components may be added, removed, or rearranged to provide functionality as described herein.

The Authentication Web Server 224 (may also be referred to herein as a "frontend web server") is a web server, which is, in various embodiments, a combination of hardware, software, virtual machine, or other similar device that stores, processes, and delivers content to computing devices. In one embodiment, the Authentication Web Server 224 may be hosted on a virtual machine and may authenticate the third party partners that transmit payloads for decryption and the devices that generated the payload. In one embodiment, the Authentication Web Server 224 may be operatively connected to a Read-Only Database 228 and a load-balancer 222.

In various embodiments, the Authentication Web Server 224 may authenticate each payload received by the P2PE Management System 500 for decryption. The Authentication Web Server 224 may confirm, in one embodiment, that the partner requesting decryption is making a valid request and that the format of the payload from a specific device conforms to the expected format of payloads received from the device. In one embodiment, the Authentication Web Server 224 may determine that the request for decryption was transmitted from an approved IP address, or that the third party partner transmitted the appropriate identification credentials, or any other suitable method of identity authentication. As will be explained in further detail in conjunction with the description of FIG. 5B, the Authentication Web Server 224 may compare the fingerprint (e.g., format, order, and number of data items included in the payload) of the device that generated a particular payload to a previously-stored device fingerprint for the specific device stored in the Read-Only Database. If the fingerprints do not match, then, in particular embodiments, the Authentication Web Server 224 denies the decryption request and generates and sends an error log to a read/write database.

Generally, when the P2PE Management System 500 receives a request for decryption, the load-balancer 222 transmits the request and corresponding payload to the Authentication Web Server 224. The Authentication Web Server 224, in one embodiment, may first validate the partner that transmitted the request for decryption. In various embodiments, this validation occurs, for example, by checking that the request for decryption was generated from a known IP address that is associated with the partner or that the partner transmitted the correct identification number with the request or other similar and secure method of authentication. The Authentication Web Server, in one embodiment, after validating the partner, may validate the specific device that generated the payload. As will be explained in further detail in conjunction with the description of FIG. 5B, the Authentication Web Server 224, in various embodiments, may compare the fingerprint of the payload to the known device fingerprint of the specific device. In one embodiment, if the fingerprints do not match, then the Authentication Web Server 224 may reject the decryption request and transmit a decryption exception log to the Read/Write Database 232. According to one embodiment, if the fingerprints match, then the Authentication Web Server 224 may transmit the payload to the load balancer 222 (which may transmit it to the Decryption Web Server 234) and may transmit a decryption log to the Read/Write Database 232.

In various embodiments, the Authentication Web Server 224 comprises a plurality of Authentication Nodes 226. Authentication Nodes 226 may be, in one embodiment, applications designed to process the authentications of partners and device payloads by accessing the Read-Only Database 228. In one embodiment, Authentication Nodes 226 may be configured to create logs of authentications and exceptions and to transmit those logs to the Read/Write Database 232. In one embodiment, to process 1,600 payloads per second, the Authentication Web Server 224 comprises three Authentication Nodes 226.

The Read-Only Database 228 comprises a database, which is, in various embodiments, a combination of hardware, software, virtual machine, or other similar device that is an organized collection of data (e.g., containing data tables, etc.). In one embodiment, the Read-Only Database 228 may contain data necessary for authenticating the payloads and requests for decryption and may be hosted as a virtual machine on the Authentication Web Server 224.

In one embodiment, the Read-Only Database 228 may be operatively connected to the Authentication Web Server 224 and the Master Read-Only Database 230. The Read-Only Database 228 may be configured, in one embodiment, for storing read-only authentication data for use in determining whether payloads have been compromised and authenticating third party partners. In one embodiment, the Read-Only Database 228 may be configured for storing read-only authentication data for use in determining whether a third party partner is the appropriate entity to be making the decryption request. As will be appreciated by one having ordinary skill in the art, as the Read-Only Database 228 may be read-only from the perspective of the Authentication Web Server 224, the Read-Only Database 228 may not be configured to write write-requests from the Authentication Web Server 224 and instead may transmit them to the Master Read-Only Database 230.

After receiving a payload and request for decryption, in one embodiment, the Authentication Web Server 224 may query the Read-Only Database 228 to determine whether the payload is valid or has been compromised (e.g., by authentication and validation). In one embodiment, the Authentication Web Server 224 may query the Read-Only Database 228 to determine the validity of the third party partner that transmitted the payload (e.g., by transmitting the firmware number or serial number of the device as further discussed herein). The Read-Only Database 228, in one embodiment, transmits a response to the query back to the Authentication Web Server 224. If the response confirms the validity of the third party partner, then the Authentication Web Server 224 may query the Read-Only Database 228 to determine the validity of the payload of the device. The Read-Only Database 228, in one embodiment, may transmit a response to the query back to the Authentication Web Server 224 that includes data necessary to validate the payload. In one embodiment, the Authentication Web Server 224 may compare the payload to the response from the Read-Only Database 228 to determine the validity of the payload. If the comparison confirms the validity of the payload of the device, then the Authentication Web Server 224 may transmit a log of the decryption request to the Read-Only Database 228. If either the third party partner or payload is invalid, then the Authentication Web Server 224 may transmit an exception log to the Read-Only Database 228. In embodiments where the Read-Only Database 228 is read-only from the perspective of the Authentication Web Server 224, the Read-Only Database 228 may transmit exception logs and logs of decryption requests to the Master Read-Only Database 230.

As will be appreciated by one having ordinary skill in the art, the read-only perspective of the Read-Only Database 228 may permit the Authentication Web Server 224 to query the Read-Only Database 228 and the Read-Only Database 228 to respond to those queries faster than if the Read-Only Database 228 were configured with read/write functionality. In one embodiment, the Read-Only Database 228 includes a MONGO-formatted database or any other NoSQL format that enables the database to handle the necessary requests per second (e.g., up to about 1600 per second). As will be appreciated by one having ordinary skill in the art, this type of database is easily refreshable and can be configured to operate quickly as it is not as robust a data structure as a relational database. In one embodiment, the data stored in the database need not be associated with other data (e.g., the data is stored in collections of individual data objects). Further, in various embodiments, the Read-Only Database 230 may be configured to not confirm write-requests so that the database can perform more write-requests per second. In various embodiments, to avoid the potential data losses that accompany this functionality, the Read-Only Database 228 may be operatively connected to a Master Read-Only Database 230.

The Master Read-Only Database 230 includes a database, which is, in various embodiments, a combination of hardware, software, virtual machine, or other similar device that is an organized collection of data (e.g., containing data tables, etc.). In one embodiment, the Master Read-Only Database 230 may contain data necessary for refreshing the Read-Only Database 228 and may be hosted as a virtual machine on the Authentication Web Server 224.

In one embodiment, the Master Read-Only Database 230 may be operatively connected to the Read-Only Database 228, the MQTT Queues 231, and the Read/Write Database 232. The Master Read-Only Database 230 may be configured, in one embodiment, for receiving and storing authentication data received from the Read/Write Database 232 for refreshing the Read-Only Database 228. In various embodiments, the Master Read-Only Database 230 may be read-only from the perspective of the Read-Only Database 228 and read/write from the perspective of the Read/Write Database 232. As will be appreciated by one having ordinary skill in the art, as the Master Read-Only Database 230 may be read-only from the perspective of the Read-Only Database 228, the Master Read-Only Database 230 may not be configured to write write-requests from the Read-Only Database 228 and instead may transmit them to the MQTT Queues 231 and the Read/Write Database 232.

In one embodiment, the Master Read-Only Database 230 may receive logs from the Read-Only Database 228 and may transmit those logs to the MQTT Queues 231 and the Read/Write Database 232. The Master Read-Only Database 230, in one embodiment, may receive updates from the Read/Write Database 232, refresh its data tables based on the updates, and transmit the updates to the Read-Only Database 228. As will be appreciated by one having ordinary skill in the art, the Master Read-Only Database 230 may prevent data loss between the Read-Only Database 228 and the Read/Write Database 232.

In one embodiment, the Master Read-Only Database 230 includes a MONGO-formatted database or any other NoSQL format that enables the database to handle the necessary requests per second. As will be appreciated by one having ordinary skill in the art, this type of database may be easily refreshable and can be configured to operate quickly as it is not as robust a data structure as a relational database. In one embodiment, the data stored in the database need not be associated with other data (e.g., the data is stored in collections of individual data objects). Further, the Master Read-Only Database 230, in various embodiments, may be configured to perform write-requests without confirming them so that the database can perform more write-requests per second. To avoid the potential data losses that accompany this functionality, the Master Read-Only Database 230 may be operatively connected to the Read/Write Database 232 and the MQTT Queues 231.

The MQTT Queues 231 includes a message queuing protocol for storing messages (e.g., log write-requests). In one embodiment, the MQTT Queues 231 may be operatively connected to the Master Read-Only Database 230 and the Read/Write Database 232. In one embodiment, the MQTT Queues 231 may be within a separate partition within the same hardware, software, virtual machine, or other similar device that hosts the Master Read-Only Database 230. The MQTT Queues 231 may be configured, in one embodiment, with a queuing protocol for receiving, queuing, and transmitting the messages (e.g., logs, events exceptions, etc.) transmitted from the Master Read-Only Database 230 via the message queuing protocol to the Read/Write Database 232. In various embodiments, the MQTT Queues 231 may process the messages to the Read/Write Database 232 via message queue telemetry transport messaging protocol (e.g., MQTT).

In one embodiment, the MQTT Queues 231 may receive messages from the Master Read-Only Database 230 and store those messages within its queue using a message queuing protocol until a particular event or set of circumstances occurs. In one embodiment, this functionality enables the MQTT Queues 231 to function as a back-up for messages transmitted by the Authentication Web Server 224 to be received by the Read/Write Database 232. As will be appreciated by one having ordinary skill in the art, the MQTT Queues 231 may prevent data loss between the Master Read-Only Database 230 and the Read/Write Database 232. Further, the MQTT Queues 231 may permit the P2PE Management System 500 to operate normally even if the Read/Write Database 232 is offline. Generally, the MQTT Queues 231 may store log write-requests received from the Read-Only Database 230 and the Read-Only Database 228; thus, in one embodiment, the log write-requests may be queued until the Read/Write Database 232 can write the log write-requests, which may prevent the loss of any log write-requests generated when the Read/Write Database 232 is not operating.

In one embodiment, upon determining that less than a particular number of payloads are being processed per second by the P2PE Management System 500, the MQTT Queues 231 may transmit messages from its queue to the Read/Write Database 232. For example, if the P2PE Management System 500 is processing less than 250 (or, e.g., 500, 750, 1,000, etc.) payloads per second, then the MQTT Queues 231 may be configured to transmit the messages in its queue. In a particular embodiment, if the P2PE Management System 500 is processing less than 500 payloads per second, then the MQTT Queues 231 may begin transmitting messages to the Read/Write Database 232 until either all of the messages have been transmitted or the system begins processing more than 500 payloads per second. If all of the messages have been transmitted, then the MQTT Queues may stop transmitting messages and may wait to receive more messages from the Master Read-Only Database 230. If the P2PE Management System 500 begins processing more than 500 payloads per second, then the MQTT Queues 231 may stop transmitting messages and may wait to begin transmitting messages again until the P2PE Management System 500 is processing less than 500 payloads per second. As will be appreciated by one having ordinary skill in the art, the MQTT Queues 231 may receive messages from the Master Read-Only Database 230 regardless of whether it is transmitting messages to the Read/Write Database 232.

The Read/Write Database 232 (may also be referred to herein as a "backend read/write database") is a database, which includes, in various embodiments, a combination of hardware, software, virtual machine, or other similar device and is an organized collection of data (e.g., containing data tables, etc.). In one embodiment, the Read/Write Database 232 may contain data necessary for authenticating and decrypting payloads from third party partners, and substantially all of the messages generated by the Authentication Web Server 224 and Decryption Web Server 234 and may be hosted as a virtual machine. According to various embodiments, the Read/Write Database 232 may perform the major functions of the P2PE manager 166, as describe in relation to FIG. 1, other than the functionality of the Authentication Web Server 224 and databases as previously described. In various embodiments, the Read/Write Database 232 may receive state changes for devices, such as via transmission 122, 124, and 126, and may receive serial numbers for devices. In one embodiment, the Read/Write Database 232 may update its data tables based on the received state changes and serial numbers.

In one embodiment, the Read/Write Database 232 may be operatively connected to the Master Read-Only Database 230, the MQTT Queues 231, and the Decryption Web Server 234. The Read/Write Database 232 may be configured, in one embodiment, for storing and transmitting authentication data to the Master Read-Only Database 230, receiving and storing messages from the MQTT Queues 231, updating the authentication data based on the exception messages, and transmitting updates for the Read-Only Database 228 to the Master Read-Only Database 230. In one embodiment, the Read/Write Database 232 includes a MYSQL-formatted database. As will be appreciated by one having ordinary skill in the art, a MYSQL database includes a relational database management system, which may allow the Read/Write Database 232 to store logs in association with the third party partners and POI that generated those logs, and may be easily compatible with multiple systems, which may allow the P2PE Management System 500 to interface with multiple outside systems for functions including, but not limited to, auditing, billing, etc.

In one embodiment, the Read/Write Database 232 may receive messages from the MQTT Queues 231. If those messages are authentication logs, then the Read/Write Database 232 may store and associate the logs with the third party partner and device that generated the payload that was authenticated. If those messages are exception logs, then the Read/Write Database may stores those logs and may update the records of the third party partner and device that generated the payload to reflect the exception. In one embodiment, the Read/Write Database 232 may transmit updates to the Master Read-Only Database 230 to refresh both the Master Read-Only Database 230 and the Read-Only Database 228.

According to various embodiments, the ReadWrite Database 232 may receive decryption logs and decryption exception logs from the Decryption Web Server 234. The decryption logs may indicate a successful decryption of a payload and may be stored in relation to the associated partner, device, and payload for the decryption within the Read/Write Database 232. The decryption exception logs may indicate an unsuccessful decryption of a payload and may be stored in relation to the associated partner, device, and/or payload for the decryption within the Read/Write Database 232. One skilled in the art will appreciate that these logs permit the P2PE Management System 500 to produce reports regarding the number of payloads decrypted, unsuccessful payload decryptions, etc. In various embodiments, the decryption logs and decryption exception logs from the Decryption Web Server 234 may be queued before being transmitted to the Read/Write Database 232 in a process similar to that for authentication logs and exceptions logs on the MQTT Queues 231 as discussed previously herein.

The Decryption Web Server 234 includes a web server, which is, in various embodiments, a combination of hardware, software, virtual machine, or other similar device that stores, processes, and delivers content to computing devices. In one embodiment, the Decryption Web Server 234 may be hosted on a virtual machine and may decrypt payloads received from third party partners. In one embodiment, the Decryption Web Server 234 may be operatively connected to the Read/Write Database 232 and the load-balancer 222.

In various embodiments, the Decryption Web Server 224 may decrypt each payload received by the P2PE Management System 500 for decryption. According to various embodiments, the Decryption Web Server 224 may be responsible for determining the appropriate decryption algorithm to decrypt the payload, decrypting the payload, confirming decryption, transmitting the decrypted payload back to the load-balancer 22, and generating a log of the decryption.

Generally, when the P2PE Management System 500 receives a request for decryption, the load-balancer 222 transmits the request and corresponding payload to the Authentication Web Server 224. In one embodiment, the Authentication Web Server 224 may parse the payload, prior to transmitting the request back to the load-balancer 222, to determine the key index for that particular payload. Generally, a key index indicates a base key (e.g., algorithm) used as the basis for encrypting a payload of the particular device and will be better understood in connection with the description of FIGS. 6, 11, 12, etc. After the Authentication Web Server 224 authenticates the third party partner and payload, in one embodiment, the Authentication Web Server 224 may transmit the request, key index, and corresponding payload back to the load-balancer 222, which may transmit the request, key index, and corresponding payload to the Decryption Web Server 234. According to a different embodiment, the Decryption Web Server 234 may determine the appropriate decryption algorithm to decrypt the payload, decrypt the payload, and confirm that the decryption was successful (e.g., confirms that the decrypted payload contains credit card information as expected and not random data). In various embodiments, the Decryption Web Server 234 may transmit the decrypted payload back to the load-balancer 222, which may transmit the decrypted payload to the third party partner, and generate a log of the decryption. In one embodiment, the Decryption Web Server 234 may transmit that log of the decryption to the Read/Write Database 232.

In various embodiments, the Decryption Web Server 234 includes a Hardware Security Module 238 (e.g., HSM). In various embodiments, the HSM 238 may receive the request, key index, and corresponding payload from the Decryption Web Server 234. Generally, in various embodiments, the HSM 238 may process the key index to determine the appropriate method to use to decrypt the payload, decrypt the payload, confirm decryption, transmit the decrypted payload back to the load-balancer 22, and generate a log of decryption. In one embodiment, the HSM 238 may determine the appropriate decryption algorithm to decrypt the payload, decrypt the payload, confirm decryption, transmit the decrypted payload back to the load-balancer 22, and generate a log of the decryption. In various embodiments, HSM 238 includes suitable one or more processors and one or more databases for creating and storing encryption keys. In particular embodiments, HSM 238 includes at least one processor and at least one database for receiving payloads, for deriving encryption keys from payload information, for decrypting payment data included in such payloads, re-encrypting at least a portion of a payload, including the payment information, and transmitting the re-encrypted portion of the payload to a card network (e.g., card network 202) via the Internet 209 and/or a private network (PN). Generally, HSM 238 can decrypt payloads in any format (e.g., TDES/3DES, DUKPT, format-preserving encryption (e.g., BPS), base64 encoded, hexadecimal encoded, encrypted value name, etc.) HSMs will be further understood in relation to the description of FIGS. 1, 4, 5, 6, etc.

According to particular embodiments HSM 238 includes a device that provides FIPS 104-2 Level 3 certified physical and logical protection to cryptographic keys or other suitable PCI-compliant HSM. An example of such an HSM is the SafeNet Luna EFT HSM. Other examples of PCI approved HSMs can be found at https://www.pcisecuritystandards.org/approved_companies_providers/approved_pin_transaction_security.php.

Generally, a HSM may process up to 1,600 payloads per second. To understand how the P2PE Management System 500 handles more than 1,600 payloads per second, a discussion of the scalability of the P2PE Management System 500 may be useful.

Now referring to FIG. 2C, an exemplary architecture of the P2PE Management System 500 according to one embodiment of the present system is shown. In various embodiments, the P2PE Management System 500 may be scalable to enable the P2PE Management System 500 to decrypt more payloads per second.

The scalability of P2PE Management System 500, in one embodiment, may not be dependent on any one component of the system but may instead be based on the desired number of decryptions per second. Accordingly, in one embodiment, the P2PE Management System 500 may be expanded based on one rate-limiting component, and all other components may be scaled based on that rate-limiting component. According to various embodiments, the scalability of the P2PE Management System 500 may be based on the number of HSMs 238 in the P2PE Management System 500 (e.g., the rate-limiting component). For example, the HSM 238 generally may process up to about 1,600 decryptions (e.g., payloads) per second. If 3,200 decryptions per second are desired, then the P2PE Management System 500, in one embodiment, should include two Decryption Web Servers 234, each including one HSM 238, (or, alternatively, one Decryption Web Server 234 including two HSMs 238) operatively connected to a load-balancer 222 and a Read/Write Database 232. To support two HSMs 238 processing up to about 3,200 decryptions per second, then the P2PE Management System 500, in one embodiment, includes three Authentication Web Servers 224. In this embodiment, each of the three Authentication Web Servers 224 may be operatively connected to the load-balancer 222 and a Read-Only Database 228. Continuing with this embodiment, the system includes three Read-Only Databases 228 operatively connected to the Master Read-Only Database 230, which may be operatively connected to the MQTT Queues 231 and Read/Write Database 232. With this configuration, in one embodiment, the P2PE Management System 500 may authenticate and validate up to about 3,200 payloads per second and the HSMs 238 become the rate-limiting component of the P2PE Management System 500.

In one embodiment, when the P2PE Management System 500 includes multiple Read-Only Databases 228, the Master Read-Only Database 230 may refresh the Read-Only Databases 228 at substantially the same time by transmitting the same update to each Read-Only Database 228. Similarly, in one embodiment, when the P2PE Management System 500 includes multiple Read-Only Databases 228, the Master Read-Only Database 230 may receive authentication logs and exception logs from each of the Read-Only Databases 228 at substantially the same time and pass those messages into the same MQTT Queues 231 for transmission to the Read/Write Database 232.

According to various embodiments, the P2PE Management System 500 includes only one Master Read-Only Database 230, MQTT Queues 231, and ReadWrite Database 232, regardless of the number of Authentication Web Servers 224, Read-Only Databases 228, Decryption Web Servers 234, and HSMs 238. According to various embodiments, to process up to about 6,400 payloads per second, the P2PE Management System 500 includes four Decryption Web Servers 234, four HSMs 238, six Authentication Web Servers 224, six Read-Only Databases 228, one Master Read-Only Database 230, one MQTT Queues 231, and one Read/Write Database 232. According to various embodiments, to process up to about 12,800 payloads per second, the P2PE Management System 500 includes eight Decryption Web Servers 234, eight HSMs 238, twelve Authentication Web Servers 224, twelve Read-Only Databases 228, one Master Read-Only Database 230, one MQTT Queues 231, and one Read/Write Database 232.

Exemplary System Processes

Exemplary POI Handling Process (FIG. 3)

FIG. 3 depicts a high-level flow chart of an exemplary secure device handling process 300 as shown in FIG. 2A. In various embodiments, this POI handling process may help verify a secure chain of custody for a POI device. To briefly summarize, in a particular embodiment, as a POI device is transported from and handled by different entities, the POI Manager assign various states to the POI device. In these particular embodiments (and others), the POI Manager verifies that the POI device has been assigned the correct sequence of states before facilitating the decryption of a payload of the POI device. This secure POI handling process, in particular embodiments, helps identify whether POI devices have been tampered with and/or switched (e.g., with a nefarious POI device) during the transport of a POI device between the time of manufacture to the time of deployment at a merchant. POI handling process 300, as shown in FIG. 3 and described immediately below may help illustrate at least one embodiment of this POI handling process.

Beginning at step 330, the system is configured to receive particular POI device identification information at the P2PE Management System 500. In various embodiments, the particular POI device identification information includes a serial number associated with the particular POI device (e.g., POI device 350 in FIG. 2A). In particular embodiments, the particular POI device identification information includes version of the firmware installed on the particular POI device. In further embodiments, the particular POI device identification information includes any other suitable information, such as model, device type, device manufacture date, etc.

The system may be configured to receive the particular POI device identification information from any suitable entity in any suitable way. In particular embodiments, the particular POI device identification information is transmitted (e.g., via encrypted electronic packets) from a computing device at a key injection facility (KIF). In some embodiments, the particular POI device identification information is received from a computing device associated with the manufacturer. In further embodiments, the particular POI device identification information is input by a person into a computing device operatively connected to the POI Manager.

At step 332, the system is configured to, in response to receiving the particular information associated with POI device 350, set the state of POI device 350 to indicate that the POI device is new/ready for programming. (e.g., the system is configured to set the state of the particular POI device to "New"). In various embodiments the system is configured to change the state of the POI device to New by adding the POI device (or associated identifier) to a table or list of POI devices with a New status. In further embodiments, the system is configured to change the state of the POI device by including the state of the POI device in a table with a POI device identifier (e.g., the POI device is listed by identifier on a table and the state associated with the POI device changes). In still further embodiments, the information associated with the POI device in the system may include various bits that indicate a state (e.g., information about POI devices include bits indicating each state and can be set to on or off to indicate the state of the device). In this embodiments (and others), the system may be configured to change the bit associated with the New state to on or to "1".

At step 334, the system is configured to receive an indication that the particular POI device is injected with an encryption key. As discussed herein, in various embodiments, POI devices are stored at a KIF until they are injected. In some embodiments, once the particular POI device is ordered from a merchant (or at any other suitable time), the particular POI device is injected with an encryption key under special security protocol (as discussed elsewhere herein).

The system may be configured to receive the indication that the particular POI device is injected with the encryption key in any suitable way. According to particular embodiments, once injected, a user at the KIF logs into the P2PE Manager (via a suitable computing device) and indicates that the particular POI device has been injected. In some embodiments, the system may be configured to receive the indication that the particular POI device is injected automatically from a computing device linked to the key injection equipment and/or certain protocol devices associated with injecting the particular POI device.

At step 336, based at least in part on receiving the indication that the particular POI device is injected with the encryption key, the system is configured to change the state of the particular POI device to indicate that the POI device has been injected (e.g., assign an "Injected" state). In particular embodiments, the system is configured to receive the indication that the particular POI device is injected by a user manually changing the status of the particular POI device from New to "Injected." The system may be configured to change the state of the POI device in any suitable way, including (but not limited to) the ways discussed in relation to changing the particular POI device state to "New" at step 332.

At step 338, the system is configured to receive information regarding shipping the particular POI device. In various embodiments, the particular POI device is packed for shipment from the KIF to a merchant. In these embodiments (and others), the system is configured to receive various information regarding the shipping of the particular POI device such as a tamper-resistant bag number (e.g., serial number), a box number, a tracking number, merchant number, address/shipping destination, and/or any other suitable information for tracking and/or verifying the shipment of the particular POI device.

At step 340, the system is configured to receive data from a merchant indicating receipt of the particular POI device. In various embodiments, the system is configured to receive the data from the merchant indicating receipt of the particular POI device by receiving the serial number of the particular POI device. In particular embodiments, the system is configured to receive the data from the merchant indicating receipt of the particular POI device by receiving the tracking number and/or tamper resistant bag serial number associated with the POI device. In some embodiments, the system may be configured to receive the data indicating the receipt of the particular POI device in any other suitable way.

At step 342, based on receiving the data from the merchant, the system is configured to determine whether the particular POI device has been compromised during shipment. In various embodiments, the system is configured to determine whether the particular POI device has been compromised during shipment by comparing the data received from the merchant (e.g., at step 340) to the information regarding shipping the particular POI device (e.g., at step 338). According to particular embodiments, the system is configured to look up the device based on the device serial number and verify that the tracking information, tamper resistant bag serial number, etc. match. In these embodiments, the system verifies these numbers/identifiers to ensure that the particular POI device has been shipped from the KIF to the merchant without tampering or without someone swapping out the particular POI device (e.g., for a POI device that is programmed to send cardholder information to another location or any other nefarious task).

The system may be configured to compare the data received from the merchant to the information regarding shipping the particular POI device in any suitable way. In various embodiments, the system is configured to store the information regarding the shipping the particular POI device in a table associated with the particular POI device's serial number (e.g., a serial number created by the manufacturer and input to the system at the KIF). In these embodiments, upon receipt of the serial number and data from the merchant indicating receipt of the particular POI device (e.g., the information at step 340), the system is configured to look up the information regarding shipping the particular POI device by looking up the particular POI device's serial number and accessing a table with the appropriate header (e.g., "KIF shipping information" or the like) to find the information regarding shipping the particular POI device.

At step 344, the system is configured to change the state of the particular POI device to indicate that the particular POI device has been received by the merchant (but not deployed). In various embodiments, the system is configured to change the state of the POI device to "Stored" to indicate that the particular POI device is stored at the merchant.

The system may be configured to change the state of the particular POI device in any suitable way. In various embodiments, the system is configured to change the state of the particular POI device by receiving an indication to change the state of the particular POI device from a computing device associated with the merchant (e.g., a user selects or inputs a notification to change the state of the particular POI device). According to particular embodiments, the system is configured to automatically change the state of the particular POI device upon determining that the particular POI device has not been compromised during shipment (e.g., at step 342). In further embodiments, the system may be configured to At step 346, the system is configured to receive an indication that the particular POI device is deployed. In various embodiments, the system may receive an indication from a computing device (e.g., a manual indication from a user) that the particular POI device is deployed (e.g., ready to receive swipe transactions). In one or more embodiments, the system is configured to receive an indication that the particular POI device is deployed by receiving an indication at a user-interface that the particular POI device is ready for deployment, and in response, the system changes the state of the particular POI device to indicated deployment (e.g., changes the state of the POI device from "Stored" to "Deployed").

It should be understood by one of ordinary skill in the art and from the discussions herein that the state of the particular POI device may change and/or vary from the sequence discussed above. In a particular example, the merchant could receive the particular POI device and determine that it is damaged. Continuing with this particular example, the merchant could then indicate to the system that the particular POI device is damaged and the system could change the state of the particular POI device to indicate that the POI device is damaged (e.g., a "Damaged" state). As discussed below, once in the Deployed state, the particular POI device (e.g., POI device 350) is ready to receive swipe data, as described below in reference to FIG. 4A.

Exemplary Merchant Data Process (FIG. 4A)

Referring to FIG. 3, above, once a particular POI device (e.g., POI device 350), is received by a merchant and deployed, the particular POI device is, in various embodiments, ready to receive customer transactions. As will be understood by one of ordinary skill in the art, the particular POI device may require additional set-up by the merchant, such as, for example, connection to a payment processing computing device, additional software set-up, etc.

Turning to FIG. 4, at step 430, the particular POI device receives customer data. As discussed herein, the particular POI device may receive payment transaction data (card swipe data, etc.) and other customer verification information, such as, for example, biometric data (finger print, retinal scan, etc.) chip and pin data, PIN data, etc.

At step 432, immediately upon receiving the customer data, the particular POI device is configured to encrypt the customer data. In various embodiments, the particular POI device may be configured to encrypt the customer data based on the encryption key(s) that have been injected. In some embodiments, the particular POI device is configured to encrypt the customer data via an internal encryption scheme. In further embodiments, the particular POI device is configured to encrypt the customer data via an encryption key that is sent to particular POI device with each transaction.

At step 434, the particular POI device is configured to compile a payload to be transmitted to a payment processor. In various embodiments, the payload includes the encrypted customer data. In one or more embodiments, the payload includes the device serial number. In at least one embodiment, the payload includes the device serial number and/or firmware number. In further embodiments, the payload includes a manufacture date of the particular POI device. In still further embodiments, the payload includes various other information such as an encrypted PIN or other verification information associated with a customer and/or other information to identify the transaction (e.g., date of transaction, merchant, cashier number, etc.).

The particular POI device may be configured to compile the payload in any suitable format, which may be used by the system to create a fingerprint for the particular POI device as discussed herein. In various embodiments, the particular POI device is configured to compile the payload in a string of data representing various data items of the payload. In these embodiments (and others), various components of the payload string may be formatted in character, XML, or hexadecimal format.

The payload may include any suitable components. In various embodiments, the payload includes an indication of the format of the components (e.g., hexadecimal, XML, etc.). In particular embodiments, the payload includes an indication of the particular encryption (cypher) algorithm, such as, for example, RAW (e.g., data is unencrypted), triple data encryption standard ("TDES" or "3DES") indicating that the DES derived unique key per transaction ("DUKPT") encryption scheme has been used to encrypt the payload data, advanced encryption standard indicating that the AES DUKPT encryption scheme has been used to encrypt the payload data.

In various embodiments, the P2PE Manager includes an indication of a particular type of encryption associated with a particular device based on the particular device's serial number. In these embodiments, and others, the system is configured to transmit an indication of the particular type of encryption to the HSM based on the particular devices serial number.

According to particular embodiments, the payload includes card swipe data. The card swipe data may include any or all of the various tracks of data encoded in a card's magnetic stripe. As will be understood by one of ordinary skill in the art, in various embodiments, a card's magnetic stripe contains three distinct tracks of encoded data, each read by a magnetic card reader. In these embodiments, the system may be configured to encrypt and compile each track of card data. In some embodiments, each track of card data may include different information. In further embodiments, each track of card data may include at least some of the same information.

The particular POI device may be configured to compile each track of card data in any suitable way. In various embodiments, the particular POI device is configured to compile each track of card swipe data as card track format with each track formatted as a clear set of data (e.g., no encryption), followed by an encrypted set of data (e.g., the card swipe data for the particular track), followed by a dummy set of encrypted data (e.g., encrypted random data that does not represent the card swipe data). In particular embodiments, each of the clear, encrypted, and dummy sets of data may be in a character or hexadecimal format.

The particular POI device may output the above described data, for example, in the following format:

FORMAT_CIPHERED_[TRACK1][_TRACK2]
[_TRACK3]

The particular POI device may be configured to include additional data in the payload. According to particular embodiments, the particular POI device is configured to include a key serial number ("KSN") and/or device serial number ("DSN") in the payload (e.g., a key serial number indicating how the HSM should decrypt the various encrypted tracks and a device serial number as discussed herein to identify the particular POI device). In these embodiments (and others) the KSN and DSN may be formatted in either character or hexadecimal format. In further embodiments, the particular POI device is configured to include a hardware version number and/or a firmware version number, each of which may be formatted in character or hexadecimal format (or may be empty). As will be understood by one of ordinary skill in the art, the above components of the payload may be formatted in any suitable format and may arranged in the payload in any suitable way. For example, the TRACK1 data above may come before or after the FORMAT and/or CIPHERED data. Likewise, the track data may be in any other order (e.g., TRACK3 data may come before TRACK1 data). Further, the KSN or DSN data may be located anywhere in the payload string.

In a particular example, the payload string may be formatted as:

FORMAT_CIPHERED_[TRACK1][_TRACK2]
[_TRACK3]L[_KSN][_DSN]L[_HWV_HARDWARE][_LFMV_FIRMWARE]

As will be further discussed below, in particular embodiments, the system uses this payload string and the format of each data component to create a unique fingerprint for each device.

At step 436, the particular POI device is configured to transmit the payload to a payment processing system. According to particular embodiments, the particular POI device is configured to transmit the payload to a third party for payment processing. In at least one embodiment, the system is configured to transmit the payload to a payment processing system associated with the P2PE Management System 510. In some embodiments, the system is configured to transmit the payload to any suitable intermediary for processing before being sent to the payment processor. For the sake of brevity, this section of this document refers to a payment processing system, which may mean any of the above.

The particular POI device may be configured to transmit the payload to the payment processing system in any suitable way. According to some embodiments, the particular POI device is configured to transmit the payload to the payment processing system via the internet. In one or more embodiments, the particular POI device is configured to transmit the payload to the payment processing system via a secure private network. In some embodiments, the particular POI device is configured to transmit the payload to the payment processing system via a LAN, WAN, Wi-Fi, hardline, or other suitable connection.

As will be understood from discussions herein, the particular POI device, in various embodiments is a "dumb" device. Thus, the particular POI device, in these embodiments (and others) is configured to receive data (whatever the data may be), encrypt the data based on the firmware installed, compile and transmit the payload without regard to where the data is headed, whether the POI device has been tamper with, whether the POI device has been stolen, etc. It should also be understood that the particular POI device may have a variety of other security measures installed, such as, for example, tamper resistant casing, a circuit designed to self-destruct upon tampering, various audio or visual alarms, etc.

Exemplary P2PE Report Process (FIG. 4B)

Referring to FIG. 4A above, once a particular POI device (e.g., POI device 350), is received by a merchant and deployed, the particular POI device is, in various embodiments, ready to receive customer transactions. In these embodiments (and others), the merchant may be required to produce one or more audit reports and attest to the state of the POI device (and any other POI devices in the merchant's possession). According to particular embodiments, the systems and methods herein are configured to gather information and product such audit reports.

Turning to FIG. 4B, the system, at step 431, is configured to receive a request for an audit report from a computing device associated with a merchant. In various embodiments, the system is configured to receive the request for the audit report from the computing device associated with the merchant by receiving log in information (e.g., which may identify the particular merchant) associated with a particular user (e.g., username, password, and/or other suitable credentials) and receiving an indication that the particular user would like an audit report. In one or more embodiments, the system is configured to receive the request from the audit report from the computing device associated with the merchant by receiving the audit request from a particular computing device that is dedicated to communicating with the system (e.g., a computing terminal that is configured to only function with the P2PE Management System).

The audit report may be any suitable audit report that includes any suitable information. In various embodiments, as discussed above, the audit report may include information associated with one or more devices associated with the merchant and/or the status of each of the one or more devices associated with the merchant. According to particular embodiments, the audit report includes an attestation of the information associated with each of the one or more devices associated with the merchant. In further embodiments, the audit report includes an attestation by the user (e.g., representing the merchant) that the user has read, and/or that the merchant is in compliance with, a compliance manual (e.g., a P2PE Instruction Manual or the like).

At step 433, the system is configured to, in response to receiving the request for the audit report, retrieve merchant device information associated with the merchant. As discussed herein, in various embodiments, the system is configured to receive information regarding the chain of custody of various devices. In these embodiments (and others), the system is configured to locate and retrieve information regarding each device associated with the merchant. Such merchant device information may include any suitable information, including, but not limited to: a device identifier, a device location, a device serial number, number of transactions processed by a device, a device status (e.g., "active", "lost", "tampered", "stored", etc.), etc.

According to particular embodiments, the audit report (e.g., requested at step 431) may include an attestation to that the user (e.g., representing the merchant) has read, and/or that the merchant is in compliance with, a compliance manual. In these embodiments (and others), the system is configured to retrieve a copy of the compliance manual to display to the user.

At step 435, the system is configured to display the merchant device information. In various embodiments, the system is configured to display the merchant device information including the merchant device identifier, merchant device location, and merchant device status. In particular embodiments, the system is configured to display the copy of the compliance manual.

At step 437, the system is configured to request attestation of the merchant device information. In particular embodiments, the system is configured to request attestation by the user clicking one or more check boxes. In various embodiments, the system is configured to request attestation by the user typing or electronically signing their name. In further embodiments, the system is configured to request attestation by the user entering in a code, filling out a document, clicking a button, scrolling to the end of a page or electronic document, etc.

At step 439, the system is configured to receive an indication of attestation (e.g, the system is configured to receive an indication that the user has checked a box, filled out a form, signed an electronic form, etc.). At step 441, the system is configured to, in response to receiving the indication of attestation, compile the audit report, the audit report including the identifier of each device associated with the merchant, the status of each merchant device, and the indication of attestation. The system may be configured to compile the audit report in any suitable way and the audit report may be in any suitable format.

At step 443, the system is configured to transmit the audit report to the computing device associated with the merchant. The system may be configured to transmit the audit report to the computer device associated with the merchant by displaying the audit report, accessing and causing the computing device associated with the merchant to print the audit report, etc. In various embodiments, the system is configured to transmit a copy of the attested to audit report to various other entities, such as auditing entities, etc.

Exemplary Payment System Processes (FIG. 5A & FIG. 5B)

FIGS. 5A and 5B are exemplary processes performed by the P2PE Management System (e.g., P2PE Management System 510). FIG. 5A is an exemplary payload integrity verification process and FIG. 5B is an exemplary fingerprint creation process, which may be used as part of the payload integrity verification process.

Exemplary Payload Integrity Verification Process

Turning to FIG. 5A, the system, at step 530, is configured to receive a payload originating from a device, the payload including encrypted information and a device serial number. In various embodiments, the system is configured to receive the payload from a payment point of interaction device (e.g., a credit card swipe device). In particular embodiments, the system is configured to receive the payload from a health records computing device (e.g., a device that transmits sensitive health records for storage by the system). In further embodiments, the system is configured to receive the payload from a computing device associated with financial information (e.g., bank account information, etc.). In still further embodiments, the system is configured to receive the payload from any other suitable device such as a device transmitting sensitive information such a driver's license number, a social security number, etc.

The payload may include any suitable information (e.g., any suitable string of particular elements). In various embodiments, the payload includes encrypted information and the device serial number. In particular embodiments, the payload includes a key serial number that is used to decrypt the encrypted information. In one or more embodiments, the payload includes a device firmware number. In further embodiments, the payload includes any other suitable device or payload information associated with the device, transaction, and/or merchant in custody of the device.

The encrypted information may be any suitable information that has been encrypted, such as, for example, a social security number, a credit card number, payment information, a driver's license number, medical record information, a birthdate, a bank account number, a routing number, a name, etc. As discussed herein, the payload may be in any suitable format, which may be used as a fingerprint for device identification.

At step 532, the system is configured to parse the payload to extract the device serial number. In various embodiments, the system is configured to parse the payload to extract the device serial number by separating the encrypted information from the unencrypted information and determining which one or more unencrypted numbers are included in the device serial number. In particular embodiments, the payload includes a string of numbers and information and the device serial number is located in a particular location of the string (e.g., the device serial number may be the first number, the second number, the fifth number, etc.). As will be understood by one of ordinary skill in the art, the method of parsing the payload my depend upon the structure/format of the payload.

At step 534, the system is configured to retrieve a serial number table from the database, the serial number table including one or more serial numbers. At step 536, the system is configured to compare the device serial number to the serial number table to determine whether the device serial number is included in the serial number table. The system may be configured to compare the device serial number to the serial number table in any suitable way including searching for the device serial number, comparing the device serial number to all serial numbers in the table, and/or by using some other indicator (first number, etc.) to narrow down the one or more serial numbers included in the serial number table that may match the device serial number. It should be understood by one of ordinary skill in the art that the serial number table may be more than one suitable serial number table.

At step 538, the system is configured to, upon determining that the device serial number is included in the table, retrieve, from memory, a fingerprint associated with the device, wherein the fingerprint is an identifier for the device based on the format of one or more payloads that originated from the device (see FIG. 5B regarding discussion of fingerprint creation). In particular embodiments, the system is configured to create the fingerprint associated with the device, as further discussed herein. In further embodiments, the system is configured to receive the fingerprint associated with the device from third party system (e.g., a third-party system creates the fingerprint and transmits the fingerprint to the system. In still further embodiments, the device fingerprint is manually entered by one or more users.

At step 540, the system is configured to compare the payload to the fingerprint to determine whether the device has been compromised. In various embodiments, the system is configured to compare the format of the payload (e.g., the order of the particular elements of the payload) to the fingerprint (e.g., a representation of the format of a first payload receive from the device) to verify the format matches the fingerprint. In some embodiments, the system is configured to compare various elements of the payload to the format, such as the key serial number, the device firmware number, etc. to the fingerprint to determine whether the device has been compromised (e.g., the if the compared element does not match the corresponding portion of the fingerprint, the device may have been compromised).

At step 542, the system is configured to, upon determining that the device has not been compromised, facilitating decryption of the encrypted information. In various embodiments, the system is configured to facilitate decryption of the encrypted information by transmitting the encrypted information (and/or the entire payload) to an HSM for decryption. Upon determining that the device has been compromised, the may be configured to discard the payload, (e.g., not facilitate decryption of the encrypted information), notify the merchant, change a status of the device (e.g., as discussed herein), and/or no longer accept payloads from the device.

Exemplary Payload Fingerprint Process

Generally, FIG. 5B shows an exemplary process for generating a device fingerprint. Beginning with FIG. 5B, the system, at step 531, is configured to receive a payload from a device. The system may be configured to receive the payload from any suitable device, such as, for example, any suitable device discussed above regarding step 530.

At step 533, the system is configured to determine whether the received payload is the first payload received from the device. In various embodiments, the system is configured to determine whether the received payload is the first payload received from the device by comparing a serial number included in the received payload to a list of serial numbers of devices from which payloads have been received. In one or more embodiments, the system is configured to determine whether the received payload is the first payload received from the device by comparing a device identifier received from a user-interface (e.g., a user inputs device serial numbers) to an identifier included in the device payload.

At step 535, the system is configured to, based on determining that the received payload is the first payload received from the device, parse the received payload. The system may be configured to parse the device payload in any suitable way as discussed herein. At step 537, the system is configured to determine the format of the payload. The system may be configured to determine the format of the payload in any suitable way. Further, the format of the payload may vary and may be in any suitable form as discussed herein, such as CHR, HEX, Base64, or any other suitable format. In particular embodiments, the system may only store the format of the payload but may not store track data.

For example, the payload format may be in the following format:

FORMAT_CIPHERED_[TRACK1][_TRACK2][_KSN] [_DSN]

Continuing with the above example, "CIPHERED" is the encryption algorithm and may be, for example, RAW (data is unencrypted), TDES (DES DUKPT), or AES (AES DUKPT). Further, in this example, each TRACK is formatted at 1, 2, or 3, "+" and a CHR string "+" a string a numbers in HEX format, "+" a string of numbers in HEX format. Thus, in this example, TRACK1 above is formatted as 1+CHR+HEX+HEX. In this example, the fingerprint may be FORMAT is in HEX format, CIPHERED is TDES, TRACK1 is in 1+CHR+HEX+HEX format, TRACK2 is in 2+CHR+HEX+HEX format, KSN (key serial number) is in HEX format, and DSN (device serial number) is in HEX format. Therefore, the system may be configured to create a fingerprint, in this example of:

HEX_TDES_1+CHR+HEX+HEX_2+CHR+HEX+ HEX_HEX_HEX

At step 539, the system is configured to store in memory a fingerprint for the device, the fingerprint based on the format of the received payload. At step 541, the system is configured to compare each subsequent payload received from the device to device fingerprint (e.g., to determine whether the device has been compromised). In various embodiments, the system is configured to determine that the device has been compromised when the format of a particular subsequent payload does not match the device fingerprint (e.g., someone has changed something about the output of the device, such as the device firmware version number, etc.).

Exemplary UML Diagrams

FIGS. 6-14 show UML diagrams illustrating various sequences of the present systems and methods. Particularly, FIGS. 6-14 depict exemplary processes for point-to-point encryption (P2PE) transactions, wherein payloads may include encrypted data, unencrypted data, or both. It will be understood by one of ordinary skill in the art that these exemplary processes may be used in any type of transaction, including, but not limited to end to end encryption transactions. The lifelines and major process components will be used throughout (e.g., QSAPI is represented by QSAPI 602 across FIGS. 6-14, wherever present).

Figure 6:
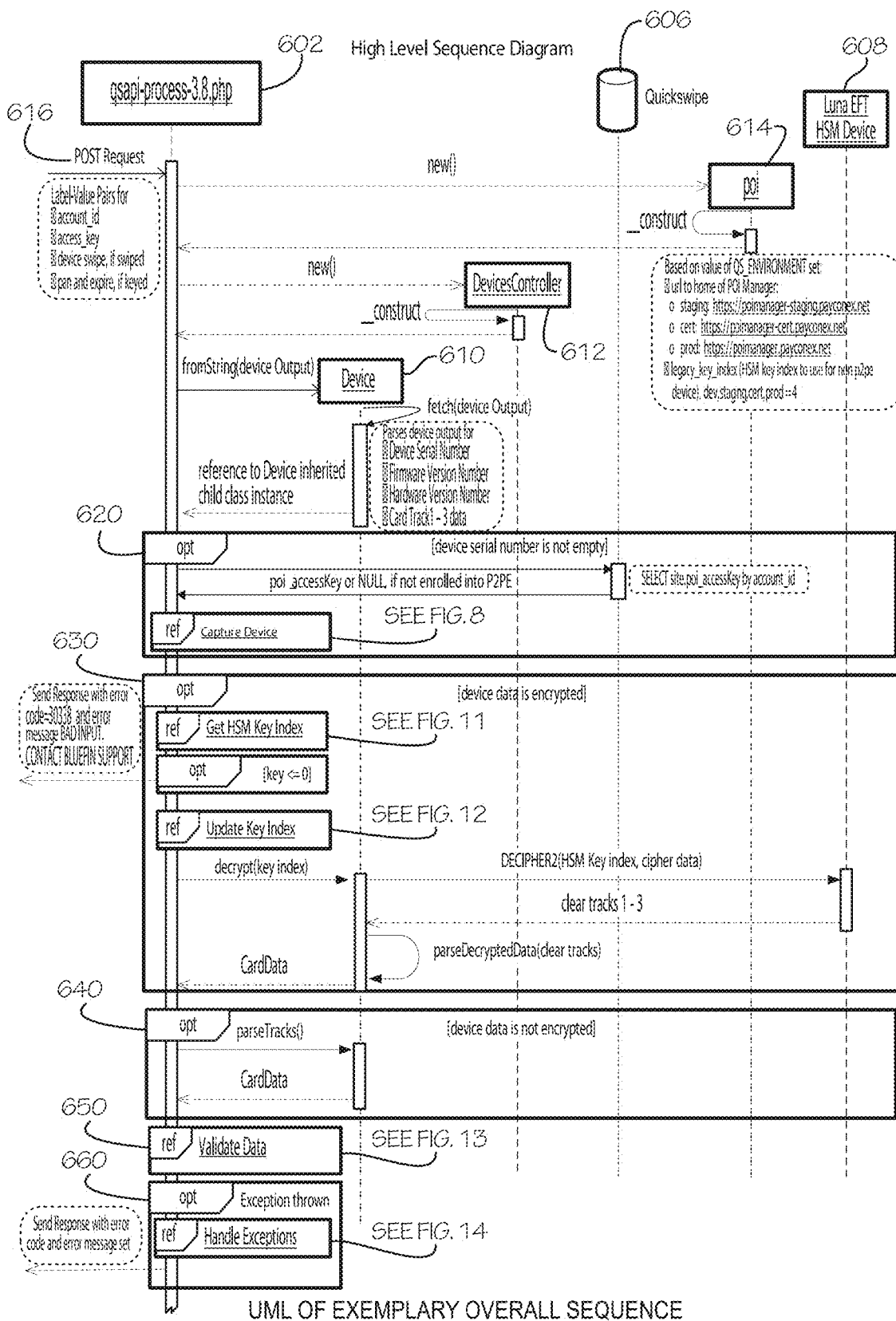
FIGS. 6-14 are UML diagrams illustrating exemplary sequences of the present systems and methods.
Figure 7:
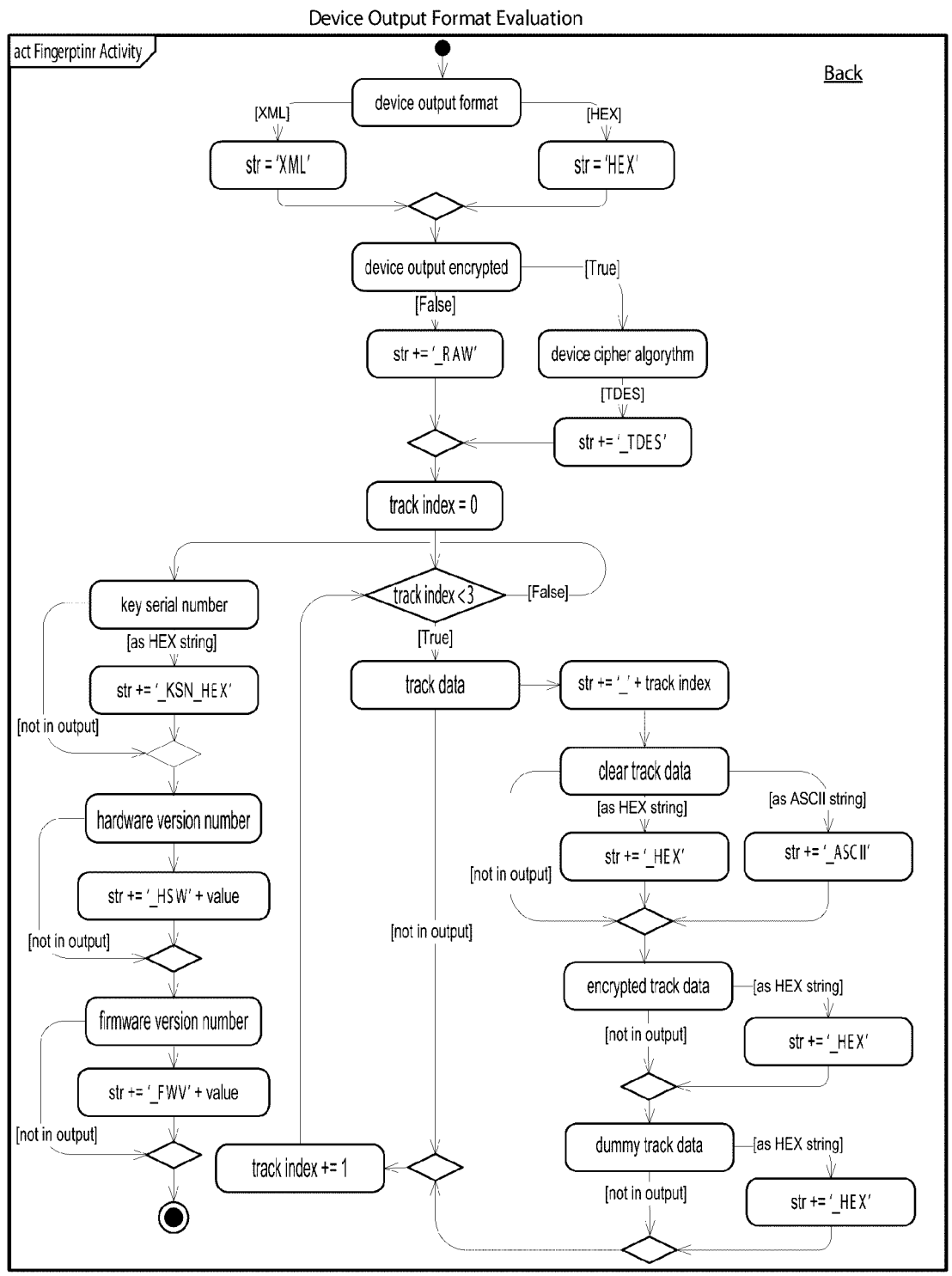

In various embodiments, as shown in FIG. 6, a customer (e.g., merchant) posts data to be processed to a web application (e.g., via a web browser) at POST request 616. Based on the data included in the post, the web application chooses a script to run. Generally, FIGS. 6-14 depict two script lifelines, qsapi-process-3.8.php 602 and validator.class.php 1320, which are further described below. As shown in FIGS. 6-14, the system uses at least two databases, a POI database (FIGS. 9 and 12) and a Quickswipe database (FIGS. 6, 8, 9, 10, 12, and 14). In various embodiments, the POI database is a database that POI Manager uses for persisting information on various devices. According to one or more embodiments, the Quickswipe database is a database operatively connected to qsapi-process-3.8.php 602 and used to store various qsapi-process-3.8.php 602 information.

Exemplary Overall System Sequence

Turning to FIG. 6, the lifeline qsapi-process-3.8.php 602, in the embodiments shown, implements majority of the P2PE management system functionality via a Quickswipe API ("QSAPI 602"). It should be understood by one of ordinary skill in the art that QSAPI 602 functionality may be implemented by any suitable number of APIs, scripts, and/or functions. For simplicity and brevity, only QSAPI 602 will be discussed. According to particular embodiments, and shown in FIG. 6, QSAPI 602 starts with instantiating specialized .PHP classes that encapsulate different aspects of processing as described herein, including, but not limited to instances of Device, DevicesController and poi classes.

Continuing with FIG. 6, "Device" class 610 is a base class for all supported devices (e.g., POI devices, etc.). In particular embodiments, each type of device (e.g., each device brand, model, etc.) associated with the system has a corresponding child class inherited from the Device class 610 (e.g., each brand of POI device has a separate child class). In various embodiments, each child class includes one or more aspects of a device's output inherited from the class, including, but not limited to device payload format (e.g., XML or binary format), an indication of whether data is encrypted etc. According to particular embodiments, the Device class 610 receives information regarding each type of device via a fromString (device output) string, as shown in FIG. 6, to instantiate the appropriate Device child class instance. In various embodiments, the Device class 610 uses the information in the appropriate child class to parse device payload (see fetch(device output)) for data decryption, if a device payload includes encrypted data. In the embodiments shown in FIG. 6, the system uses Luna EFT HSM Device 608 to decrypt device payload data.

In various embodiments, Device class 610 selects a child class to be instantiated via a method fromString( ) (e.g., based on the device type, etc.), creates a new( ) instance, and calls a fetch( ) method. According to particular embodiments, the fetch method parses device payload and stores parsed data. For example, Device class 610 method fromString( ) returns a reference that contains the parsed data of a particular payload. Continuing with this particular example, the fromString reference may contain card track 1, 2, 3 data, a device serial number, and/or device firmware and hardware information (as discussed herein, the device payload data may include any suitable information).

Continuing with FIG. 6, DevicesController class 612 is a controller class that, in particular embodiments, encapsulates several activities that QSAPI 602 uses to determine whether a particular device has been compromised, tampered with, etc. In particular embodiments, a DevicesController class 612 instance is initialized with Quickswipe database 606 accessors. In various embodiments, DevicesController class 612 transmits an indication of any such indication of device tampering to the POI Manager (e.g., P2PE Management System, see FIG. 9), upon detection. According to one or more embodiments, DevicesController class 612 retrieves and stores data at Quickswipe database 606 table entitled device_use.

An instance of poi class 614 is initialized by class_construct( ) method. The construct method, according to particular embodiments, retrieves an HSM key index from the POI Manager (see FIG. 9) for legacy devices (e.g., one or more device payloads received by the system from one or more devices that are not P2PE certified). As shown in FIGS. 6-14, example poi processes are logIncident( ) and getHsmKey( ). Generally, in various embodiments, poi class 614 posts requests to POI Manager and interprets POI Manager responses (see FIG. 9).

Figure 9:
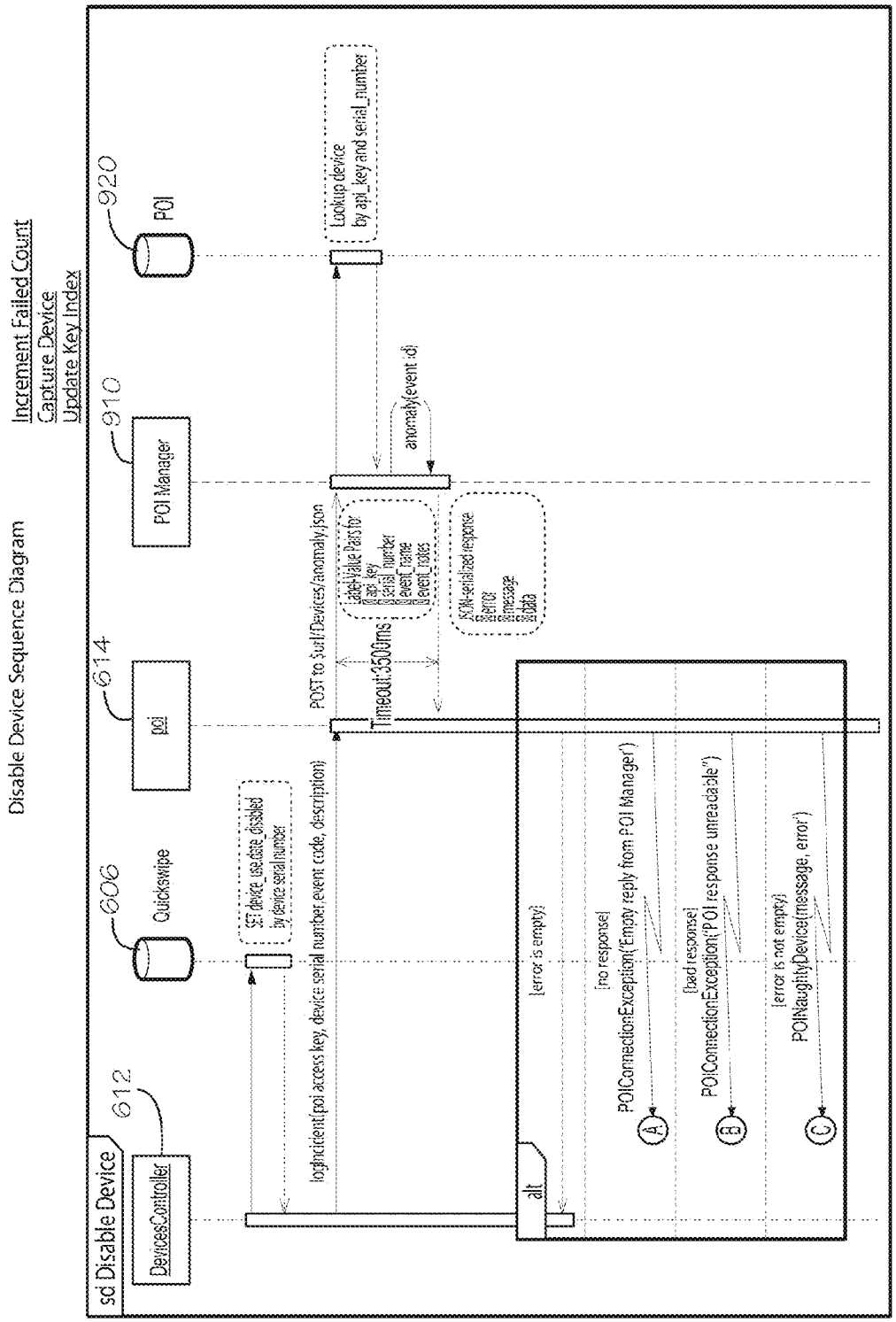

As shown in FIG. 6, Luna EFT HSM Device 608 (e.g., HSM Device 608), in various embodiments, is specialized hardware to encrypt or decrypt data. As discussed herein, according to particular embodiments, a particular device is injected with a key at a Key Injection Facility. In some embodiments (and others), this base key is stored in an HSM Device (e.g., HSM Device 608) in an internal table. Continuing with this embodiment, in order to decrypt encrypted data from the particular device payload, a decrypt( ) method passes a key index included in the particular device payload to the HSM Device 608 to derive the associated transaction key. In some embodiments, POI Manager stores HSM key indexes in POI database (as shown in FIG. 9) and QSAPI 602 retrieves various base keys by device serial number.

In various embodiments, once the Device class 610 inherited child class for a particular device is received, QSAPI 602 determines which one or more sub-processes (which "opt") to complete (e.g., sub-processes 620, 630, and 640). At step 620, if QSAPI 602 determines that the particular device payload does not contain a device serial number, QSAPI 602 processes the particular Device as non-P2PE device (e.g., accordingly, in these embodiments (and others), QSAPI 602 does not retrieve or request the POI Manager's access key from the Quickswipe database).

Figure 8:
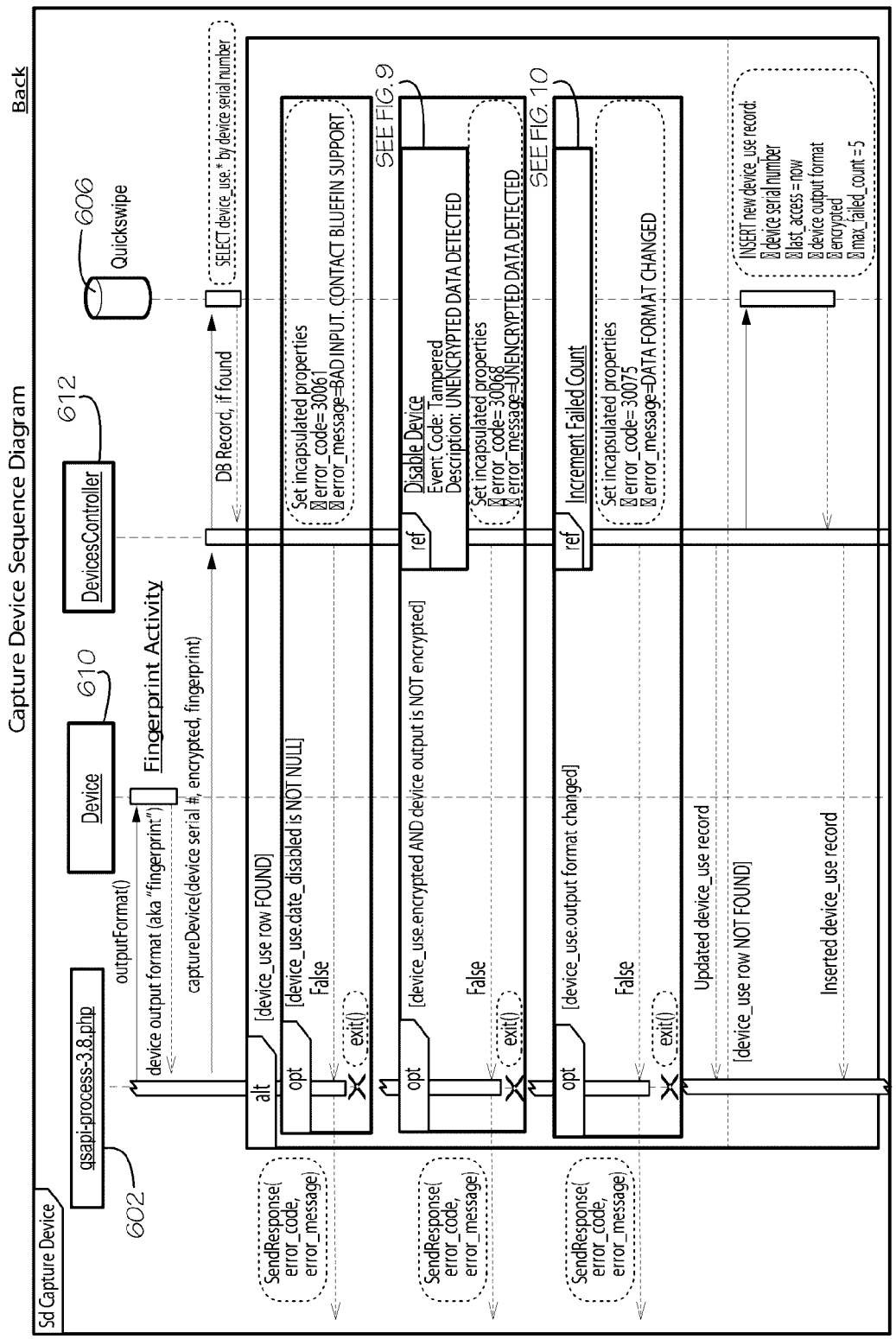

Continuing with step 630, if QSAPI 602 determines that the particular device payload includes a device serial number, QSAPI 602 compares the device payload with a fingerprint associated with the device (as discussed herein) at "Capture Device," which is further discussed at FIG. 8. In one or more embodiments, upon completion of the Capture Device process, QSAPI 602 receives a record of a device_use table in Quickswipe database 606.

Figure 11:
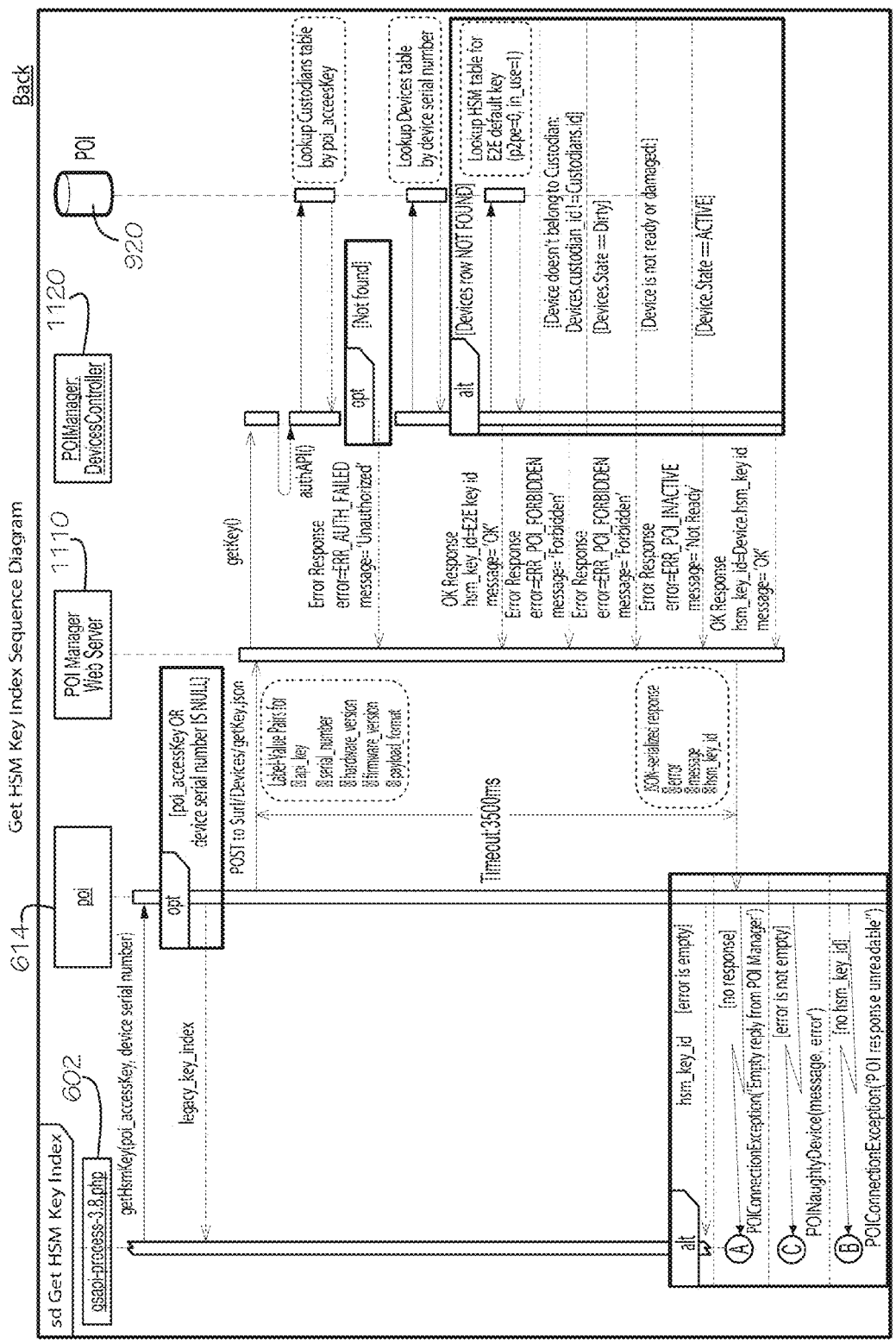

At step 630, if QSAPI 602 determines that the particular device payload includes encrypted data, QSAPI 602 retrieves an HSM key index from POI Manager to pass to HSM Device 608 for decryption as further described in FIG. 11 (Get HSM Key Index). If the Get HSM Key Index process returns a non-positive value, QSAPI 602 will terminate with sending an error response. Otherwise Get HSM Key Index returns an HSM key index for use in decrypting any encrypted data included in the payload of the particular device. See FIG. 12 for details on the Update Key Index process.

According to particular embodiments, upon completion of the Update Key Index process (e.g., at FIG. 12), QSAPI 602 returns a decrypt(key index) method, which is passed to Device class 610. In various embodiments, Device class 610 uses the key index provided by the decrypt(key index) method to transmit necessary data to the HSM Device 608 for decrypting the encrypted data of the payload of the particular device. In one or more embodiments, Device class 610 transmits a DECIPHER2 Luna EFT command (including the key index and cipher data) to HSM Device 608, which decrypts the encrypted payload data of the particular device. In further embodiments, once decrypted, the decrypted payload data is transmitted from the HSM Device 608 to Device class 610 and decrypted clear tracks data are parsed by parseDecryptedData( ). In these embodiments (and others), relevant data, including, but not limited to, parsed card tracks, PAN data, an expiration date, a cvv number, card holder data, etc. are included in a data container CardData as shown in FIG. 6.

At step 640, in some embodiments, upon determining that the particular device payload does not contain encrypted data, QSAPI 602 calls Device class 608 method parseTracks( ) to get a data container (e.g., CardData container) filled with a parsed card number, an expiration date, card holder data, etc. At step 650, QSAPI 602 validates the data included in the CardData container, which is further discussed regarding FIG. 13. At step 660, QSAPI 602 processes any exceptions at a Handle Exceptions process, which is further discussed regarding FIG. 14.

Exemplary Capture Device Sequence

Turning to FIG. 8, the exemplary capture device process discussed herein is implemented in embodiments where the payload of the particular device includes the device serial number. QSAPI 602 calls Device class 608 for a string that identifies certain features of the payload of the particular device (e.g., a device fingerprint as discussed herein and exemplary process shown in FIG. 7), including, for example, device payload format (e.g., XML, hexadecimal string, etc.), an indication of whether a portion of the device payload is encrypted, number of tracks included, etc. After a device payload format is determined, in various embodiments, QSAPI 602 calls DevicesController class 612 method captureDevice( ) with a device serial number, a device fingerprint, and a flag that indicates whether a portion of the device payload is encrypted.

In one or more embodiments, DevicesController class 612 searches for a record of the particular device in a device_use record table at the Quickswipe database 606 using the device serial number of the particular device (e.g., at CaptureDevice( ) above). Upon finding a record of the particular device at the Quickswipe database 606, DevicesController class 612, in particular embodiments, examines various aspects of the device_use information (e.g., stored in the Quickswipe database 606). In some embodiments, DevicesController class 612 determines whether the system has marked the particular device as tampered (e.g., the system has changed the state of the particular device to tampered). In these embodiments, the system is configured to determine that the particular device has been marked as tampered if the date_disabled column returns a "NOT NULL" value (e.g., indicating that the particular device is marked as tampered by the POI Manager). Upon receiving a value of NOT NULL for date_disabled column, according to particular embodiments, the captureDevice( ) method returns a "FALSE" value to QSAPI 602. In further embodiments, upon receiving the "FALSE" value for the captureDevice( ) method, the QSAPI 602 sends an error response to a user and terminates execution of the process (e.g., does not proceed with decryption of any encrypted payload information received from the particular device).

In various embodiments, upon receiving a value other than NOT NULL for the date_disabled column, the system determines whether the encryption flag for the particular device matches an encryption indication stored at the Quickswipe database 606. In particular embodiments, the system compares the received encrypted flag (e.g., as received with the payload at captureDevice( ), above) against the encryption flag stored for the particular device at Quickswipe database 606. According to particular embodiments, QSAPI 602 considers a change of encrypted flag (output was encrypted, but now data is not encrypted) for a particular device as an indication that the particular device is compromised or tampered and should be disabled. In these embodiments, the captureDevice( ) method returns FALSE to the QSAPI 602, which sends an error response to the user and terminates execution of the process. For more information regarding disabling devices, see FIG. 9.

According to one or more embodiments, upon determining that the received encryption flag matches the stored encryption indication at the Quickswipe database 606, the system is configured to compare the device payload format with a stored fingerprint for the particular device stored at the Quickswipe database 606. According to particular embodiments, QSAPI 602 considers a change in device fingerprint as a temporary failure (several intermittent factors can cause device payload format to be different, such as, for example, unreliable USB connection of device to the personal computer may cause a change in device payload format), for more details regarding temporary failure, see FIG. 10. In further embodiments, in response to the system determining the particular device payload format does not match the fingerprint, captureDevice( ) returns FALSE, which results in QSAPI 602 sending an error response to the user and to terminating execution of the process.

If all above checks were evaluated to False, captureDevice( ) method returns a current value of DEVICE_USE row to QSAPI 602. Upon determining that the particular device ss used for the first time (device_use row NOT FOUND), DevicesController class 612 inserts a new device_use row with a passed encrypted flag and a device fingerprint in the Quickswipe database 606.

Exemplary Disable Device Sequence

Turning to FIG. 9, according to various embodiments, POI Manager 910 tracks the chain of custody of devices. According to various embodiments, POI Manager 910 is implemented as collection of .PHP classes responsible for several activities. In some embodiments, POI Manager 910 returns an appropriate controller class, such as the DevicesController class 612 based on the type of request posted by QSAPI 602. As shown in FIG. 9, POI Manager 910 receives an indication to disable decryption of a particular device (e.g., the particular device discussed in the embodiments above) because the payload of the particular device is unencrypted (e.g., but should have been decrypted). In the embodiment shown in FIG. 9, the particular device will be disabled in Quickswipe database 606 and disable_date will be set to the value of current date and time. POI Manager 910 changes the state of the particular device to tampered in POI database 920.

Exemplary Increment Failed Count Sequence

Figure 10:
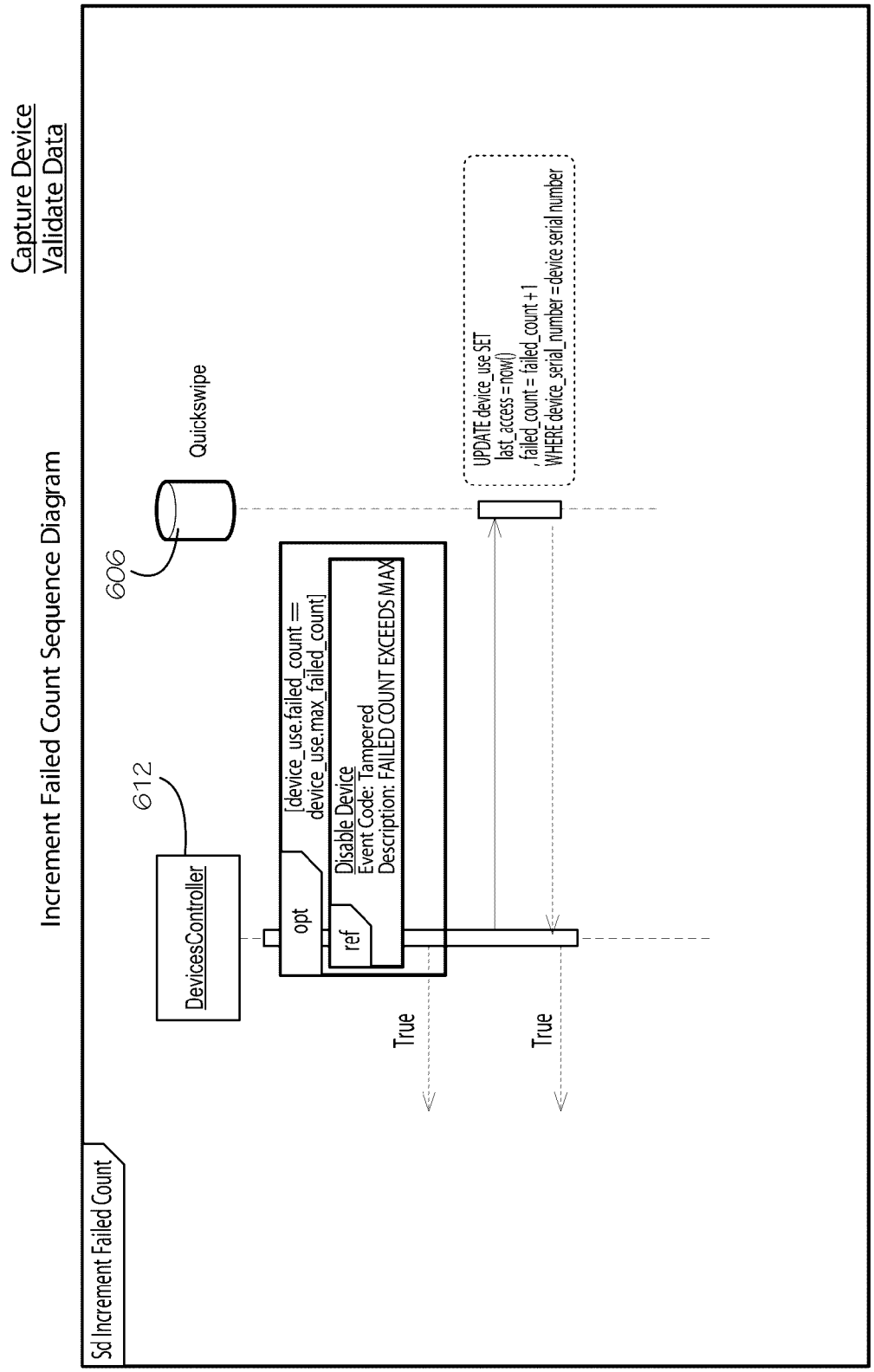

Turning to FIG. 10, QSAPI 602, in various embodiments, tracks each failed encryption attempt for every device with a known serial number. According to particular embodiments, when a particular device's information is captured for the first time, the system adds a new row to device_use table with failed_count set to 0 and max_failed_count set to a hardcoded limit (5, 10, etc.). In one or more embodiments, each time a payload is received from the particular device, QSAPI 602 runs a validation check. In further embodiments, QSAPI 602 increments the failed_count value each time a validation check fails. In still further embodiments, if the failed_count reaches the max_failed_count hardcoded limit (e.g., 2, 5, 7, 10, 20, etc.), the system disables the particular device (e.g., and no longer decrypts payloads received from the particular device). In particular embodiments, the system may be configured to reset the failed_count value to 0 with each passed validation check. In some embodiments, the system may be configured to increment the failed_count value with each failed validation check, regardless of whether there has been an intermediate passed validation check. An exemplary disable device process is described above in regards to FIG. 9.

Exemplary Get HSM Key Index Sequence

Upon determining that a particular device payload includes encrypted data, QSAPI 602 follows the exemplary process shown in FIG. 11. As discussed herein, in various embodiments, the particular device payload includes an integer value indicating a number of times a decryption key value was derived from a base key. In some embodiments, HSM Device 608 derives the encryption key from its internal copy of the base key and uses the derived encryption key to decrypt encrypted data in the particular device payload.

According to particular embodiments. QSAPI 602 retrieves a poi_accessKey corresponding to the particular device from poi class 614. In one or more embodiments, upon determining that the poi_accessKey is NULL or empty, poi class 614 returns a legacy_key_index (e.g., indicating that the particular device is a "legacy device" and not part of a P2PE decryption scheme). In various embodiments, upon determining that the particular device serial number is not empty and poi_accessKey is not NULL, poi class 614 requests an hsm_key_id from POI Manager Web Server 1110, as shown in FIG. 11.

As will be understood by one of ordinary skill in the art, in some embodiments, the HSM Device 608 stores more than one base key in an internal HSM Device table. Thus, in these embodiments (and other embodiments), the HSM Device 608 requires an indication of which of the more than one base key to use to decrypt the particular device payload. As described above, in some embodiments, POI Manager stores HSM key indexes in POI database (as shown in FIG. 9) and QSAPI 602 retrieves various base keys by device serial number and transmits the HSM key index (which indicates the base key to use to decrypt the particular device payload) to the HSM Device 608.

Exemplary Update Key Index Sequence

Figure 12:
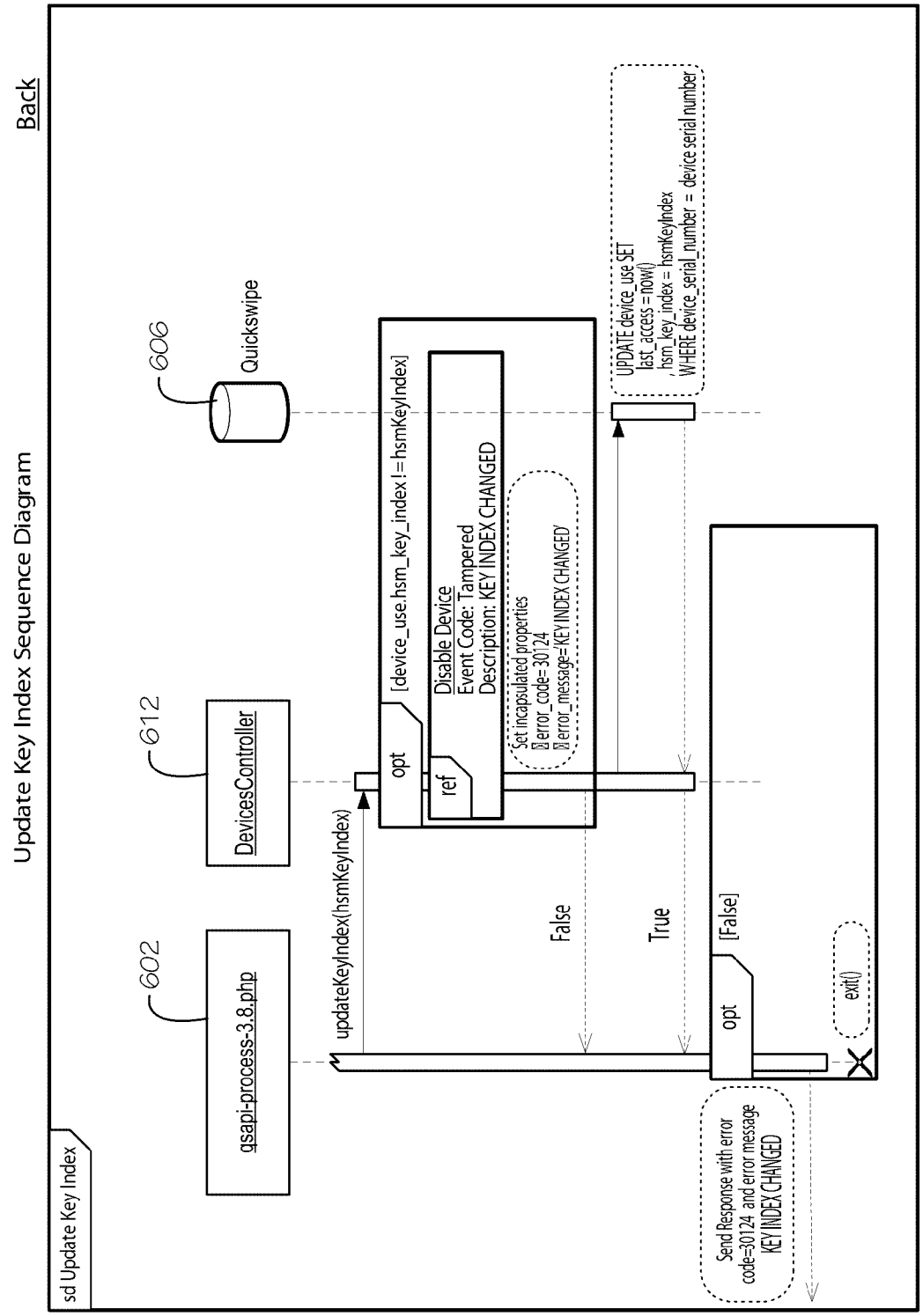

FIG. 12 shows an exemplary update key index sequence. As shown in the embodiment in FIG. 12, if the system determines that the key index associated with a particular device has changed, then the system is configured to disable the particular device, as discussed above.

Exemplary Validation Sequence

Figure 13:
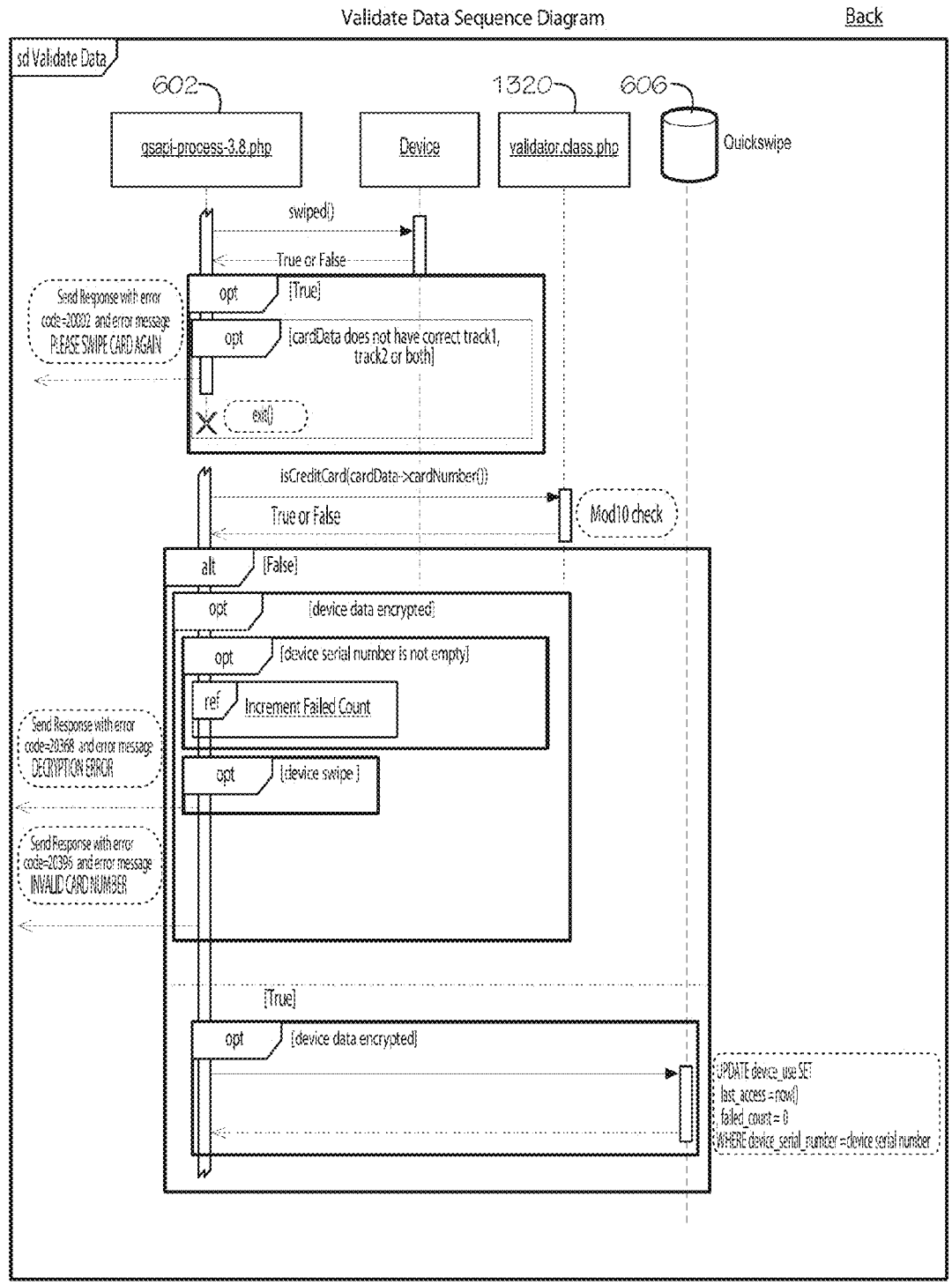
Figure 14:
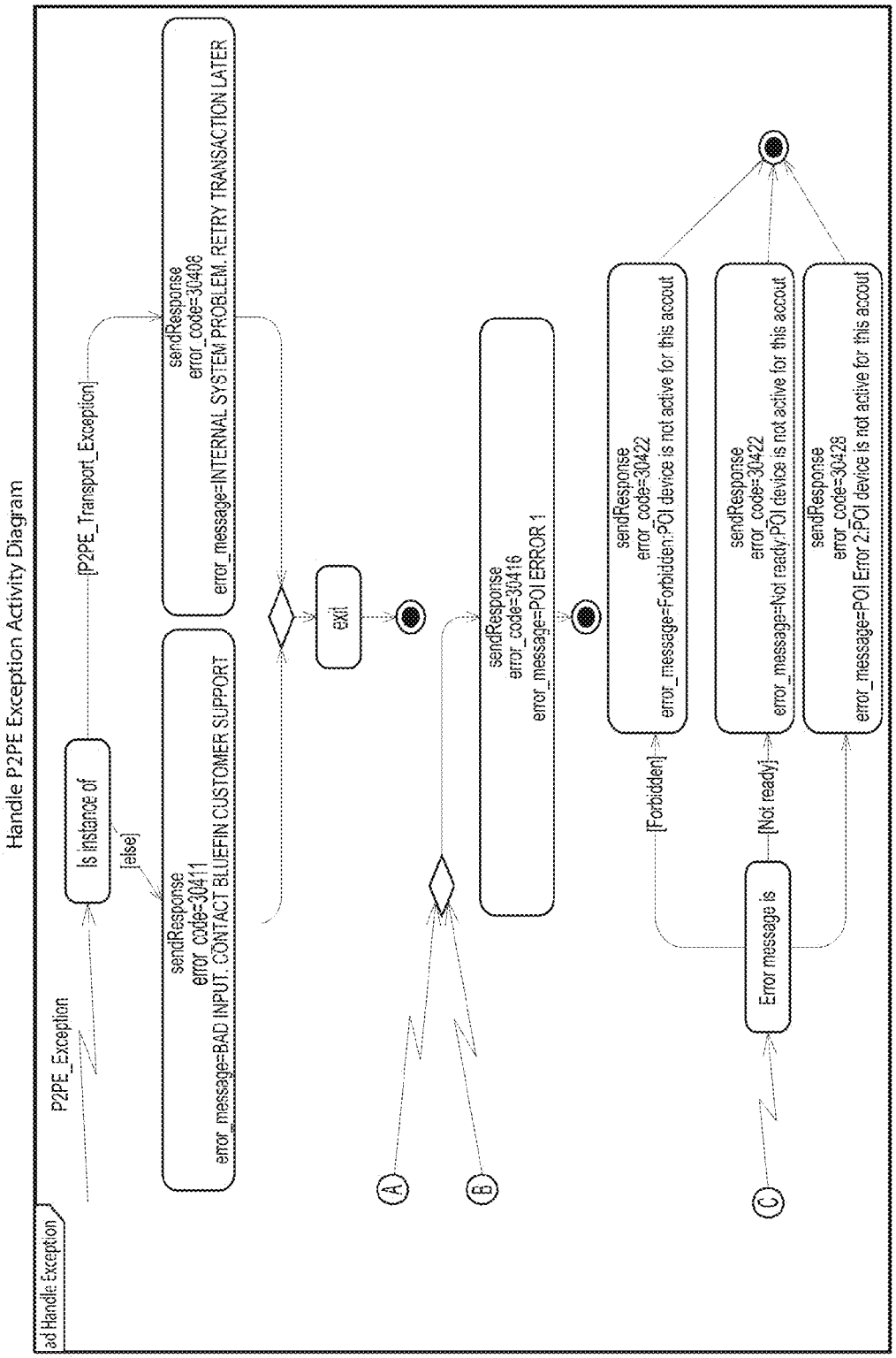

Turning to FIG. 13, in the embodiment shown, upon receiving a payload from a particular device, QSAPI 602 determines whether the payload includes track1 data in a correct format, track2 data in a correct format, or both (e.g., by checking the fingerprint associated with the particular device and/or other appropriate record). If the payload does not include track1 data in the correct format, track2 data in the correct format, or both, QSAPI 602 sends an error response to a user and terminates execution of the process. Continuing with this sequence, if the system determines the payload includes track1 data in the correct format, track2 data in the correct format, or both (or any suitable number of tracks), in particular embodiments, QSAPI 602 proceeds validating track1, track2 or both. According to particular embodiments, card track data shall be non-empty string of numbers 0-9, which pass mod 10 check at validator-.class.php 1320. In one or more embodiments, the system is configured to, upon successful validated card of the card track number, DevicesController class 612 resets device-_use.failed_count (as discussed above) for the particular device to zero (0).

Further Exemplary Processes

FIGS. 15-17 depict further exemplary processes of the systems discussed herein. In particular. FIG. 15 depicts an exemplary queuing process, FIG. 16 depicts an exemplary update process, and FIG. 17 depicts an exemplary decryption verification process. Each of these exemplary processes will be discussed below.

Exemplary Queuing Process

Turning now to FIG. 15, an exemplary queuing process is depicted. As further discussed herein, the system may be configured to queue various messages at a queue (e.g., MQTT Queues 231). In particular embodiments, the system may queue messages as a backup method in case a primary form of storage becomes unavailable. For example, in the example shown in FIG. 2B, should the Read/Write Database 232 stop functioning correctly, then queues hosted on the same machine as the Master Read-Only Database 230 may preserve messages sent from the Master Read-Only Database 230 to the Read/Write Database 232 until the Read/Write Database 232 is functioning or at least accepting and storing messages.

At step 1502, the system generates a message. As discussed herein, the message may be any suitable message generated by any suitable component of the system. In various embodiments, a frontend server (e.g., Authentication Web Server 224) may generate a log or other suitable event each time a payload is received and/or authenticated (as discussed herein). In particular embodiments, the frontend server may generate one or more exceptions that are to be written to a database (e.g., an exception recording that a particular payload has failed authentication, etc.). In at least one embodiment, other components of the system may generate a message to be queued, such as, for example, a master read-only database (e.g., Master Read-Only Database 230), a read-only database (e.g., Read-Only Database 228), or any other server or component discussed herein.

At step 1504, the system adds the message to the queue. In particular embodiments, the system includes a queue that is hosted on the same computing device that hosts the Master Read-Only Database 230 (FIG. 2). In these embodiments, still referring to FIG. 2, the system is configured to add messages being sent from the Authentication Web Server 224 to the queue.

At step 1506, the system stores the message at the queue. The system may be configured to store the message at the queue for any predetermined amount of time, until a particular event occurs, and/or until a particular set of circumstances are met. In a particular embodiment, the system is configured to store the message at the queue for a number of seconds, a number of minutes, a number of hours, for a particular number of days (e.g., until a weekend or particular weekday), etc. In some embodiments, the system is configured to store the message at the queue until the system is processing less than 250 (or, e.g., 500, 750, 1,000, etc.) payloads per second, then the queue may be configured to transmit the message. In further embodiments, the system may be configured to store the message until a particular amount of resources are available or until the intended recipient of the message (e.g., the Read/Write Database 232) can accept the message (e.g., is functioning, is not malfunctioning, is online, etc.).

At step 1508, the system determines whether a message recipient is configured to accept messages. At step 1510, the system, upon determining that the message recipient is configured to accept messages, transmits the stored messages to the message recipient (e.g., a read/write database). Upon determining that the message recipient is not configured to accept messages, the system is configured to continue adding messages to the queue, but to not transmit any stored messages to the message recipient.

Exemplary Update Process

FIG. 16 depicts an exemplary process for event-driven updates according to one embodiment of the present systems and methods. In various embodiments, the system is configured to update various databases of the system upon a particular event occurring, such as, for example, receiving a piece of information. In at least one embodiment, the system is configured to update various databases (e.g., the Master Read-Only Database 230) upon receiving information regarding a new device (e.g., information regarding a new POI device received at the P2PE Manager 166 as described in relation to FIG. 1).

At step 1602, the system generates or receives event information. As further discussed herein, the system may generate or receive any event information. In particular embodiments, the system may receive (or generate) event information related to new devices registered with the system (e.g., as discussed herein), event information related to state changes of a particular device (e.g., a particular device's status is changed from "active" to "tampered"), event information related to a particular device that failed decryption, etc.

At step 1604, the system transmits new authentication data based on the event information. In particular embodiments, the system is configured to generate authentication data from the event information for transmitting to one or more databases of the system for authentication and validation of payloads transmitted to the system. At step 1606, the system refreshes a master database to include the new authentication data. At step 1608, the system refreshes one or more slave databases to include new authentication data. As a particular example, the system receives event information that a new device is registered with the system. In this particular example, the event information includes a serial number (or other suitable identifier) associated with the device. The system, continuing with this particular example, formats or otherwise generates authentication information associated with the device to be transmitted to databases of the system. In this way, in this particular example, once the authentication data is transmitted to the databases of the system (e.g., to the Read-Only Database 228), the system can use this authentication information to authenticate payloads received from the device.

Exemplary Decryption Verification Process

Once a payload has been transmitted to, and processed by, a hardware security module, the system, in at least one particular embodiment, may be configured to verify that the payload was decrypted. An exemplary process for verifying decryption of a payload is shown in FIG. 17. Beginning at step 1702, a decryption server receives a payload that includes at least one encrypted element. In various embodiments, the decryption server is configured to receive the payload from any suitable source, including, but not limited to, a frontend server (e.g., Authentication Web Server 224), a load balancer, a read/write database, directly from a third party partner (e.g., payment processor, healthcare system, government system, etc.), etc.

At step 1704, the decryption server transmits the payload to a hardware security module for decryption of the at least one encrypted element. At step 1706, the decryption server receives the payload from the hardware security module (e.g., after the hardware security module decrypts or attempts to decrypt the at least one encrypted element of the payload).

At step 1708, the decryption server parses the payload to locate the at least one encrypted element. The system may be configured to parse the payload in any suitable way, such as by locating the at least one encrypted element based on the encrypted element's location within a string of text/code. At step 1710, the decryption server determines whether the hardware security module decrypted the at least one encrypted element. In various embodiments, the system is configured to determine whether the hardware security module decrypted the at least one encrypted element by comparing characters of the at least one encrypted element to a database of characters. In particular embodiments, the system is configured to determine whether the hardware security module decrypted the at least one encrypted element by comparing the number of characters of the at least one encrypted element (e.g., upon determining that the at least one encrypted element includes greater than, less than, or a certain number of characters, the system determines that the at least one encrypted element has been decrypted or has not been decrypted). In further embodiments, the system is configured to determine whether the hardware security module decrypted the at least one encrypted element by determining whether a payment card number is included in the payload (e.g., a credit card number or other payment information).

At step 1712, upon determining that the hardware security module did not decrypt the at least one encrypted element, the decryption server generates an error (e.g., which, in some embodiments, is transmitted to a read/write database and/or the third party partner) and may, in some embodiments, not transmit the payload to the third party partner. At step 1714, upon determining that the hardware security did decrypt the at least one encrypted element, the decryption server transmits the payload to the third party partner.

CONCLUSION

Aspects, features, and benefits of the claimed invention(s) will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

What is claimed is:

1. A system for decryption of payloads, the system comprising:
    a frontend server operatively connected to a first, second, and third read-only database, the frontend server configured for: a) receiving a plurality of payloads from one or more third parties, wherein each of the payloads includes at least one encrypted element; b) retrieving authentication data from the first, second and third read-only databases; c) comparing the authentication data with each of the plurality of payloads to determine whether one or more of the payloads of the plurality of payloads has been compromised; d) upon determining that one or more of the payloads of the plurality of payloads has not been compromised, transmitting the one or more payloads of the plurality of payloads to a hardware security module for decryption of the at least one encrypted element;
    the first, second, and third read-only databases operatively connected to the frontend server and configured for storing read-only authentication data for use in determining whether payloads have been compromised;
    a master read-only database operatively connected to the first, second, and third read-only databases and a read/write backend database, the master read-only database configured for receiving the authentication data from the read/write backend database and refreshing the authentication data at each of the first, second, and third read-only databases; and
    the hardware security module operatively connected to the frontend server, the hardware security module configured for decrypting the one or more payloads of the plurality of encrypted payloads based on an encryption key and transmitting the decrypted one or more payloads to the one or more third parties.

2. The system of claim 1, wherein each payload includes an identifier associated with a source of the payload.

3. The system of claim 2, wherein retrieving the authentication data from the first, second and third read-only databases comprises retrieving the authentication data from the first, second and third read-only databases for each of the received plurality of payloads by each identifier associated with each of the plurality of payloads.

4. The system of claim 3, wherein the identifier is a serial number or firmware identifier associated with a particular point of interaction device.

5. The system of claim 3, wherein the identifier is an identifier associated with a mobile payments system.

6. The system of claim 3, wherein the identifier is an identifier associated with an electronic health records system.

7. The system of claim 1, wherein:
    the hardware security module is a first hardware security module; and
    the system further comprises a second hardware security module operatively connected to the frontend server, the second hardware security module configured for decrypting the one or more payloads of the plurality of encrypted payloads based on an encryption key for the one or more payloads and transmitting the decrypted one or more payloads to the one or more third parties.

8. The system of claim 7, wherein the system is configured to process up to about 1600 transactions per second.

9. The system of claim 7, wherein the system is configured to process twice as many transactions by doubling the number of read-only databases and hardware security modules.

10. The system of claim 9, wherein the system is configured to process up to about 3200 transactions per second.

11. A computer-implemented method for decryption of payloads, the method comprising:
    providing a frontend server operatively connected to a first, second, and third read-only database, the frontend server configured for: a) receiving a plurality of payloads from one or more third parties, wherein each of the payloads includes at least one encrypted element; b) retrieving authentication data from at least one of the first, second, and third read-only databases; c) comparing the authentication data with each of the plurality of payloads to determine whether one or more of the payloads of the plurality of payloads has been compromised; d) upon determining that one or more of the payloads of the plurality of payloads has not been compromised, transmitting the one or more payloads of the plurality of payloads to a hardware security module for decryption of the at least one encrypted element;
    providing the first, second, and third read-only databases operatively connected to the frontend server and configured for storing read-only authentication data for use in determining whether payloads have been compromised;
    providing a master read-only database operatively connected to the first, second, and third read-only databases and a read/write backend database, the master read-only database configured for receiving the authentication data from the read/write backend database and refreshing the authentication data at each of the first, second, and third read-only databases; and
    providing the hardware security module operatively connected to the frontend server, the hardware security module configured for decrypting the one or more payloads of the plurality of encrypted payloads based on an encryption key and transmitting the decrypted one or more payloads to the one or more third parties.

12. The computer-implemented method of claim 11, wherein each payload includes an identifier associated with a source of the payload.

13. The computer-implemented method of claim 12, wherein retrieving the authentication data from at least one of the first, second, and third read-only databases comprises retrieving the authentication data from at least one of the first, second, and third read-only databases for each of the received plurality of payloads by each identifier associated with each of the plurality of payloads.

14. The computer-implemented method of claim 13, wherein the identifier is a serial number or firmware identifier associated with a particular point of interaction device.

15. The computer-implemented method of claim 13, wherein the identifier is an identifier associated with a mobile payments system.

16. The computer-implemented method of claim 13, wherein the identifier is an identifier associated with an electronic health records system.

17. The computer-implemented method of claim 11, wherein:
the hardware security module is a first hardware security module; and
the computer-implemented method further comprises providing a second hardware security module operatively connected to the frontend server, the second hardware security module configured for decrypting the one or more payloads of the plurality of encrypted payloads based on an encryption key for the one or more payloads and transmitting the decrypted one or more payloads to the one or more third parties.

18. The computer-implemented method of claim 17, wherein the computer-implemented method enables processing of up to about 1600 transactions per second.

19. The computer-implemented method of claim 17, wherein the computer-implemented method enables processing twice as many transactions by providing twice as many read-only databases and hardware security modules.

20. The computer-implemented method of claim 19, wherein the computer-implemented method enables processing of up to about 3200 transactions per second.

21. A scalable system for fast decryption of payloads, the system comprising:
at least one hardware security module operatively connected to one or more frontend servers and configured for decrypting encrypted elements of payloads;
the one or more frontend servers configured to receive and authenticate payloads based at least in part upon retrieving authentication data from a particular read-only database of at least three read-only databases;
the at least three read-only databases operatively connected to the one or more frontend servers, wherein the at least three read-only databases comprise the authentication data for authenticating payloads;
a read-only master database operatively connected to the at least three read-only databases, the read-only master database configured to receive the authentication data from the backend read/write database and refresh the authentication data stored at the at least three read-only databases; and
a backend read/write database for logging decryptions and authentications, the backend read/write database operatively connected to the at least one hardware security module and the read-only master database.

22. The system of claim 21, wherein the system comprises a particular number of one or more frontend servers and a specific number of one or more read-only databases based on a ratio of read-only databases and frontend servers to a number of hardware security modules.

23. The system of claim 22, wherein the system comprises three read-only databases for every two hardware security modules.

24. The system of claim 21, wherein:
the at least one hardware security module is configured to decrypt encrypted elements of payloads at a particular number of payloads per second; and
the system comprises a number of read-only databases such that the read-only databases can authenticate the particular number of payloads per second.

25. The system of claim 24, wherein the system comprises two hardware security modules and is configured to decrypt up to 3200 payloads per second.

26. The system of claim 24, wherein the system comprises four hardware security modules and is configured to decrypt up to 6400 payloads per second.

27. The system of claim 26, wherein the system comprises six read-only databases and is configured to authenticate up to 6400 payloads per second.

28. The system of claim 21 wherein the at least one hardware security module is configured to decrypt encrypted data in a 3DES format.

29. The system of claim 21, wherein the at least one hardware security module is configured to decrypt encrypted data in a DUKPT format.

30. The system of claim 21, wherein the at least one hardware security module is configured to decrypted encrypted data in a BPS format.

31. The system of claim 21, wherein the at least one hardware security module is configured to decrypted encrypted data in a base64 encoded format.

32. The system of claim 21, wherein the at least one hardware security module is configured to decrypted encrypted data in a hexadecimal encoded format.

33. The system of claim 21, wherein the at least one hardware security module is configured to decrypted encrypted data in an encrypted value name format.

34. The system of claim 21, wherein the at least one hardware security module is configured to decrypted encrypted data in any of the following formats: 3DES, DUKPT, BPS, base64, hexadecimal encoded, or encrypted value name.

35. A system for fast decryption of one or more payloads, the system comprising:
a message queuing protocol operatively connected to a first read-only database and a read/write database, the message queuing protocol configured for:
receiving event notifications from the first read-only database, wherein the event notifications each comprise one or more notifications regarding the authentication of one or more received payloads;
queuing the event notifications received from the first read-only database; and
transmitting the event notifications to the read/write database upon determining that the read/write database is configured to accept event notifications;
second and third read-only databases operatively connected to the frontend server and configured for storing authentication data for use in determining whether a payload has been compromised; and
a master read-only database operatively connected to the first, second, and third read-only databases and the read/write database, the master read-only database configured for receiving the authentication data from the read/write database and refreshing the authentication data at each of the first, second, and third read-only databases.

36. The system of claim 35, wherein the system further comprises a frontend server operatively connected to at least one slave read-only database, the frontend server configured for receiving the one or more received payloads and authenticating each of the one or more received payloads by comparing data included in the one or more received payloads with data included in the at least one slave read-only database.

37. The system of claim 36, wherein the system further comprises a hardware security module, wherein the hardware security module is operatively connected to the frontend server and is for decrypting encrypted portions of the one or more received payloads.

38. The system of claim 37, wherein the hardware security module is operatively connected to the frontend server via a hardware security module server.

39. The system of claim 35, wherein the message queuing protocol is further configured for storing the event notifications upon determining the read/write database is not configured to accept event notifications.

40. The system of claim 39, wherein upon determining the read/write database is configured to accept event notifications, transmitting the stored event notifications to the read/write database.

41. The system of claim 35, wherein the read/write database is a P2PE manager.

* * * * *